US011207399B2

(12) United States Patent
Bilsel et al.

(10) Patent No.: US 11,207,399 B2
(45) Date of Patent: *Dec. 28, 2021

(54) INFLUENZA VIRUS MUTANTS AND USES THEREFOR

(71) Applicant: FluGen, Inc., Madison, WI (US)

(72) Inventors: Pamuk Bilsel, Madison, WI (US); Yasuko Hatta, Madison, WI (US)

(73) Assignee: FluGen, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/368,315

(22) Filed: Mar. 28, 2019

(65) Prior Publication Data

US 2020/0061182 A1 Feb. 27, 2020

Related U.S. Application Data

(63) Continuation of application No. 15/917,926, filed on Mar. 12, 2018, now Pat. No. 11,040,098, which is a continuation of application No. 15/040,277, filed on Feb. 10, 2016, now Pat. No. 9,919,042, which is a continuation of application No. 14/128,415, filed as application No. PCT/US2012/043606 on Jun. 21, 2012, now Pat. No. 9,284,533.

(60) Provisional application No. 61/501,034, filed on Jun. 24, 2011.

(51) Int. Cl.

| | |
|---|---|
| *A61K 39/145* | (2006.01) |
| *C12N 7/00* | (2006.01) |
| *C07K 14/005* | (2006.01) |
| *A61K 39/12* | (2006.01) |
| *A61K 35/76* | (2015.01) |
| *A61K 39/00* | (2006.01) |

(52) U.S. Cl.
CPC .......... *A61K 39/145* (2013.01); *A61K 35/76* (2013.01); *A61K 39/12* (2013.01); *C07K 14/005* (2013.01); *C12N 7/00* (2013.01); *A61K 2039/5254* (2013.01); *A61K 2039/54* (2013.01); *A61K 2039/543* (2013.01); *A61K 2039/545* (2013.01); *A61K 2039/552* (2013.01); *A61K 2039/58* (2013.01); *A61K 2039/70* (2013.01); *C12N 2760/16121* (2013.01); *C12N 2760/16122* (2013.01); *C12N 2760/16134* (2013.01); *C12N 2760/16151* (2013.01); *C12N 2760/16162* (2013.01); *C12N 2760/16171* (2013.01); *C12N 2760/16234* (2013.01); *C12N 2760/16262* (2013.01)

(58) Field of Classification Search
None
See application file for complete search history.

(56) References Cited

U.S. PATENT DOCUMENTS

| | | | |
|---|---|---|---|
| 7,176,021 B2 | 2/2007 | Kawaoka | |
| 8,057,796 B2 * | 11/2011 | Grandea, III | ........ C07K 14/005 424/147.1 |
| 8,475,806 B2 * | 7/2013 | Kawaoka | ............... C12N 15/86 424/206.1 |
| 9,284,533 B2 | 3/2016 | Bilsel et al. | |
| 9,309,536 B2 | 4/2016 | John et al. | |
| 9,474,798 B2 * | 10/2016 | Watanabe | ............ A61K 39/145 |
| 2005/0003349 A1 | 1/2005 | Kawaoka | |
| 2005/0232950 A1 | 10/2005 | Kawaoka | |
| 2009/0074812 A1 | 3/2009 | Watanabe et al. | |
| 2010/0021499 A1 | 1/2010 | Bilsel et al. | |
| 2010/0061995 A1 | 3/2010 | Carragher et al. | |
| 2010/0247572 A1 | 9/2010 | Kawaoka | |
| 2011/0172609 A1 | 7/2011 | Moga et al. | |
| 2011/0172637 A1 | 7/2011 | Moga et al. | |
| 2011/0172638 A1 | 7/2011 | Moga et al. | |
| 2011/0172639 A1 | 7/2011 | Moga et al. | |
| 2011/0172645 A1 | 7/2011 | Moga et al. | |
| 2012/0109066 A1 | 5/2012 | Chase et al. | |

FOREIGN PATENT DOCUMENTS

| | | |
|---|---|---|
| CN | 1809633 A | 7/2006 |
| CN | 1810961 A | 8/2006 |
| EP | 3 447 131 | 2/2019 |
| JP | 2007-525175 A | 9/2007 |
| JP | 2014-517181 | 7/2014 |
| JP | 2017-227944 | 12/2017 |
| JP | 2017-227945 A | 12/2017 |
| WO | WO-98/28478 | 7/1998 |
| WO | WO-2004/094466 | 11/2004 |
| WO | WO-2009/064805 A1 | 5/2009 |

OTHER PUBLICATIONS

Bilsel, et al. "Mutations in the Cytoplasmic Tail of Influenza A Virus Neuraminidase Affect Incorporation into Virions," Journal of Virology, Nov. 1993, pp. 6762-6767, vol. 67, No. 11.
Enami, et al., "High-Efficiency Formation of Influenza Virus Transfectants," Journal of Virology, May 1991, pp. 2711-2713, vol. 65, No. 5.
Hatta, et al., "An M2 cytoplasmic tail mutant as a live attenuate influenza vaccine against pandemic (H1N1) 2009 influenza virus," Vaccine, Mar. 2011, pp. 2308-2312, vol. 29, Issue 12.
Iwatsuki-Horimoto, et al., "The Cytoplasmic Tail of the Influenza A Virus M2 Protein Plays a Role in Viral Assembly," Journal of Virolpogy, Jun. 1, 2006, pp. 5233-5240, vol. 80, No. 11.
Luytjes, et al., "Amplification, expression, and packaging of a foreign gene by influenza virus," Cell, Dec. 22, 1989, pp. 1107-1113, vol. 59, Issue 6.

(Continued)

*Primary Examiner* — Agnieszka Boesen
(74) *Attorney, Agent, or Firm* — Foley & Lardner LLP

(57) ABSTRACT

Disclosed herein are compositions and methods related to mutant viruses, and in particular, mutant influenza viruses. The mutant viruses disclosed herein include a mutant M2 sequence, and are useful in immunogenic compositions, e.g., as vaccines. Also disclosed herein are methods, compositions and cells for propagating the viral mutants, and methods, devices and compositions related to vaccination.

20 Claims, 58 Drawing Sheets

Specification includes a Sequence Listing.

(56) References Cited

OTHER PUBLICATIONS

McCown, et al., "Distinct Domains of the Influenza A Virus M2 Protein Cytoplasmic Tail Mediate Binding to the M1 Protein and Facilitate Infectious Virus Production," Journal of Virology, Aug. 2006, pp. 8178-8189, vol. 80, No. 16.
McCown, et al., "The Influenza A Virus M2 Cytoplasmic Tail is Required for Infectious Virus Production and Efficient Genome Packaging," Journal of Virology, Mar. 2005, pp. 3595-3605, vol. 79, No. 6.
Morris, et al., "Influenza A virus segment 7 genes for matrix protein 1 and matrix protein 2, genomic RNA," GenBank: AJ298948.1, Nov. 14, 2006, 2 pages.
Neumann, et al., "Generation of influenza A viruses entirely from cloned cDNAs," PNAS, Aug. 3, 1999, pp. 9345-9350, vol. 96, No. 16.
Pushko, et al., "Influenza virus-like particles comprised of the HA, NA, and M1 proteins of H9N2 influenza virus induce protective immune responses in BALB/c mice," Vaccine, Dec. 30, 2005, pp. 5751-5759, vol. 23, No. 50.
Reed, et al., "A Simple Method of Estimating Fifty Per Cent Endpoints," American Journal of Hygiene, May 1938, pp. 493-497, vol. 27, No. 3.
Reuman, et al., "Assessment of signs of influenza illness in the ferret model," Journal of Virological Methods, Apr.-May 1989, pp. 27-34, vol. 24, Issues 1-2.
Treanor, et al., "Passively Transferred Monoclonal Antibody to the M2 Protein Inhibits Influenza A Virus Replication in Mice," Journal of Virology, Mar. 1990, pp. 1375-1377, vol. 64, No. 3.
Watanabe et al., "Influenza A Virus Lacking M2 Protein as a Live Attenuated Vaccine", Journal of Virology, vol. 83, No. 11, 2009, pp. 5947-5950.
Watanabe, et al., "Influenza A virus lacking M2 protein as a live attenuated vaccine," Journal of Virology, Jun. 2009, pp. 5947-5950, vol. 83, No. 11.
Watanabe, et al., "Novel Approach to the Development of Effective H5N1 Influenza A Virus Vaccines: Use of M2 Cytoplasmic Tail Mutants," Journal of Virology, Mar. 2008, pp. 2486-2492, vol. 82, No. 5.
Zebedee, et al., "Influenza A Virus M2 Protein: Monoclonal Antibody Restriction of Virus Growth and Detection of M2 in Virions," Journal of Virology, Aug. 1988, pp. 2762-2772, vol. 62, No. 8.
First Office Action in CN Patent Application No. 201611019615.4 dated Dec. 24, 2019 (no English translation) (7 pages).
Communication pursuant to Article 94(3) EPC in EP Application No. 12803054.1 dated Apr. 18, 2016 (6 pages).
Communication pursuant to Article 94(3) EPC in EP Application No. 12803054.1, dated Jul. 17, 2017 (6 pages).
Decision of Rejection in CN Application No. 201280040857.5 dated Aug. 1, 2016 (with English translation) (11 pages).
European Search Report for application No. 18183256.9 dated Jan. 28, 2019.
Examination Reporton AU Application No. 2012272837, dated Nov. 17, 2016, 4 pages.
Extended Search Report in EP Application No. 12803054.1 dated Dec. 9, 2014 (9 pages).
Final Office Action in JP Application No. 2014-517181 dated Feb. 1, 2017 (with English translation) (4 pages).
Final Office Action in JP Application No. 2014-517181 dated Apr. 4, 2016 (with English translation) (6 pages).
Final Office Action on U.S. Appl. No. 15/917,926 dated Oct. 1, 2019.
First Examination Report received in NZ Application No. 620242 dated Nov. 24, 2014 (2 pages).
First Office Action in CN Application No. 201280040857.5 dated Apr. 3, 2015 (with English translation) (23 pages).
First Office Action in MX Application No. MX/a/2014/000254 dated Oct. 24, 2016(with English translation) (4 pages).
International Preliminary Report on Patentability in International Application No. PCT/US2012/043606 dated Dec. 24, 2013 (10 pages).
International Search Report and Written Opinion in International Application No. PCT/US2012/043606 dated Jul. 22, 2013 (18 pages).
Non-Final Office Action on U.S. Appl. No. 15/917,926 dated Dec. 31, 2018.
Non-Final Rejection Office Action in U.S. Appl. No. 15/040,277 dated May 15, 2017 (9 pages).
Non-Final Rejection Office Action on U.S. Appl. No. 15/040,705 dated May 12, 2017 (8 pages).
Notice of Allowance in U.S. Appl. No. 14/128,415 dated Feb. 18, 2016 (2 pages).
Notice of Allowance in U.S. Appl. No. 14/128,415 dated Nov. 6, 2015 (5 pages).
Notice of Allowance on U.S. Appl. No. 15/040,277 dated Nov. 6, 2017 (6 pages).
Notice of Allowance on U.S. Appl. No. 15/040,705 dated Nov. 6, 2017 (5 pages).
Notice of Preliminary Rejection issued for KR 10-2014-7001965, dated Apr. 18, 2018.
Notice of Preliminary Rejection issued for KR 10-2014-7001965, dated Dec. 24, 2018.
Notice of Preliminary Rejection issued for KR 10-2018-7023457, dated Nov. 5, 2018.
Notice of Preliminary Rejection issued for KR 10-2018-7023462, dated Nov. 5, 2018.
Notice of Preliminary Rejection on KR Patent Application No. 10-2018-7023457 dated Jul. 8, 2019 (with English translation) (5 pages).
Notice of Preliminary Rejection on KR Patent Application No. 10-2018-7023462 dated Jul. 8, 2019 (with English translation) (5 pages).
Notice of Rejection on KR Patent Application No. 10-2014-7001965 dated Jul. 23, 2019 (with English translation) (4 pages).
Notification of the Second Office Action received in CN Application No. 201280040857.5 dated Dec. 22, 2015 (with English translation) (19 pages).
Notification of the Third Office Action in CN Application No. 201280040857.5 dated Mar. 28, 2018 (with English translation) (8 pages).
Office Action issued for CA 2875484, dated Feb. 12, 2018.
Office Action issued for MX MX/a/2017/003937, dated Sep. 10, 2018.
Office Action on MX Application No. MX/a/2017/003936, dated Apr. 23, 2018, 8 pages with translation.
Office Action on MX Patent Application No. MX/a/2017/003937 dated May 27, 2019 (no English translation) (4 pages).
Non-Final Office Action in U.S. Appl. No. 15/917,926 dated Apr. 17, 2020.
Notice of Preliminary Rejection in KR Patent Application No. 10-2020-7004751 dated Mar. 27, 2020 (with English translation) (7 pages).
Notice of Reasons for Refusal in JP Patent Application No. 2019-041172 dated Apr. 8, 2020 (with English translation) (12 pages).
Fourth Office Action in MX Patent Application No. MX/a/2017/003937 dated Sep. 8, 2020 (with English translation) (10 pages).

* cited by examiner

FIGURE 3

"wild-type" M1/M2 nucleic acid sequence (3' to 5')

AGCAAAAGCAGGTAGATATTGAAAGatgagtcttctaaccgaggtcgaaacGTACGTACTCTCTATC
ATCCCGTCAGGCCCCCTCAAAGCCGAGATCGCACAGAGACTTGAAGATGTCTTTGCA
GGGAAGAACACCGATCTTGAGGTTCTCATGGAATGGCTAAAGACAAGACCAATCCT
GTCACCTCTGACTAAGGGGATTTTAGGATTTGTGTTCACGCTCACCGTGCCCAGTGA
GCGAGGACTGCAGCGTAGACGCTTTGTCCAAAATGCCCTTAATGGGAACGGGGATC
CAAATAACATGGACAAAGCAGTTAAACTGTATAGGAAGCTCAAGAGGGAGATAACA
TTCCATGGGGCCAAAGAAATCTCACTCAGTTATTCTGCTGGTGCACTTGCCAGTTGT
ATGGGCCTCATATACAACAGGATGGGGGCTGTGACCACTGAAGTGGCATTTGGCCT
GGTATGTGCAACCTGTGAACAGATTGCTGACTCCCAGCATCGGTCTCATAGGCAAAT
GGTGACAACAACCAATCCACTAATCAGACATGAGAACAGAATGGTTTTAGCCAGCA
CTACAGCTAAGGCTATGGAGCAAATGGCTGGATCGAGTGAGCAAGCAGCAGAGGCC
ATGGAGGTTGCTAGTCAGGCTAGACAAATGGTGCAAGCGATGAGAACCATTGGGAC
TCATCCTAGCTCCAGTGCTGGTCTGAAAAATGATCTTCTTGAAAATTTGCAGgcctatcag
aaacgaatgggggtgcagatgcaacggttcaagtgatcctctcactattgccgcaaatatcattgggatcttgcacttgacattgtggattcttg
atcgtctttttttcaaatgcatttaccgtcgctttaaatacggactgaaaggagggccttctacggaaggagtgccaaagtctatgagggaaga
atatcgaaaggaacagcagagtgctgtggatgctgacgatggtcattttgtcagcatagagctggagtaaAAAACTACCTTGTT
TCTACT Anti-PR8 polyclonal sera Anti-M2 monoclonal antibody PR8 H1N1 challenge Aichi (H3N2) challenge A. Virus titers after PR8 (H1N1) challenge Virus titers after Aichi (H3N2) challenge

|  | M2KO CA07 | FluMist CA07 | M2WT CA07 |
|---|---|---|---|
| Lung PFU /g | 0.00 | 2.26 | 7.26 |
| NT PFU /g | 0.00 | 3.38 | 5.41 |

FROM FIGURE 44C

FIGURE 44D

|  | PRIME-BOOST | | | | | | | AFTER CHALLENGE |
|---|---|---|---|---|---|---|---|---|
|  |  | 7 | 14 | 21 | 35 | 42 | 49 | day 70 |
| FIGURE 49A | M2KO | 34 | 500 | 1,542 | 9,831 | 7,236 | 4,971 | 51,362 |
|  | FluMist | 55 | 8,989 | 13,159 | 12,101 | 20,405 | 12,629 | 64,725 |
|  | Naïve | 13 | 41 | 24 | 0 | 0 | - |  |

BOOST ↓ (at day 21)

|  | PRIME ONLY | | | |
|---|---|---|---|---|
|  |  | d.35 | 14 d.42 av | 21 d.49 av |
| FIGURE 49B | M2KO | 12 | 92 | 872 | 52,767 |
|  | FluMist | 23 | 5,548 | 10,533 | 56,240 |
|  | Naïve |  |  |  | 7,356 |

FIGURE 50

Brisbane 10

Bar chart: Virus titer (y-axis, log scale from 1 to 1000000) vs Days post inoculation or introduced (x-axis: 1, 3, 5, 7, 9, 14). Legend: Donor A, Donor B, Donor C, Contact A, Contact B, Contact C, Aerosol A, Aerosol B, Aerosol C.

FIGURE 53

|  | Guinea Pig | day 0 | day 30 | day 60 |  |
|---|---|---|---|---|---|
| Saline | 1 | 1 | 1 | 263 | Av. 211 ± 59 |
|  | 2 | 1 | 1 | 1 |  |
|  | 3 | 1 | 100 | 259 |  |
|  | 4 | 1 | 1 | 1 |  |
|  | 5 | 1 | 1 | 150 |  |
|  | 6 | 1 | 1 | 170 |  |
| IM (prime boost) | 13 | 1 | 2,238 | 8,272 | Av. 15,877 ± 12,333 |
|  | 14 | 1 | 3,217 | 8,794 |  |
|  | 15 | 1 | 770 | 25,799 |  |
|  | 16 | 318 | 3,952 | 7,408 |  |
|  | 17 | 1 | 9,276 | 36,543 |  |
|  | 18 | 1 | 1,109 | 8,446 |  |
| ID FGN (prime boost) | 19 | 1 | 2,072 | 7,220 | Av. 6,391 ± 3,109 |
|  | 20 | 1 | 4,254 | 5,545 |  |
|  | 21 | 188 | 6,765 | 9,589 |  |
|  | 22 | 124 | 792 | 941 |  |
|  | 23 | 1 | 7,402 | 9,015 |  |
|  | 24 | 1 | 3,397 | 6,034 |  |
| IM (prime only) | 31 | 1 | 1,696 | 3,778 | Av. 3,463 ± 2,704 |
|  | 32 | 1 | 1,720 | 1,181 |  |
|  | 33 | 273 | 897 | 2,533 |  |
|  | 34 | 1 | 5,530 | 2,425 |  |
|  | 35 | 1 | 6,929 | 8,714 |  |
|  | 36 | 1 | 1,070 | 2,147 |  |
| ID FGN (prime only) | 37 | 119 | 5,217 | 6,875 | Av. 6,312 ± 1,966 |
|  | 38 | 1 | 7,785 | 8,812 |  |
|  | 39 | 1 | 5,404 | 7,041 |  |
|  | 40 | 1 | 2,426 | 2,894 |  |
|  | 41 | 1 | 5,707 | 6,616 |  |
|  | 42 | 1 | 2,063 | 5,634 |  |

```
                        SEQUENCE LISTING

<160> NUMBER OF SEQ ID NOS: 33

<210> SEQ ID NO 1
<211> LENGTH: 976
<212> TYPE: DNA
<213> ORGANISM: Influenza A virus

<400> SEQUENCE: 1
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga tttaggatt tgtgttcacg ctcaccgtgc ccagtgagcg     240
aggactgcag cgtagacgct ttgtccaaaa tgcccttaat gggaacgggg atccaaataa     300
catggacaaa gcagttaaac tgtataggaa gctcaagagg gagataacat tccatggggc     360
caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgattaata ggatcgtctt tttttcaaat gcatttaccg tcgctttaaa tacggactga     840
```

```
aaggagggcc ttctacggaa ggagtgccaa agtctatgag ggaagaatat cgaaaggaac      900
agcagagtgc tgtggatgct gacgatggtc attttgtcag catagagctg gagtaaaaaa      960
ctaccttgtt tctact                                                      976
```

```
<210> SEQ ID NO 2
<211> LENGTH: 1027
<212> TYPE: DNA
<213> ORGANISM: Influenza A virus

<400> SEQUENCE: 2
agcaaaagca ggtagatatt gaaagatgag tcttctaacc gaggtcgaaa cctacgtact       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggaacgggg atccaaataa      300
catggacaaa gcagttaaac tgtataggaa gctcaagagg gagataacat ccatggggc       360 caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaatccact      540
aatcagacat gagaacagaa tggttttagc cagcactaca gctaaggcta tggagcaaat      600
ggctggatcg agtgagcaag cagcagaggc catggaggtt gctagtcagg ctagacaaat      660
ggtgcaagcg atgagaacca ttgggactca tcctagctcc agtgctggtc tgaaaaatga      720
tcttcttgaa aatttgcagg cctatcagaa acgaatgggg gtgcagatgc aacggttcaa      780
gtgattaata gactattgcc gcaaatatca ttgggatctt gcacttgaca ttgtggattc      840
ttgatcgtct tttttcaaa tgcatttacc gtcgctttaa atacggactg aaaggagggc      900
cttctacgga aggagtgcca aagtctatga gggaagaata tcgaaaggaa cagcagagtg      960
ctgtggatgc tgacgatggt cattttgtca gcatagagct ggagtaaaaa actaccttgt      1020
ttctact                                                               1027
```

```
<210> SEQ ID NO 3
<211> LENGTH: 976
<212> TYPE: DNA
<213> ORGANISM: Influenza A virus

<400> SEQUENCE: 3
agcaaaagca ggtagatatt gaaagatgag tcttctaacc gaggtcgaaa cctacgtact       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggaacgggg atccaaataa      300
catggacaaa gcagttaaac tgtataggaa gctcaagagg gagataacat ccatggggc       360 caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaatccact      540
aatcagacat gagaacagaa tggttttagc cagcactaca gctaaggcta tggagcaaat      600
ggctggatcg agtgagcaag cagcagaggc catggaggtt gctagtcagg ctagacaaat      660
```

```
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgattaata ggatcgtctt tttttcaaat gcatttaccg tcgctttaaa tacggactga    840
aaggagggcc ttctacggaa ggagtgccaa agtctatgag gaagaatat cgaaaggaac     900 agcagagtgc tgtggatgct gacgatggtc attttgtcag catagagctg gagtaaaaaa    960
ctaccttgtt tctact                                                    976
```

<210> SEQ ID NO 4
<211> LENGTH: 24
<212> TYPE: PRT
<213> ORGANISM: Influenza A virus

<400> SEQUENCE: 4

Met Ser Leu Leu Thr Glu Val Glu Thr Pro Ile Arg Asn Glu Trp Gly
1               5                   10                  15

Cys Arg Cys Asn Gly Ser Ser Asp
            20

<210> SEQ ID NO 5
<211> LENGTH: 97
<212> TYPE: PRT
<213> ORGANISM: Influenza A virus

<400> SEQUENCE: 5

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 6
<211> LENGTH: 86
<212> TYPE: PRT
<213> ORGANISM: Influenza A virus

<400> SEQUENCE: 6

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Phe Lys Tyr Gly Leu
        35                  40                  45

Lys Gly Gly Pro Ser Thr Glu Gly Val Pro Lys Ser Met Arg Glu Glu
    50                  55                  60

Tyr Arg Lys Glu Gln Gln Ser Ala Val Asp Ala Asp Asp Gly His Phe
65                  70                  75                  80

Val Ser Ile Glu Leu Glu
                85

```
<210> SEQ ID NO 7
<211> LENGTH: 92
<212> TYPE: PRT
<213> ORGANISM: Influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Lys Cys Ile Tyr Arg
        35                  40                  45

Arg Phe Lys Tyr Gly Leu Lys Gly Gly Pro Ser Thr Glu Gly Val Pro
    50                  55                  60

Lys Ser Met Arg Glu Glu Tyr Arg Lys Glu Gln Gln Ser Ala Val Asp
65                  70                  75                  80

Ala Asp Asp Gly His Phe Val Ser Ile Glu Leu Glu
                85                  90

<210> SEQ ID NO 8
<211> LENGTH: 95
<212> TYPE: PRT
<213> ORGANISM: Influenza A virus

<400> SEQUENCE: 8

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Leu Phe Phe Lys Cys
        35                  40                  45

Ile Tyr Arg Arg Phe Lys Tyr Gly Leu Lys Gly Gly Pro Ser Thr Glu
    50                  55                  60

Gly Val Pro Lys Ser Met Arg Glu Glu Tyr Arg Lys Glu Gln Gln Ser
65                  70                  75                  80

Ala Val Asp Ala Asp Asp Gly His Phe Val Ser Ile Glu Leu Glu
                85                  90                  95

<210> SEQ ID NO 9
<211> LENGTH: 294
<212> TYPE: DNA
<213> ORGANISM: Influenza A virus

<400> SEQUENCE: 9
atgagtcttc taaccgaggt cgaaacgcct atcagaaacg aatggggtg cagatgcaac        60 ggttcaagtg atcctctcac tattgccgca aatatcattg ggatcttgca cttgacattg      120
tggattcttg atcgtctttt tttcaaatgc atttaccgtc gctttaaata cggactgaaa      180
ggagggcctt ctacggaagg agtgccaaag tctatgaggg aagaatatcg aaaggaacag      240
cagagtgctg tggatgctga cgatggtcat tttgtcagca tagagctgga gtaa            294

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 10
acacaccgtc tctaggatcg tctttttttc aaatgcattt acc                43

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cacacacgtc tcctattagt agaaacaagg tagttttt                      38

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acacaccgtc tcatcctatt aatcacttga accgttgc                      38

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacacacgtc tccgggagca aaagcaggta g                             31

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acacaccgtc tccctacgta ctctctatca tcccg                         35

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacacacgtc tcctattagt agaaacaagg tagttttt                      38

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggagcaaaa gcaggtagat attgaaagat gagtcttcta accgaggtcg aaac         54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtaggtttcg acctcggtta gaagactcat ctttcaatat ctacctgctt ttgc         54

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acacaccgtc tccctacgta ctctctatca tcccg                              35

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacacacgtc tcctattagt agaaacaagg tagttttt                           38

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gggagcaaaa gcaggtagat attgaaagat gagtcttcta accgaggtcg aaac         54

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtaggtttcg acctcggtta gaagactcat ctttcaatat ctacctgctt ttgc         54

<210> SEQ ID NO 22
<211> LENGTH: 31
<212> TYPE: DNA
<213> ORGANISM: Influenza A virus

<400> SEQUENCE: 22
caacggttca agtgattaat aaactattgc c                                  31

```
<210> SEQ ID NO 23
<211> LENGTH: 31
<212> TYPE: DNA
<213> ORGANISM: Influenza A virus

<400> SEQUENCE: 23
caacggttca agtgattggt ggactgttgc c                              31

<210> SEQ ID NO 24
<211> LENGTH: 1772
<212> TYPE: DNA
<213> ORGANISM: Influenza A virus

<400> SEQUENCE: 24
agcaaaagca ggggaaaata aaacaaacca aaatggagaa aatagtgctt ctttttgcaa    60
tagtcagtct tgttaaaagt gatcagattt gcattggtta ccatgcaaac aactcgacag   120
agcaggttga cacaataatg gaaaagaacg ttactgttac acatgcccaa gacatactgg   180
aaaagaaaca caacgggaag ctctgcgatc tagatggagt gaagcctcta attttgagag   240
attgtagcgt agctggatgg ctcctcggaa acccaatgtg tgacgaattc atcaatgtgc   300
cggaatggtc ttacatagtg gagaaggcca atccagtcaa tgacctctgt tacccagggg   360
atttcaatga ctatgaagaa ttgaaacacc tattgagcag aataaaccat tttgagaaaa   420
ttcagatcat ccccaaaagt tcttggtcca gtcatgaagc ctcattaggg gtgagctcag   480
catgtccata ccagggaaag tcctcctttt tcagaaatgt ggtatggctt atcaaaaaga   540
acagtacata cccaacaata aagaggagct acaataatac caaccaagaa gatcttttgg   600
tactgtgggg gattcaccat cctaatgatg cggcagagca gacaaagctc tatcaaaacc   660
caaccaccta tatttccgtt gggacatcaa cactaaacca gagattggta ccaagaatag   720
ctactagatc caaagtaaac gggcaaagtg gaaggatgga gttcttctgg acaattttaa   780
agccgaatga tgcaatcaac ttcgagagta atggaaattt cattgctcca gaatatgcat   840
acaaaattgt caagaaaggg gactcaacaa ttatgaaaag tgaattggaa tatggtaact   900
gcaacaccaa gtgtcaaact ccaatggggg cgataaactc tagcatgcca ttccacaata   960
tacaccctct caccattggg gaatgcccca aatatgtgaa atcaaacaga ttagtccttg  1020
cgactgggct cagaaatagc cctcaaagag agactagagg attatttgga gctatagcag  1080
gttttataga gggaggatgg cagggaatgg tagatggttg gtatgggtac caccatagca  1140
atgagcaggg gagtgggtac gctgcagaca agaatccac tcaaaaggca atagatggag  1200
tcaccaataa ggtcaactcg atcattgaca aaatgaacac tcagtttgag gccgttggaa  1260
gggaatttaa caacttagaa aggagaatag agaatttaaa caagaagatg gaagacgggt  1320
tcctagatgt ctggacttat aatgctgaac ttctggttct catggaaaat gagagaactc  1380
tagactttca tgactcaaat gtcaagaacc tttacgacaa ggtccgacta cagcttaggg  1440
ataatgcaaa ggagctgggt aacggttgtt tcgagttcta tcataaatgt gataatgaat  1500
gtatggaaag tgtaagaaat ggaacgtatg actacccgca gtattcagaa gaagcgagac  1560
taaaaagaga ggaaataagt ggagtaaaat tggaatcaat aggaatttac caaatactgt  1620
caatttattc tacagtggcg agttccctag cactggcaat catggtagct ggtctatcct  1680 tatgggatgtg ctccaatggg tcgttacaat gcagaatttg catttaagat tagaatttca  1740
gagatatgag gaaaaacacc cttgtttcta ct                                1772
```

<210> SEQ ID NO 25
<211> LENGTH: 1398
<212> TYPE: DNA
<213> ORGANISM: Influenza A virus

<400> SEQUENCE: 25
agcaaaagca ggggtttaaa atgaatccaa atcagaagat aataaccatc ggatcaatct 60
gtatggtaac tggaatagtt agcttaatgt tacaaattgg gaacatgatc tcaatatggg 120
tcagtcattc aattcacaca gggaatcaac accaatctga accaatcagc aatactaatt 180
ttcttactga gaaagctgtg gcttcagtaa aattagcggg caattcatct ctttgcccca 240
ttaacggatg ggctgtatac agtaaggaca acagtataag gatcggttcc aagggggatg 300
tgtttgttat aagagagccg ttcatctcat gctcccactt ggaatgcaga actttctttt 360
tgactcaggg agccttgctg aatgacaagc actccaatgg gactgtcaaa gacagaagcc 420
ctcacagaac attaatgagt tgtcctgtgg gtgaggctcc ctccccatat aactcaaggt 480
ttgagtctgt tgcttggtca gcaagtgctt gccatgatgg caccagttgg ttgacgattg 540
gaatttctgg cccagacaat ggggctgtgg ctgtattgaa atacaatggc ataataacag 600
acactatcaa gagttggagg aacaacatac tgagaactca agagtctgaa tgtgcatgtg 660
taaatggctc ttgctttact gtaatgactg acggaccaag taatggtcag gcatcacata 720
agatcttcaa aatggaaaaa gggaaagtgg ttaaatcagt cgaattggat gctcctaatt 780
atcactatga ggaatgctcc tgttatccta atgccggaga aatcacatgt gtgtgcaggg 840
ataattggca tggctcaaat cggccatggg tatctttcaa tcaaaatttg gagtatcaaa 900
taggatatat atgcagtgga gttttcggag acaatccacg ccccaatgat ggaacaggta 960
gttgtggtcc ggtgtcctct aacggggcat atggggtaaa agggttttca tttaaatacg 1020
gcaatggtgt ctggatcggg agaaccaaaa gcactaattc caggagcggc tttgaaatga 1080
tttgggatcc aaatgggtgg actgaaacgg acagtagctt ttcagtgaaa caagatatcg 1140
tagcaataac tgattggtca ggatatagcg ggagttttgt ccagcatcca gaactgacag 1200
gactagattg cataagacct tgtttctggg ttgagttgat cagagggcgg cccaaagaga 1260
gcacaatttg gactagtggg agcagcatat ctttttgtgg tgtaaatagt gacactgtgg 1320
gttggtcttg gccagacggt gccgagttgc cattcaccat tgacaagtag tctgttcaaa 1380
aaactccttg tttctact 1398

<210> SEQ ID NO 26
<211> LENGTH: 1779
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
agcaaaagca ggggaaaaca aaagcaacaa aaatgaaggc aatactagta gttctgctat 60
atacatttgc aaccgcaaat gcagacacat tatgtatagg ttatcatgcg aacaattcaa 120
cagacactgt agacacagta ctagaaaaga atgtaacagt aacacactct gttaaccttc 180
tagaagacaa gcataacggg aaactatgca aactaagagg ggtagcccca ttgcatttgg 240
gtaaatgtaa cattgctggc tggatcctgg gaaatccaga gtgtgaatca ctctccacag 300
caagctcatg gtcctacatt gtggaaacac ctagttcaga caatggaacg tgttacccag 360
gagatttcat cgattatgag gagctaagag agcaattgag ctcagtgtca tcatttgaaa 420

```
ggtttgagat attccccaag acaagttcat ggcccaatca tgactcgaac aaaggtgtaa    480
cggcagcatg tcctcatgct ggagcaaaaa gcttctacaa aaatttaata tggctagtta    540
aaaaaggaaa ttcataccca aagctcagca atcctacat taatgataaa gggaagaag      600
tcctcgtgct atggggcatt caccatccat ctactagtgc tgaccaacaa agtctctatc    660
agaatgcaga tgcatatgtt tttgtgggt catcaagata cagcaagamg ttcaagccgg     720
aaatagcaat aagacccaaa gtgagggatc ragaagggag aatgaactat tactggacac    780
tagtagagcc gggagacaaa ataacattcg aagcaactgg aaatctagtg gtaccgagat    840
atgcattcgc aatggaaaga atgctggat ctggtattat catttcagat acaccagtcc     900
acgattgcaa tacaacttgt caaacaccca agggtgctat aaacaccagc ctcccatttc    960
agaatataca tccgatcaca attggaaaat gtccaaaata tgtaaaaagc acaaaattga   1020
gactggccac aggattgagg aatatcccgt ctattcaatc tagaggccta tttggggcca   1080
ttgccggttt cattgaaggg ggtggacag ggatggtaga tggatggtac ggttatcacc    1140
atcaaaatga gcaggggtca ggatatgcag ccgacctgaa gagcacacag aatgccattg   1200
acgagattac taacaaagta aattctgtta ttgaaaagat gaatacacag ttcacagcag   1260
taggtaaaga gttcaaccac ctggaaaaaa gaatagagaa tttaaataaa aaagttgatg   1320
atggttttct ggacatttgg acttacaatg ccgaactgtt ggttctattg gaaaatgaaa   1380
gaactttgga ctaccacgat tcaaatgtga agaacttata tgaaaaggta agaagccagc   1440
taaaaaacaa tgccaaggaa attggaaacg gctgctttga attttaccac aaatgcgata   1500
acacgtgcat ggaaagtgtc aaaaatggga cttatgacta cccaaaatac tcagaggaag   1560
caaaattaaa cagagaagaa atagatgggg taaagctgga atcaacaagg atttaccaga   1620
ttttggcgat ctattcaact gtcgccagtt cattggtact ggtagtctcc ctgggggcaa   1680
tcagtttctg gatgtgctct aatgggtctc tacagtgtag aatatgtatt taacattagg   1740
atttcagaag catgagaaaa aaacacccctt gtttctact                         1779
```

<210> SEQ ID NO 27
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
agcaaaagca ggagtttaaa atgaatccaa accaaaagat aataaccatt ggttcggtct     60
gtatgacaat tggaatggct aacttaatat tacaaattgg aaacataatc tcaatatgga    120
ttagccactc aattcaactt gggaatcaaa atcagattga acatgcaat caaagcgtca     180
ttacttatga aaacaacact tgggtaaatc agacatatgt taacatcagc aacaccaact    240
ttgctgctgg acagtcagtg gtttccgtga attagcggg caattcctct ctctgccctg    300
ttagtggatg ggctatatac agtaaagaca acagtgtaag aatcggttcc aaggggggatg   360
tgtttgtcat aagggaacca ttcatatcat gctccccctt ggaatgcaga accttcttct    420
tgactcaagg ggccttgcta aatgacaaac attccaatgg aaccattaaa gacaggagcc    480
catatcgaac cctaatgagc tgtcctattg tgaagttcc ctctccatac aactcaagat     540
ttgagtcagt cgcttggtca gcaagtgctt gtcatgatgg catcaattgg ctaacaattg    600
gaatttctgg cccagacaat ggggcagtgg ctgtgttaaa gtacaacggc ataataacag    660
```

```
acactatcaa gagttggaga acaatatat tgagaacaca agagtctgaa tgtgcatgtg      720
taaatggttc ttgctttact gtaatgaccg atggaccaag taatggacag gcctcataca      780
agatcttcag aatagaaaag ggaaagatag tcaaatcagt cgaaatgaat gcccctaatt      840
atcactatga ggaatgctcc tgttatcctg attctagtga aatcacatgt gtgtgcaggg      900
ataactggca tggctcgaat cgaccgtggg tgtctttcaa ccagaatctg aatatcaga      960 taggatacat atgcagtggg attttcggag acaatccacg ccctaatgat aagacaggca     1020
gttgtggtcc agtatcgtct aatggagcaa atggagtaaa agggttttca ttcaaatacg     1080
gcaatggtgt ttggatgggg agaactaaaa gcattagttc aagaaacggt tttgagatga     1140
tttgggatcc gaacggatgg actgggacag acaataactt ctcaataaag caagatatcg     1200
taggaataaa tgagtggtca ggatatagcg ggagttttgt tcagcatcca gaactaacag     1260
ggctggattg tataagacct tgcttctggg ttgaactaat cagagggcga cccaaagaga     1320
acacaatctg gactagcggg agcagcatat cctttgtgg tgtaaacagt gacactgtgg     1380
gttggtcttg gccagacggt gctgagttgc catttaccat tgacaagtaa tttgttcaaa     1440
aaactccttg tttctact                                                  1458

<210> SEQ ID NO 28
<211> LENGTH: 1027
<212> TYPE: DNA
<213> ORGANISM: Influenza A virus

<400> SEQUENCE: 28
agcaaaagca ggtagatatt gaaagatgag tcttctaacc gaggtcgaaa cgtacgtact       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggaacgggg atccaaataa      300
catggacaaa gcagttaaac tgtataggaa gctcaagagg gagataacat tccatggggc      360
caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaatccact      540
aatcagacat gagaacagaa tggttttagc cagcactaca gctaaggcta tggagcaaat      600
ggctggatcg agtgagcaag cagcagaggc catggaggtt gctagtcagg ctagacaaat      660
ggtgcaagcg atgagaacca ttgggactca tcctagctcc agtgctggtc tgaaaaatga      720
tcttcttgaa aatttgcagg cctatcagaa acgaatgggg gtgcagatgc aacggttcaa      780
gtgatcctct cactattgcc gcaaatatca ttgggatctt gcacttgaca ttgtggattc      840
ttgatcgtct ttttttcaaa tgcatttacc gtcgctttaa atacggactg aaaggagggc      900
cttctacgga aggagtgcca aagtctatga gggaagaata tcgaaaggaa cagcagagtg      960
ctgtggatgc tgacgatggt catttttgtca gcatagagct ggagtaaaaa actaccttgt     1020
ttctact                                                              1027

<210> SEQ ID NO 29
<211> LENGTH: 1470
<212> TYPE: DNA
<213> ORGANISM: Artificial Sequence
```

<220> FEATURE:
<223> OTHER INFORMATION: Description of Artificial Sequence: Synthetic
    polynucleotide

<400> SEQUENCE: 29

```
atgcattagt tattaatagt aatcaattac ggggtcatta gttcatagcc catatatgga      60
gttccgcgtt acataactta cggtaaatgg cccgcctggc tgaccgccca acgaccccg      120
cccattgacg tcaataatga cgtatgttcc catagtaacg ccaataggga ctttccattg     180
acgtcaatgg gtggagtatt tacggtaaac tgcccacttg gcagtacatc aagtgtatca     240
tatgccaagt acgcccccta ttgacgtcaa tgacggtaaa tggcccgcct ggcattatgc     300
ccagtacatg accttatggg actttcctac ttggcagtac atctacgtat tagtcatcgc     360
tattaccatg gtgatgcggt tttggcagta catcaatggg cgtggatagc ggtttgactc     420
acggggattt ccaagtctcc accccattga cgtcaatggg agtttgtttt ggcaccaaaa     480
tcaacgggac tttccaaaat gtcgtaacaa ctccgcccca ttgacgcaaa tgggcggtag     540
gcgtgtacgg tgggaggtct atataagcag agctggttta gtgaaccgtc agatccgcta     600
gcgattacgc caagctcgaa attaaccctc actaaaggga acaaaagctg gagctccact     660
gtggaattcg cccttggccg ccatgagtct tctaaccgag gtcgaaacgc ctatcagaaa     720
cgaatggggg tgcagatgca acggttcaag tgatcctctc actattgccg caaatatcat     780
tgggatcttg cacttgacat tgtggattct tgatcgtctt tttttcaaat gcatttaccg     840
tcgctttaaa tacggactga aaggagggcc ttctacggaa ggagtgccaa agtctatcag     900
ggaagaatat cgaaaggaac agcagagtgc tgtggatgct gacgatggtc attttgtcag     960
catagagctg gagtaatagg ccaagggcga attccacatt gggctcgagg gggggcccgg    1020
taccttaatt aattaaggta ccaggtaagt gtacccaatt cgccctatag tgagtcgtat    1080
tacaattcac tcgatcggct cgctgatcag cctcgactgt gccttctagt tgccagccat    1140
ctgttgtttg cccctccccc gtgccttcct tgacccctgga aggtgccact cccactgtcc    1200
tttcctaata aaatgaggaa attgcatcgc attgtctgag taggtgccat tctattctgg    1260
ggggtggggt ggggcaggac agcaagggg aggattggga agacaatagc aggcatgctg     1320
gggaacgcgt aaattgtaag cgttaatatt ttgttaaaat tcgcgttaaa ttttttgttaa    1380
atcagctcat tttttaacca ataggccgaa atcggcaaaa tcccttataa atcaaaagaa    1440
tagaccgaga tagggttgag tgttgttcca                                      1470
```

<210> SEQ ID NO 30
<211> LENGTH: 594
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 30

```
atgcattagt tattaatagt aatcaattac ggggtcatta gttcatagcc catatatgga      60
gttccgcgtt acataactta cggtaaatgg cccgcctggc tgaccgccca acgaccccg      120
cccattgacg tcaataatga cgtatgttcc catagtaacg ccaataggga ctttccattg     180
acgtcaatgg gtggagtatt tacggtaaac tgcccacttg gcagtacatc aagtgtatca     240
tatgccaagt acgcccccta ttgacgtcaa tgacggtaaa tggcccgcct ggcattatgc     300
ccagtacatg accttatggg actttcctac ttggcagtac atctacgtat tagtcatcgc     360
```

```
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agat          594
```

<210> SEQ ID NO 31
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ttatgcccag tacatgacct tatgggactt tcctacttgg cagtacatct acgtattagt     60
catcgctatt accatggtga tgcggttttg gcagtacatc aatgggcgtg gatagcggtt    120
tgactcacgg ggatttccaa gtctccaccc cattgacgtc aatgggagtt tgttttggca    180
ccaaaatcaa cgggactttc caaaatgtcg taacaactcc gccccattga cgcaaatggg    240
cggtaggcgt gtacggtggg aggtctatat aagcagagct ggtttagtga accgtcagat    300
ccgctagcga ttacgccaag ctcgaaatta accctcacta aagggaacaa agctggagc    360 tccactgtgg aattcgccct ggccgccat gagtcttcta accgaggtcg aaacgcctat    420
cagaaacgaa tggggtgca gatgcaacgg ttcaagtgat cctctcacta ttgccgcaaa    480
tatcattggg atcttgcact tgacattgtg gattcttgat cgtctttttt tcaaatgcat    540
ttaccgtcgc tttaaatacg gactgaaagg agggccttct acgaaggag tgccaaagtc    600 tatcagggaa gaatatcgaa aggaacagca gagtgctgtg gatgctgacg atggtcattt    660
tgtcagcata gagctggagt aataggccaa gggcgaattc cacattgggc tcgaggggg    720 gcccggtacc t                                                          731
```

<210> SEQ ID NO 32
<211> LENGTH: 811
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
tgtggaattc gcccttggcc gccatgagtc ttctaaccga ggtcgaaacg cctatcagaa     60
acgaatgggg gtgcagatgc aacggttcaa gtgatcctct cactattgcc gcaaatatca    120
ttgggatctt gcacttgaca ttgtggattc ttgatcgtct ttttttcaaa tgcatttacc    180
gtcgctttaa atacggactg aaaggagggc cttctacgga aggagtgcca agtctatca    240 gggaagaata tcgaaaggaa cagcagagtg ctgtggatgc tgacgatggt cattttgtca    300
gcatagagct ggagtaatag gccaagggcg aattccacat tgggctcgag ggggggcccg    360
gtaccttaat taattaaggt accaggtaag tgtacccaat cgccctata gtgagtcgta    420 ttacaattca ctcgatcggc tcgctgatca gcctcgactg tgccttctag ttgccagcca    480
tctgttgttt gccccctccc cgtgccttcc ttgaccctgg aaggtgccac tcccactgtc    540
ctttcctaat aaaatgagga aattgcatcg cattgtctga gtaggtgcca ttctattctg    600
gggggtgggg tggggcagga cagcaagggg gaggattggg aagacaatag caggcatgct    660
ggggaacgcg taaattgtaa gcgttaatat tttgttaaaa ttcgcgttaa attttgtta    720
```

-continued

```
aatcagctca tttttttaacc aataggccga aatcggcaaa atcccttata aatcaaaaga    780
atagaccgag atagggttga gtgttgttcc a                                   811

<210> SEQ ID NO 33
<211> LENGTH: 294
<212> TYPE: DNA
<213> ORGANISM: Influenza A virus

<400> SEQUENCE: 33
atgagtcttc taaccgaggt cgaaacgcct atcagaaacg aatggggtg cagatgcaac      60 ggttcaagtg atcctctcac tattgccgca aatatcattg ggatcttgca cttgacattg   120
tggattcttg atcgtctttt tttcaaatgc atttaccgtc gctttaaata cggactgaaa   180
ggagggcctt ctacggaagg agtgccaaag tctatcaggg aagaatatcg aaaggaacag   240
cagagtgctg tggatgctga cgatggtcat tttgtcagca tagagctgga gtaa         294
```

INFLUENZA VIRUS MUTANTS AND USES THEREFOR

CROSS-REFERENCE TO RELATED APPLICATIONS

This application is a continuation of U.S. patent application Ser. No. 15/917,926, filed Mar. 12, 2018, which is a continuation of U.S. patent application Ser. No. 15/040,277, filed Feb. 10, 2016, now U.S. Pat. No. 9,919,042, issued Mar. 20, 2018, which is a continuation of U.S. patent application Ser. No. 14/128,415, filed Jan. 7, 2014, now U.S. Pat. No. 9,284,533, issued Mar. 15, 2016, which is the U.S. 371 National Stage Application of PCT International Application No.: PCT/US2012/043606, filed Jun. 21, 2012, which claims the benefit of U.S. Provisional Application No. 61/501,034, filed Jun. 24, 2011, the contents of which are incorporated herein by reference in their entireties.

BACKGROUND

Influenza is a leading cause of death among American adults. Each year, about 36,000 people die from influenza, and more than 200,000 people are hospitalized. Influenza is a highly contagious disease that is spread by coughing, sneezing and through direct physical contact with objects that carry the virus such as doorknobs and telephones. Symptoms of influenza include fever, extreme fatigue, headache, chills and body aches; about 50 percent of infected people have no symptoms but are still contagious. Immunization is 70-90 percent effective in preventing influenza in healthy people under the age of 65, as long as the antigenicities of the circulating virus strain match those of the vaccine.

Vaccination is the main method for preventing influenza, and both live attenuated and inactivated (killed) virus vaccines are currently available. Live virus vaccines, typically administered intranasally, activate all phases of the immune system and can stimulate an immune response to multiple viral antigens. Thus, the use of live viruses overcomes the problem of destruction of viral antigens that may occur during preparation of inactivated viral vaccines. In addition, the immunity produced by live virus vaccines is generally more durable, more effective, and more cross-reactive than that induced by inactivated vaccines, and live virus vaccines are less costly to produce than inactivated virus vaccines. However, the mutations in attenuated virus are often ill-defined, and reversion is a concern.

SUMMARY

In one aspect, the present disclosure provides a nucleic acid sequence comprising SEQ ID NO:1.

In one aspect, the present disclosure provides a nucleic acid sequence comprising SEQ ID NO:2.

In one aspect, the present disclosure provides a nucleic acid sequence comprising SEQ ID NO:3.

In one aspect, the present disclosure provides a composition comprising SEQ ID NO:1, SEQ ID NO:2 or SEQ ID NO: 3, operably linked to (i) a promoter, and (ii) a transcription termination sequence.

In one aspect, the present disclosure provides a recombinant influenza virus comprising a mutation in the M gene. In some embodiments, the recombinant influenza virus comprises SEQ ID NO:1, SEQ ID NO:2, or SEQ ID NO: 3. In some embodiments, the mutation in the M gene results in failure of the virus to express the M2 protein, or causes the virus to express a truncated M2 protein having the amino acid sequence of SEQ ID NO:4. In some embodiments, the mutation in the M gene does not revert to wild-type or to a non-wild-type sequence encoding a functional M2 protein for at least 10 passages in an in vitro host cell system. In some embodiments, the virus is an influenza A virus. In some embodiments, the virus is non-pathogenic in a mammal infected with the virus. In some embodiments, the in vitro cell system comprises Chinese Hamster Ovary cells. In some embodiments, the in vitro cell system comprises Vero cells.

In one aspect, the present disclosure provides a cell comprising the recombinant influenza virus of any one of claims 5-10. In some embodiments, the cell is in vitro. In some embodiments, the cell is in vivo.

In one aspect, the present disclosure provides a composition comprising: a recombinant influenza virus comprising a mutation in the M gene. In some embodiments, the composition comprises SEQ ID NO:1, SEQ ID NO: 2, or SEQ ID NO:3. In some embodiments, the mutation in the M gene results in failure of the virus to express the M2 protein, or causes the virus to express a truncated M2 protein having the amino acid sequence of SEQ ID NO:4. In some embodiments, the virus is an influenza A virus. In some embodiments, the composition is non-pathogenic to a mammal administered the composition. In some embodiments, the composition elicits a detectable immune response in a mammal within about three weeks after administration of the composition to the mammal.

In one aspect, the present disclosure provides a vaccine comprising: a recombinant influenza virus comprising a mutation in the M gene. In some embodiments, the vaccine comprises SEQ ID NO:1, SEQ ID NO:2, or SEQ ID NO: 3. In some embodiments, the mutation in the M gene results in failure of the virus to express the M2 protein, or causes the virus to express a truncated M2 protein having the amino acid sequence of SEQ ID NO:4. In some embodiments, the virus is an influenza A virus. In some embodiments, the vaccine is non-pathogenic to a mammal administered the vaccine. In some embodiments, the vaccine elicits a detectable immune response in a mammal within about three weeks after administration of the vaccine to the mammal. In some embodiments, the vaccine comprises at least two different influenza viral strains in addition to the recombinant virus. In some embodiments, the vaccine comprises at least one influenza B virus or influenza B virus antigen. In some embodiments, the vaccine comprises at least one influenza C virus or influenza C virus antigen. In some embodiments, the vaccine comprises one or more viruses or viral antigens comprising human influenza A and pandemic influenza viruses from non-human species. In some embodiments, the vaccine comprises the human influenza A virus is selected from the group comprising H1N1, H2N2 and H3N2.

In one aspect, the present disclosure provides a method for propagating a recombinant influenza virus, comprising: contacting a host cell with a recombinant influenza virus SEQ ID NO:1, SEQ ID NO:2 or SEQ ID NO: 3; incubating the host cell for a sufficient time and under conditions suitable for viral replication, and isolating progeny virus particles.

In one aspect, the present disclosure provides a method of preparing a vaccine, comprising: placing a host cell in a bioreactor; contacting the host cell with a recombinant virus SEQ ID NO:1, SEQ ID NO:2 or SEQ ID NO: 3; incubating the host cell for a sufficient time and under conditions suitable for viral propagation; isolating the progeny virus particles; and formulating the progeny virus particles for administration as a vaccine.

In one aspect, the present disclosure provides a method for immunizing a subject, comprising: administering a composition comprising a recombinant influenza virus comprising mutation in the M gene, wherein the mutation in the M gene results in failure of the virus to express the M2 protein, or causes the virus to express a truncated M2 protein having the amino acid sequence of SEQ ID NO:4.

In one aspect, the present disclosure provides a method for reducing the likelihood or severity of infection by influenza A virus in a subject comprising: administering a composition comprising a recombinant influenza virus comprising mutation in the M gene, wherein the mutation in the M gene results in failure of the virus to express the M2 protein, or causes the virus to express a truncated M2 protein having the amino acid sequence of SEQ ID NO:4. In some embodiments, the recombinant influenza virus comprises SEQ ID NO:1, SEQ ID NO:2, or SEQ ID NO:3. In some embodiments, the method comprises providing at least one booster dose of the composition, wherein the at least one booster dose is provided at three weeks after a first administration. In some embodiments, the method comprises administering the composition intranasally, intramuscularly or intracutaneously. In some embodiments, the method comprises administering is performed intracutaneously. In some embodiments, the method comprises administering is performed using a microneedle delivery device.

In one aspect, the present disclosure provides a method for intracutaneous administration of an immunogenic composition comprising: (a) providing a microneedle delivery device comprising (i) a puncture mechanism; (ii) an immunogenic composition layer comprising a plurality of microneedles capable of puncturing skin and allowing an immunogenic composition to be administered intracutaneously; and (b) depressing the puncture mechanism; wherein the immunogenic composition comprises a recombinant influenza virus comprising a mutation in the M gene, and wherein the mutation in the M gene results in failure of the virus to express the M2 protein, or causes the virus to express a truncated M2 protein having the amino acid sequence of SEQ ID NO:4. In some embodiments, the recombinant influenza virus comprises SEQ ID NO:1, SEQ ID NO:2, or SEQ ID NO:3. In some embodiments, the microneedle array is initially positioned inside of a device housing, and upon actuation of a lever allows the microneedles to extend through the device bottom and insert into the skin thereby allowing infusion of the vaccine fluid into the skin.

In one aspect, the present disclosure provides a recombinant influenza virus comprising a mutation in the M gene, wherein the virus does not replicate in an unmodified host cell selected from the group consisting of a Chinese Hamster Ovary (CHO) cell, a Vero cell, a or Madin-Darby canine kidney cell. In some embodiments, the mutation in the M gene results in failure of the virus to express the M2 protein, or causes the virus to express a truncated M2 protein having the amino acid sequence of SEQ ID NO:4.

In one aspect, the present disclosure provides a recombinant cell comprising a nucleic acid encoding an influenza virus M2 ion channel gene, wherein the nucleic acid is expressed in the cell.

In one aspect, the present disclosure provides a recombinant cell comprising a 2,6-sialic acid receptor gene.

In one aspect, the present disclosure provides a recombinant cell comprising a cellular genome or an expression vector that expresses (i) a viral M2 ion channel gene, and (ii) a 2,6-sialic acid receptor gene. In some embodiments, the cell is a eukaryotic cell. In some embodiments, the eukaryotic cell is a Chinese Hamster Ovary cell or a Vero cell. In some embodiments, the recombinant cell further comprises a human influenza virus, wherein the virus does not express a functional M2 protein.

In one aspect, the present disclosure provides a method for producing recombinant influenza viral particles, comprising (A) infecting the cell of one of claims 47-52 with human influenza virus, wherein the cell either (i) constitutively expresses the functional M2 ion channel protein, or (ii) is induced after viral infection to express the functional M2 ion channel protein, and wherein the virus successfully replicates only in the presence of the functional M2 ion channel proteins expressed by the cell; and (B) isolating the progeny virus particles. In some embodiments, the method further comprises formulating the isolated viral particles into a vaccine. In some embodiments, the virus comprises a human influenza virus, and wherein the virus does not express a functional M2 protein.

BRIEF DESCRIPTION OF THE DRAWINGS

FIG. 3 shows the nucleotide sequence of unprocessed M1 and M2.

FIG. 28A shows serum IgG and IgA titers following administration of PR8, M2KO($\Delta$TM), inactivated PR8 (IN, IM), or PBS. FIG. 28B shows lung wash IgG and IgA titers following administration of PR8, M2KO($\Delta$TM), inactivated PR8 (IN, IM), or PBS.

FIG. 29A shows mouse body weight change following homologous PR8 (H1N1) challenge. FIG. 29B shows mouse survival following heterologous Aichi (H3N2) challenge.

FIG. 30A shows viral titers following PR8 (H1N1) challenge. FIG. 30B shows viral titers following Aichi (H3N2) challenge.

FIG. 34A shows serum viral titers in animals administered FluMist® H3, M2KO($\Delta$TM) H3, IVR-147, and PBS. FIG. 34B shows lung wash viral titers in animals administered FluMist® H3, M2KO($\Delta$TM) H3, IVR-147, and PBS. FIG. 34C shows nasal turbinate viral titiers in animals administered FluMist® H3, M2KO($\Delta$TM) H3, IVR-147, and PBS.

FIG. 35A shows body weight loss following Aichi challenge in animals administered FluMist® H3, M2KO($\Delta$TM) H3, IVR-147, and PBS. FIG. 35B shows the percent survival following Aichi challenge of animals administered FluMist® H3, M2KO($\Delta$TM) H3, IVR-147, and PBS.

FIG. 38 is a chart showing that M2KO($\Delta$TM) virus does not replicate in respiratory tract of mice.

Figure 44A:
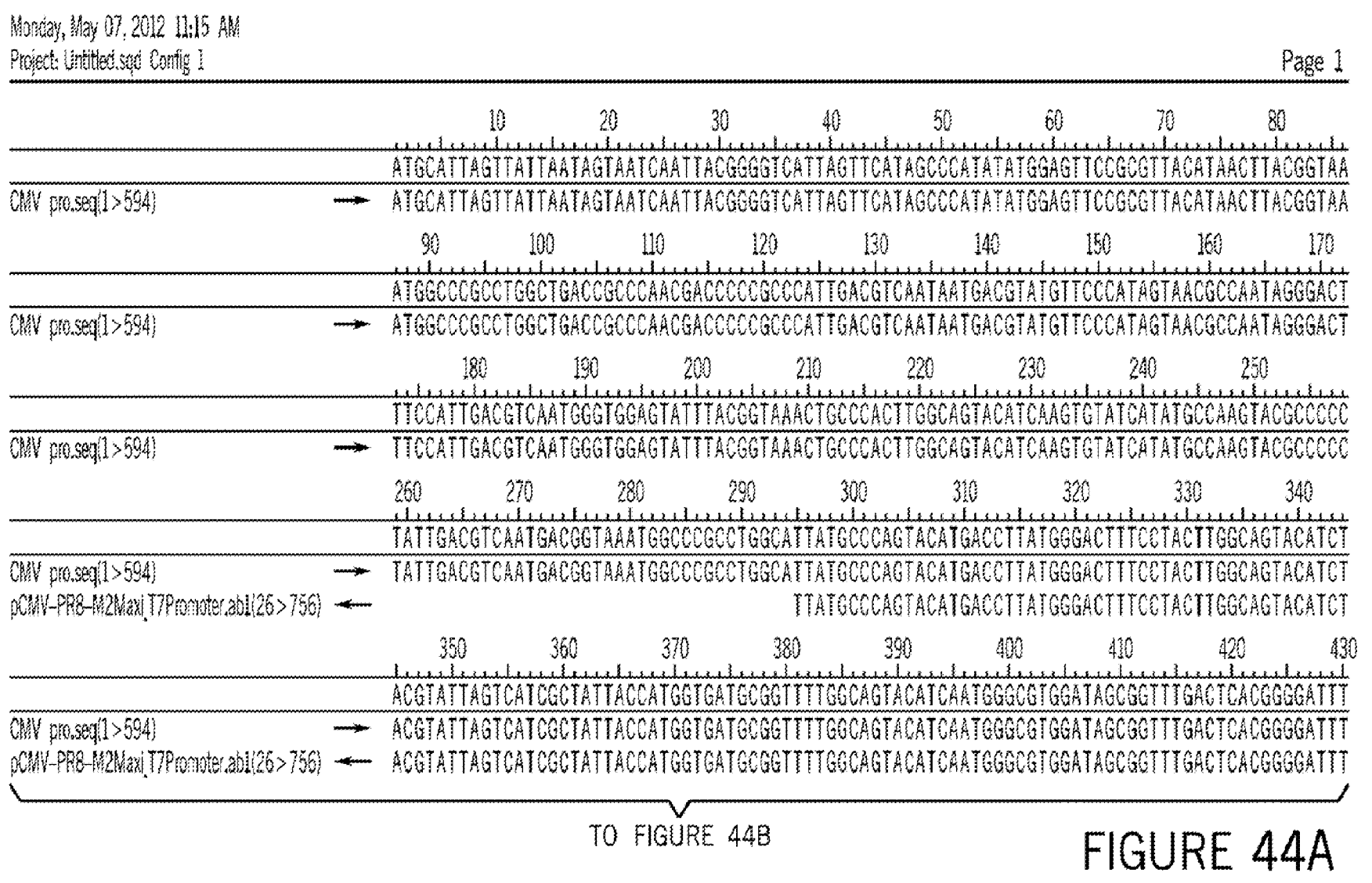
Figure 44B:
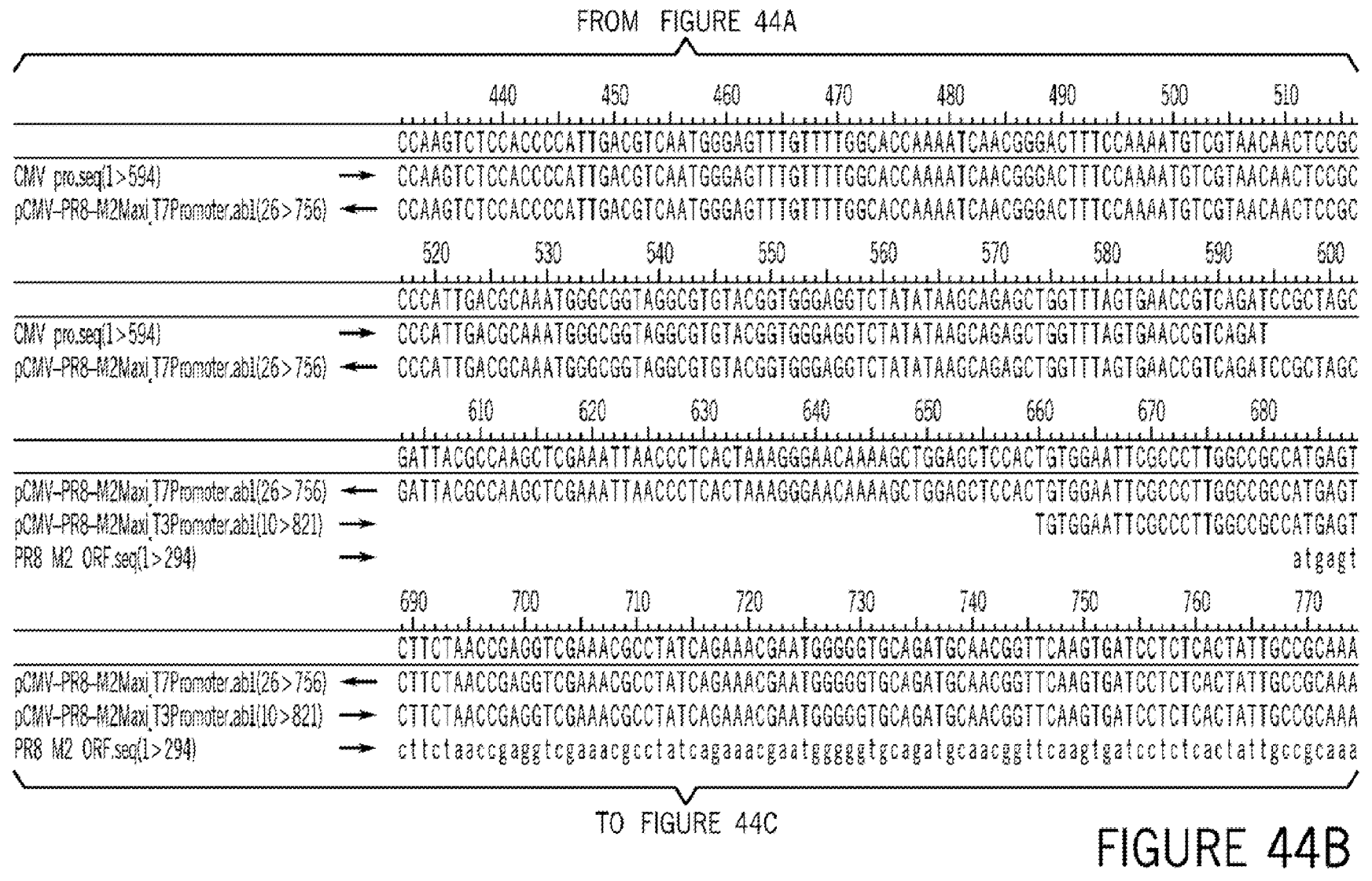
Figure 44C:
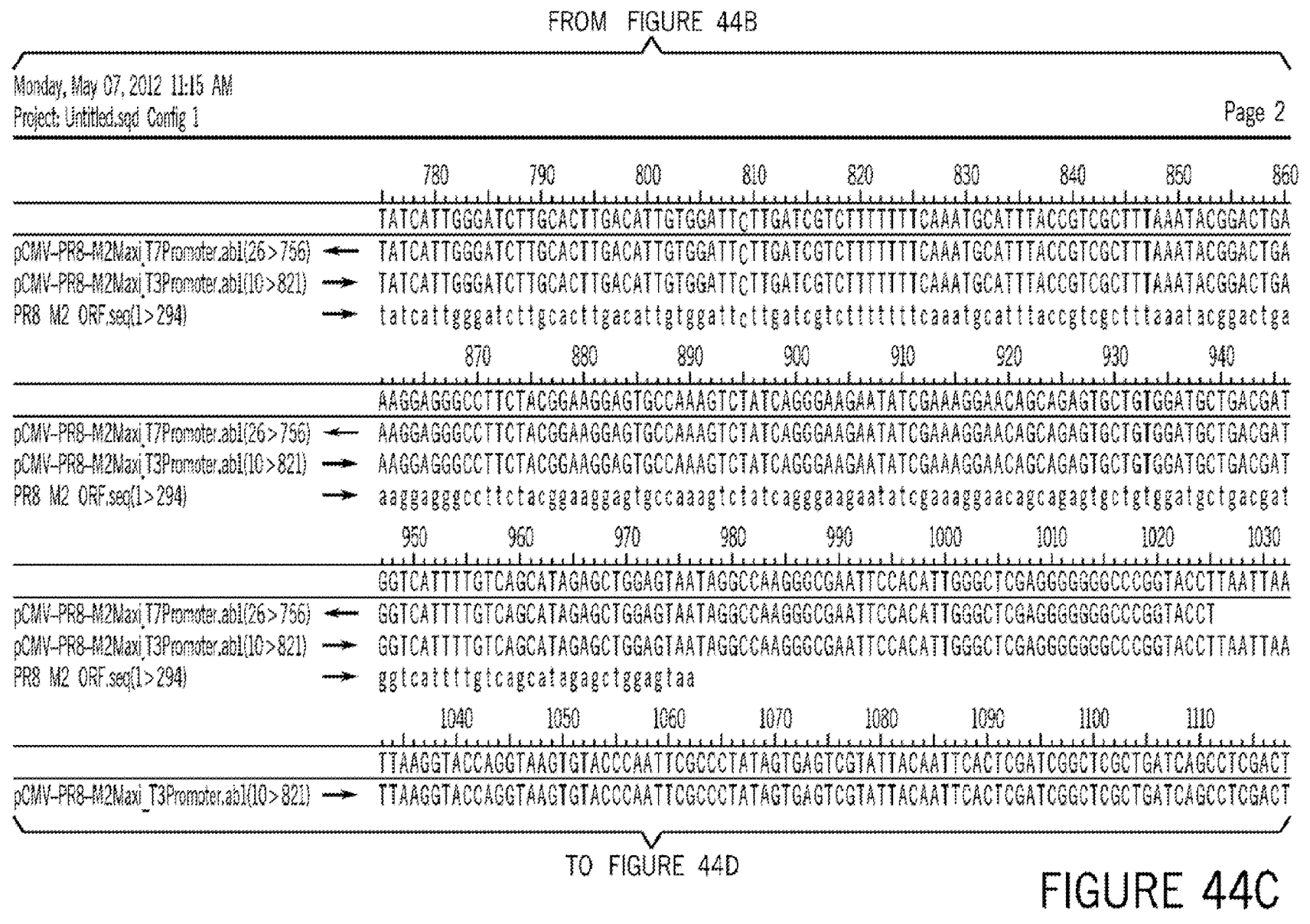
Figure 44D:
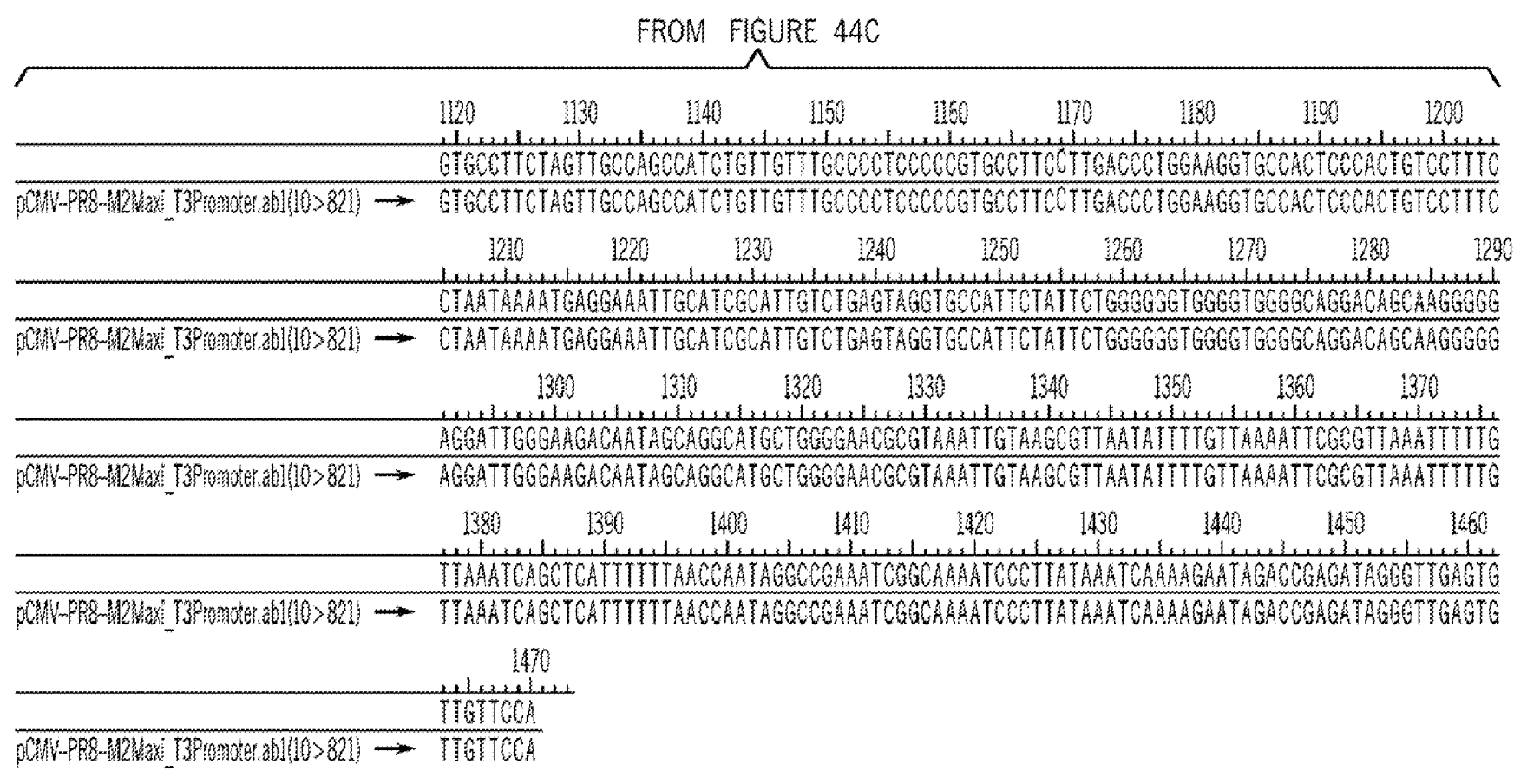

FIGS. 44A, 44B, 44C, and 44D are charts showing a sequence alignment of pCMV-PR8-M2 to the open reading frame of the influenza M2 gene.

FIGS. 49A and 49B are charts showing a summary of ELISA IgG titers in ferret sera from vaccination with M2KO(ΔTM) or FluMist® to post-challenge.

FIG. 50 is a chart showing viral titers in nasal washes from ferrets in transmission study. M2KO(ΔTM) virus did not transmit (no virus detected), whereas the control Brisb/10 virus did transmit.

FIG. 53 is a chart showing viral titers in guinea pigs inoculated with FluLaval: A/California/7/2009 NYMC X-181, A/Victoria/210/2009 NYMC X-187 (an A/Perth/16/2009-like virus), and B/Brisbane/60/2008 by intramuscular (IM) and intradermal (ID) delivery at 0, 30, and 60 days post-inoculation.

Figure 1:
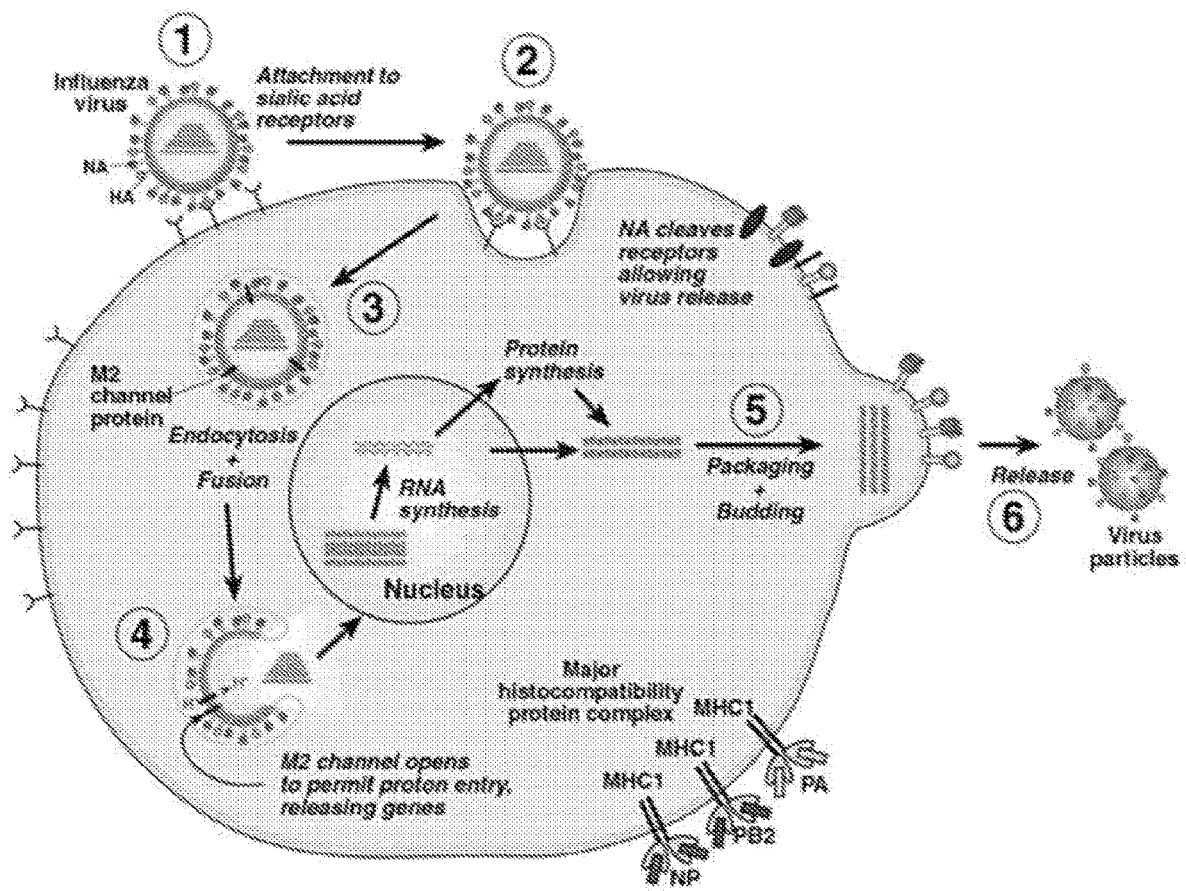
FIG. 1 is a graphic depicting the role of M2 ion channel in an influenza virus life cycle, wherein (1) the influenza virus attaches to sialic acid receptors on a cell surface; (2) the virus is internalized into the cell; (3) the M2 ion channel is expressed on the viral surface; (4) the M2 ion channel opens to permit proton entry, leading to a release of viral RNA that enters the nucleus, is replicated and results in viral protein synthesis; and (5) the viral components are packaged into virions and released.

DETAILED DESCRIPTION

I. Definitions

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" and "patient" are used interchangeably and refer to an animal, for example, a member of any vertebrate species. The methods and compositions of the presently disclosed subject matter are particularly useful for warm-blooded vertebrates including mammals and birds. Exemplary subjects may include mammals such as humans, as well as mammals and birds of importance due to being endangered, of economic importance (animals raised on farms for consumption by humans) and/or of social importance (animals kept as pets or in zoos) to humans. In some embodiments, the subject is a human. In some embodiments, the subject is not human.

As used herein, the terms "effective amount" or "therapeutically effective amount" or "pharmaceutically effective amount" refer to a quantity sufficient to achieve a desired therapeutic and/or prophylactic effect, e.g., an amount which results in the prevention of, disease, condition and/or symptom(s) thereof. In the context of therapeutic or prophylactic applications, the amount of a composition administered to the subject will depend on the type and severity of the disease and on the characteristics of the individual, such as general health, age, sex, body weight and tolerance to the composition drugs. It will also depend on the degree, severity and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., immunogenic compositions, such as vaccines) are administered.

As used herein, the terms "isolated" and/or "purified" refer to in vitro preparation, isolation and/or purification of a nucleic acid (e.g., a vector or plasmid), polypeptide, virus or cell such that it is not associated with unwanted in vivo substances, or is substantially purified from unwanted in vivo substances with which it normally occurs. For example, in some embodiments, an isolated virus preparation is obtained by in vitro culture and propagation, and is substantially free from other infectious agents. As used herein, "substantially free" means below the level of detection for a particular compound, such as unwanted nucleic acids, proteins, cells, viruses, infectious agents, etc. using standard detection methods for that compound or agent.

As used herein the term "recombinant virus" refers to a virus that has been manipulated in vitro, e.g., using recombinant nucleic acid techniques, to introduce changes to the viral genome and/or to introduce changes to the viral proteins. For example, in some embodiments, recombinant viruses may include both wild-type, endogenous, nucleic acid sequences and mutant and/or exogenous nucleic acid sequences. Additionally or alternatively, in some embodiments, recombinant viruses may include modified protein components, such as mutant or variant matrix, hemagglutinin, neuraminidase, nucleoprotein, non-structural and/or polymerase proteins.

As used herein the term "recombinant cell" or "modified cell" refer to a cell that has been manipulated in vitro, e.g., using recombinant nucleic acid techniques, to introduce nucleic acid into the cell and/or to modify cellular nucleic acids. Examples of recombinant cells includes prokaryotic or eukaryotic cells carrying exogenous plasmids, expression vectors and the like, and/or cells which include modifications to their cellular nucleic acid (e.g., substitutions, mutations, insertions, deletions, etc., into the cellular genome). An exemplary recombinant cell is one which has been manipulated in vitro to express an exogenous protein, such as a viral M2 protein.

As used herein the terms "mutant," "mutation," and "variant" are used interchangeably and refer to a nucleic acid or polypeptide sequence which differs from a wild-type sequences. In some embodiments, mutant or variant sequences are naturally occurring. In other embodiments, mutant or variant sequence are recombinantly and/or chemically introduced. In some embodiments, nucleic acid mutations include modifications (e.g., additions, deletions, substitutions) to RNA and/or DNA sequences. In some embodiments, modifications include chemical modification (e.g., methylation) and may also include the substitution or addition of natural and/or non-natural nucleotides. Nucleic acid mutations may be silent mutations (e.g., one or more nucleic acid changes which code for the same amino acid as the wild-type sequence) or may result in a change in the encoded amino acid, result in a stop codon, or may introduce splicing defects or splicing alterations. Nucleic acid mutations to coding sequences may also result in conservative or non-conservative amino acid changes.

As used herein, the term "vRNA" refers to the RNA comprising a viral genome, including segmented or non-segmented viral genomes, as well as positive and negative strand viral genomes. vRNA may be wholly endogenous and "wild-type" and/or may include recombinant and/or mutant sequences.

As used herein, the term "host cell" refers to a cell in which a pathogen, such as a virus, can replicate. In some embodiments, host cells are in vitro, cultured cells (e.g., CHO cells, Vero cells, MDCK cells, etc.) Additionally or alternatively, in some embodiments, host cells are in vivo (e.g., cells of an infected vertebrate, such as an avian or mammal). In some embodiments, the host cells may be modified, e.g., to enhance viral production such as by enhancing viral infection of the host cell and/or by enhancing viral growth rate. By way of example, but not by way of limitation, exemplary host cell modifications include recombinant expression of 2-6-linked sialic acid receptors on the cell surface of the host cell, and/or recombinant expression of a protein in the host cells that has been rendered absent or ineffective in the pathogen or virus.

As used herein, the term "infected" refers to harboring a disease or pathogen, such as a virus. An infection can be intentional, such as by administration of a virus or pathogen (e.g., by vaccination), or unintentional, such as by natural transfer of the pathogen from one organism to another, or from a contaminated surface to the organism.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus. This is in contrast to killed or completely inactivated virus.

As used herein, the term "type" and "strain" as used in conjunction with a virus are used interchangeably, and are used to generally refer to viruses having different characteristics. For example, influenza A virus is a different type of virus than influenza B virus. Likewise, influenza A H1N1 is a different type of virus than influenza A H2N1, H2N2 and H3N2. Additionally or alternatively, in some embodiments, different types of virus such as influenza A H2N1, H2N2 and H3N2 may be termed "subtypes."

As used herein, "M2KO" or "M2KO(ΔTM)" refers to SEQ ID NO:1, a virus comprising SEQ ID NO:1, or a vaccine comprising a virus comprising SEQ ID NO:1, depending on the context in which it is used. For example, in describing mutations of the M2 gene demonstrated herein, "M2KO" or "M2KO(ΔTM)" refers to SEQ ID NO:1. When describing the viral component of a vaccine, "M2KO" or "M2KO(ΔTM)" refers to a recombinant influenza virus which possesses internal 6 genes of PR8 (nucleoprotein (NP), polymerase genes (PA, PB1, PB2), non-structural (NS), matrix (M)), but which does not express functional M2 protein. When describing a vaccine, "M2KO" or "M2KO(ΔTM)" refers to a vaccine comprising the M2KO (ΔTM) recombinant virus.

As used herein, "M2KO(ΔTM) virus" encompasses a recombinant influenza virus which possesses internal 6 genes of PR8 (nucleoprotein (NP), polymerase genes (PA, PB1, PB2), non-structural (NS), matrix (M)), but which does not express functional M2 protein, alone or in combination with other viral components and/or genes encoding other viral components. In some embodiments, the M2KO(ΔTM) virus comprises genes of other influenza viruses. In some embodiments, the virus comprises the HA and NA genes of Influenza A/Brisbane/10/2007-like A/Uruguay/716/2007 (H3N2). In some embodiments, the M2KO(ΔTM) virus comprises the HA and NA genes of the A/Vietnam/1203/2004 (H5N1) virus. In some embodiments, the M2KO (ΔTM) virus comprises the HA and NA genes of the A/California/07/2009 (CA07) (H1N1pdm) virus.

II. Influenza A Virus

A. General

Influenza is a leading cause of death among American adults. The causal agent of influenza are viruses of the family orthomyxoviridae including influenza A virus, influenza B virus and influenza C virus, with influenza A being the most common and most virulent in humans.

The influenza A virus is an enveloped, negative-strand RNA virus. The genome of influenza A virus is contained on eight single (non-paired) RNA strands the complements of which code for eleven proteins (HA, NA, NP, M1, M2, NS1, NEP, PA, PB1, PB1-F2, PB2). The total genome size is about 14,000 bases. The segmented nature of the genome allows for the exchange of entire genes between different viral strains during cellular cohabitation. The eight RNA segments are as follows. 1) HA encodes hemagglutinin (about 500 molecules of hemagglutinin are needed to make one virion); 2) NA encodes neuraminidase (about 100 molecules of neuraminidase are needed to make one virion); 3) NP encodes nucleoprotein; 4) M encodes two proteins (the M1 and the M2) by using different reading frames from the same RNA segment (about 3000 M1 molecules are needed to make one virion); 5) NS encodes two proteins (NS1 and NEP) by using different reading frames from the same RNA segment; 6) PA encodes an RNA polymerase; 7) PB1 encodes an RNA polymerase and PB1-F2 protein (induces apoptosis) by using different reading frames from the same RNA segment; 8) PB2 encodes an RNA polymerase.

There are several subtypes of influenza A, named according to an H number (for the type of hemagglutinin) and an N number (for the type of neuraminidase). Currently, there are 16 different H antigens known (H1 to H16) and nine different N antigens known (N1 to N9). Each virus subtype has mutated into a variety of strains with differing pathogenic profiles; some pathogenic to one species but not others, some pathogenic to multiple species. Exemplary Influenza A virus subtypes that have been confirmed in humans, include, but are not limited to H1N1 which caused the "Spanish Flu" and the 2009 swine flu outbreak; H2N2 which caused the "Asian Flu" in the late 1950s; H3N2 which caused the Hong Kong Flu in the late 1960s; H5N1, considered a global influenza pandemic threat through its spread in the mid-2000s; H7N7; H1N2 which is currently endemic in humans and pigs; and H9N2, H7N2, H7N3, H5N2, H10N7.

Some influenza A variants are identified and named according to the known isolate to which they are most similar, and thus are presumed to share lineage (e.g., Fujian flu virus-like); according to their typical host (example Human flu virus); according to their subtype (example H3N2); and according to their pathogenicity (example LP, Low Pathogenic). Thus, a flu from a virus similar to the isolate A/Fujian/411/2002(H3N2) can be called Fujian flu, human flu, and H3N2 flu.

In addition, influenza variants are sometimes named according to the species (host) the strain is endemic in or adapted to. The main variants named using this convention are: bird flu, human flu, swine influenza, equine influenza and canine influenza. Variants have also been named according to their pathogenicity in poultry, especially chickens, e.g., Low Pathogenic Avian Influenza (LPAI) and Highly Pathogenic Avian Influenza (HPAI).

B. Life Cycle and Structure

The life cycle of influenza viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell. Different viral proteins play a role in each of these steps.

The influenza A particle is made up of a lipid envelope which encapsulates the viral core. The inner side of the envelope is lined by the matrix protein (M1), while the outer surface is characterized by two types of glycoprotein spikes: hemagglutinin (HA) and neuraminidase (NA). M2, a transmembrane ion channel protein, is also part of the lipid envelope. See e.g., FIG. 1.

The HA protein, a trimeric type I membrane protein, is responsible for binding to sialyloligosaccharides (oligosaccharides containing terminal sialic acid linked to galactose) on host cell surface glycoproteins or glycolipids. This protein is also responsible for fusion between viral and host cell membranes, following virion internalization by endocytosis.

Neuraminidase (NA), a tetrameric type II membrane protein, is a sialidase that cleaves terminal sialic acid residues from the glycoconjugates of host cells and the HA and NA, and thus is recognized as receptor-destroying enzyme. This sialidase activity is necessary for efficient release of progeny virions from the host cell surface, as well as prevention of progeny aggregation due to the binding activity of viral HAs with other glycoproteins. Thus, the receptor-binding activity of the HA and the receptor-destroying activity of the NA likely act as counterbalances, allowing efficient replication of influenza.

The genome segments are packaged into the core of the viral particle. The RNP (RNA plus nucleoprotein, NP) is in helical form with three viral polymerase polypeptides associated with each segment.

The influenza virus life cycle begins with binding of the HA to sialic acid-containing receptors on the surface of the host cell, followed by receptor-mediated endocytosis. FIG. 1. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: (1) synthesis of an mRNA with a 5' cap and 3' polyA structure, (2) a full-length complementary RNA (cRNA), and (3) genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuramimidase (NA) protein plays a role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions remains largely unknown.

C. Role of the M2 Protein

Figure 2:
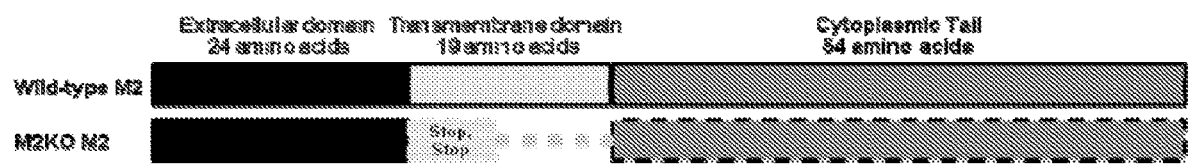
FIG. 2 is a schematic diagram of wild-type and mutant M2 genes. The M2 gene of A/Puerto Rico/8/1934 (PR8) M segment was deleted by insertion of two stop codons downstream of the open reading frame of the M1 protein followed by deletion of 51 nucleotides in the transmembrane domain to inhibit expression of full-length M2 protein.

As described above, spanning the viral membrane are three proteins: hemagglutinin (HA), neuramimidase (NA), and M2. The extracellular domains (ectodomains) of HA and NA are quite variable, while the ectodomain domain of M2 is essentially invariant among influenza A viruses. Without wishing to be bound by theory, in influenza A viruses, the M2 protein which possesses ion channel activity, is thought to function at an early state in the viral life cycle between host cell penetration and uncoating of viral RNA. Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm. In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment. It was also shown that the M2 transmembrane domain itself can function as an ion channel. M2 protein ion channel activity is thought to be essential in the life cycle of influenza viruses, because amantadine hydrochloride, which blocks M2 ion channel activity, has been shown to inhibit viral replication. However, a requirement for this activity in the replication of influenza A viruses has not been directly demonstrated. The structure of the M2 protein is shown in FIG. 2. The nucleic acid sequence of the M2 protein, along with the M1 sequence, is shown in FIG. 3.

Although influenza B and C viruses are structurally and functionally similar to influenza A virus, there are some differences. For example, influenza B virus does not have an M2 protein with ion channel activity. Instead, the NB protein, a product of the NA gene, likely has ion channel activity and thus a similar function to the influenza A virus M2 protein. Similarly, influenza C virus does not have an M2 protein with ion channel activity. However, the CM1 protein of the influenza C virus is likely to have this activity.

III. M2 Viral Mutants

In one aspect, influenza A viruses harboring a mutant M2 vRNA sequence are disclosed. Typically, such mutants do not have M2 ion channel activity, exhibit attenuated growth properties in vivo, cannot produce infectious progeny and are non-pathogenic or show reduced pathogenesis in infected subjects. The mutant viruses are immunogenic, and when used as a vaccine, provide protection against infection with a counterpart wild-type and/or other pathogenic virus. Additionally, the M2 mutants disclosed herein are stable, and do not mutate to express a functional M2 polypeptide, regardless of the host cell used. Additionally or alternatively, in some embodiments, the M1 protein of these mutants is produced without detectable alteration to its function. In some embodiments, viruses harboring the mutant M2 nucleic acid sequences can not replicate in a host cell in which a corresponding wild-type virus could be propagated. By way of example, but not by way of limitation, in some embodiments, the wild-type virus can be grown, propagated and replicate in culturing MDCK cells, CHO cells and/or Vero cells, while the corresponding virus harboring a mutant M2 sequence cannot grow, replicate or be propagated in the same type of cells.

As noted above, in some embodiments, the M2 mutant virus is stable, and does not mutate or revert to wild-type or to a non-wild-type sequence encoding a functional M2 protein in a host cell. For example, in some embodiments, the M2 mutant virus is stable for 2 passages, 3 passages, 5 passages, 10 passages, 12 passages, 15 passages, 20 passages, 25 passages or more than 25 passages in a host cell. In some embodiments, the host cell is an unmodified host cell. In other embodiments, the host cell is a modified host cell, such as a MDCK cell which expresses the M2 protein.

In some embodiments, the M2 mutants include one or more nucleic acid substitutions and/or deletions. In some embodiments, the mutations are localized in nucleic acids which code for one or more of the extracellular domain of the M2 protein, the transmembrane domain of the M2 proteins and/or the cytoplasmic tail of the M2 protein. Additionally or alternatively, in some embodiments, one or more nucleic acid mutations results in a splice variant, one or more stop codons and/or one or more amino acid deletions of the M2 peptide In some embodiments, viruses carrying the mutant M2 nucleic acid produce a non-functional M2 polypeptide. In some embodiments, viruses carrying the mutant M2 nucleic acid do not produce an M2 polypeptide. In some embodiments, viruses carrying the mutant M2 nucleic acid produce a truncated M2 polypeptide. In some embodiments, truncated M2 polypeptide has the amino acid sequence MSLLTEVETPIRNEWGCRCNGSSD.

Three exemplary, non-limiting M2 viral mutants (M2-1, M2-2 and M2-3) are provided below in Tables 1-3. In the tables, lower case letters correspond to the M2 sequence; upper case letters correspond to the M1 sequence; mutant sequence (e.g., stop codons, splice defect) are in bold, underlined. Underlined (lower case) bases in the M2-2 mutant indicate the region deleted in the M2-1 and M2-3 mutants.

TABLE 1

M2-1—(SEQ ID NO: 1) M2 ectodomain + 2 stop codons + TM deletion (PR8 M segment + 2 stops (786-791) without 792-842 (TM)); also known as "M2KOTMdel," "M2KOATM."

3'AGCAAAAGCAGGTAGATATTGAAAGatgagtcttctaaccgaggtc gaaacGTACGTACTCTCTATCATCCCGTCAGGCCCCCTCAAAGCCGAG

TABLE 1-continued

M2-1—(SEQ ID NO: 1) M2 ectodomain + 2 stop codons + TM deletion (PR8 M segment + 2 stops (786-791) without 792-842 (TM)); also known as "M2KOTMdel," "M2KOATM."

ATCGCACAGAGACTTGAAGATGTCTTTGCAGGGAAGAACACCGATCTT

GAGGTTCTCATGGAATGGCTAAAGACAAGACCAATCCTGTCACCTCTG

ACTAAGGGGATTTTAGGATTTGTGTTCACGCTCACCGTGCCCAGTGAG

CGAGGACTGCAGCGTAGACGCTTTGTCCAAAATGCCCTTAATGGGAAC

GGGGATCCAAATAACATGGACAAAGCAGTTAAACTGTATAGGAAGCTC

AAGAGGGAGATAACATTCCATGGGGCCAAAGAAATCTCACTCAGTTAT

TCTGCTGGTGCACTTGCCAGTTGTATGGGCCTCATATACAACAGGATG

GGGGCTGTGACCACTGAAGTGGCATTTGGCCTGGTATGTGCAACCTGT

GAACAGATTGCTGACTCCCAGCATCGGTCTCATAGGCAAATGGTGACA

ACAACCAATCCACTAATCAGACATGAGAACAGAATGGTTTTAGCCAGC

ACTACAGCTAAGGCTATGGAGCAAATGGCTGGATCGAGTGAGCAAGCA

GCAGAGGCCATGGAGGTTGCTAGTCAGGCTAGACAAATGGTGCAAGCG

ATGAGAACCATTGGGACTCATCCTAGCTCCAGTGCTGGTCTGAAAAAT

GATCTTCTTGAAAATTTGCAGgcctatcagaaacgaatgggggtgcag atgcaacggttcaagtgatTAATAGgatcgtattttttcaaatgcat ttaccgtcgctttaaatacggactgaaaggagggccttctacggaagg agtgccaaagtctatgagggaagaatatcgaaaggaacagcagagtgc tgtggatgctgacgatggtcattttgtcagcatagagctggagtaaAA

AACTACCTTGTTTCTACT

The M2 polypeptide sequence produced from this mutant is as follows:

(SEQ ID NO: 4)
MSLLTEVETPIRNEWGCRCNGSSD.

TABLE 2

M2-2—SEQ ID NO: 2 M2 ectodomain + 2 stops + splice defect (PR8 M segment + 2 stops (786-791) + splice defect nt 52) (also known as "Splice def M2KO" or "Splice def")

3'AGCAAAAGCAGGTAGATATTGAAAGatgagtatctaaccgaggtcg aaac<u>C</u>TACGTACTCTCTATCATCCCGTCAGGCCCCCTCAAAGCCGAGA

TCGCACAGAGACTTGAAGATGTCTTTGCAGGGAAGAACACCGATCTTG

AGGTTCTCATGGAATGGCTAAAGACAAGACCAATCCTGTCACCTCTGA

CTAAGGGGATTTTAGGATTTGTGTTCACGCTCACCGTGCCCAGTGAGC

GAGGACTGCAGCGTAGACGCTTTGTCCAAAATGCCCTTAATGGGAACG

GGGATCCAAATAACATGGACAAAGCAGTTAAACTGTATAGGAAGCTCA

AGAGGGAGATAACATTCCATGGGGCCAAAGAAATCTCACTCAGTTATT

CTGCTGGTGCACTTGCCAGTTGTATGGGCCTCATATACAACAGGATGG

GGGCTGTGACCACTGAAGTGGCATTTGGCCTGGTATGTGCAACCTGTG

TABLE 2-continued

M2-2—SEQ ID NO: 2 M2 ectodomain + 2 stops +
splice defect (PR8 M segment + 2 stops
(786-791) + splice defect nt 52) (also known
as "Splice def M2KO" or "Splice def")

AACAGATTGCTGACTCCCAGCATCGGTCTCATAGGCAAATGGTGACAA

CAACCAATCCACTAATCAGACATGAGAACAGAATGGTTTTAGCCAGCA

CTACAGCTAAGGCTATGGAGCAAATGGCTGGATCGAGTGAGCAAGCAG

CAGAGGCCATGGAGGTTGCTAGTCAGGCTAGACAAATGGTGCAAGCGA

TGAGAACCATTGGGACTCATCCTAGCTCCAGTGCTGGTCTGAAAAATG

ATCTTCTTGAAAATTTGCAGgcctatcagaaacgaatgggggtgcaga tgcaacggttcaagtgatTAATAGactattgccgcaaatatcattggg atcttgcacttgacattgtggattatgatcgtctttttttcaaatgca tttaccgtcgctttaaatacggactgaaaggagggccttctacggaag gagtgccaaagtctatgagggaagaatatcgaaaggaacagcagagtg ctgtggatgctgacgatggtcattttgtcagcatagagctggagtaaA

AAACTACCTTGTTTCTACT

No M2 polypeptide sequence is produced from this mutant.

TABLE 3

M2-3—SEQ ID NO: 3 M2 ectodomain + 2 stops +
splice defect + TM deletion (PR8 M segment + 2
stops (786-791) without 792-842 (TM) + splice
defect nt 52) (also known as TMdel + Splice
def M2KO)

3'AGCAAAAGCAGGTAGATATTGAAAGatgagtcttctaaccgaggtc gaaacCTACGTACTCTCTATCATCCCGTCAGGCCCCCTCAAAGCCGAG

ATCGCACAGAGACTTGAAGATGTCTTTGCAGGGAAGAACACCGATCTT

GAGGTTCTCATGGAATGGCTAAAGACAAGACCAATCCTGTCACCTCTG

ACTAAGGGGATTTTAGGATTTGTGTTCACGCTCACCGTGCCCAGTGAG

CGAGGACTGCAGCGTAGACGCTTTGTCCAAAATGCCCTTAATGGGAAC

GGGGATCCAAATAACATGGACAAAGCAGTTAAACTGTATAGGAAGCTC

AAGAGGGAGATAACATTCCATGGGCCAAAGAAATCTCACTCAGTTAT

TCTGCTGGTGCACTTGCCAGTTGTATGGGCCTCATATACAACAGGATG

GGGGCTGTGACCACTGAAGTGGCATTTGGCCTGGTATGTGCAACCTGT

GAACAGATTGCTGACTCCCAGCATCGGTCTCATAGGCAAATGGTGACA

ACAACCAATCCACTAATCAGACATGAGAACAGAATGGTTTTAGCCAGC

ACTACAGCTAAGGCTATGGAGCAAATGGCTGGATCGAGTGAGCAAGCA

GCAGAGGCCATGGAGGTTGCTAGTCAGGCTAGACAAATGGTGCAAGCG

ATGAGAACCATTGGGACTCATCCTAGCTCCAGTGCTGGTCTGAAAAAT

GATCTTCTTGAAAATTTGCAGgcctatcagaaacgaatgggggtgcag atgcaacggttcaagtgatTAATAGgatcgtctttttttcaaatgcat ttaccgtcgctttaaatacggactgaaaggagggccttctacggaagg agtgccaaagtctatgagggaagaatatcgaaaggaacagcagagtgc

TABLE 3-continued

M2-3—SEQ ID NO: 3 M2 ectodomain + 2 stops +
splice defect + TM deletion (PR8 M segment + 2
stops (786-791) without 792-842 (TM) + splice
defect nt 52) (also known as TMdel + Splice
def M2KO)

tgtggatgctgacgatggtcattttgtcagcatagagctggagtaaAA

AACTACCTTGTTTCTACT

No M2 polypeptide sequence is produced from this mutant.

Additionally or alternatively, in some embodiments, M2 mutations are introduced into the cytoplasmic tail. FIG. 2. The M2 protein cytoplasmic tail is a mediator of infectious virus production. In some embodiments, truncations of the M2 cytoplasmic tail result in a decrease in infectious virus titers, a reduction in the amount of packaged viral RNA, a decrease in budding events, and a reduction in budding efficiency. It has been shown that the 5' sequence is more important than 3' sequence for genome packaging, and that a longer 5' sequence is better for genome packaging. In addition, studies have shown that nucleotide length is important, but the actual sequence is less so (random sequences are sufficient to generate viruses). Stable M2 cytoplasmic tail mutants have been challenging to develop, and the literature includes numerous examples of mutant reversion.

For example, Pekosz et al JVI, 2005; 79(6): 3595-3605, replaced two codons with stop codons at amino acid position 70, but the virus soon reverted. Another exemplary M2 cytoplasmic tail mutation is termed M2del11. In the M2del11 mutant, 11 amino acid residues are deleted from carboxyl end of cytoplasmic tail. This truncation is due to the introduction of two stop codons, and a full length M2 polypeptide is not made. While this mutant is stable when passaged in M2 expressing MDCK cells (M2CK), it reverts to full length M2 during passaging in normal MDCK cells (J Virol. 2008 82(5):2486-92). Without wishing to be bound by theory, it is likely that reversion occurs with selective pressure in the MDCK cells.

Another M2 cytoplasmic tail mutant, M2Stop90ala78-81 did not reduce virus titer but ala70-77 did (JVI 2006; 80 (16) p8178-8189). Alanine-scanning experiments further indicated that amino acids at positions 74 to 79 of the M2 tail play a role in virion morphogenesis and affect viral infectivity. (J Virol. 2006 80(11):5233-40.)

Accordingly, presented herein are novel cytoplasmic mutants, with characteristics different than those described above. For example, in some embodiments, the cytoplasmic mutants are stable (do not revert to express a full-length M2 polypeptide) in MDCK cells. In some embodiments, the cytoplasmic mutants are stable for 2 passages, 3 passages, 5 passages, 10 passages, 15 passages, 20 passages, 25 passages or more than 25 passages in a host cell.

The wild-type M2 polypeptide is shown below in Table 4. For each of the sequences, the bold text indicates the transmembrane domain. The extracellular domain is first (left), followed by the transmembrane domain (center) and the cytoplasmic tail sequence (right).

TABLE 4

Wild-type M2 polypeptide and cytoplasmic tail mutants

Wild-type M2 polypeptide
MSLLTEVETPIRNEWGCRCNGSSDPLTIAANIIGILHLTLWILDRLFF
KCIYRRFKYGLKGGPSTEGVPKSMREEYRKEQQSAVDADDGHFVSIEL
E TABLE 4-continued Wild-type M2 polypeptide and cytoplasmic tail mutants M2-4: M2del FG#1; delete M2's 44-54 aa
(delete nucleotides 843-875; 11 aa)
MSLLTEVETPIRNEWGCRCNGSSDPLTIAANIIGILHLTLWILFKYGL
KGGPSTEGVPKSMREEYRKEQQSAVDADDGHFVSIELE M2-5: M2del FG#2; delete M2's 44-48 aa
(delete nucleotides 843-857; 5 aa)
MSLLTEVETPIRNEWGCRCNGSSDPLTIAANIIGILHLTLWILKCIYR
RFKYGLKGGPSTEGVPKSMREEYRKEQQSAVDADDGHFVSIELE M2-6: M2del FG#3; delete M2's 44 and 45 aa
(delete nucleotides 843-848; 2 aa)
MSLLTEVETPIRNEWGCRCNGSSDPLTIAANIIGILHLTLWILLFFKC
IYRRFKYGLKGGPSTEGVPKSMREEYRKEQQSAVDADDGHFVSIELE M2-4 (M2del FG #1) was generated but was not passagable in normal MDCK cells, but may be passagable in a modified host cell (e.g., a cell expressing a wild-type M2 polypeptide). M2-5 (M2del FG #2) and M2-6 (FG #3) were generated and passaged in normal MDCK cells. The nucleotide sequence of the M gene of these viruses are stable at least to passage 10 in MDCK cells. These mutants could be propagated and passaged in other cells as well (e.g., cells that support influenza replication). It was also found that these mutants are not attenuated and are pathogenic.

As described in the Examples below, the M2 mutant viruses described herein do not replicate in the respiratory tract or disseminate to other organs in the ferret model and are not transmitted in the ferret model. Vaccines comprising M2 mutant elicit robust immune responses in mammals and protect mammals against influenza virus challenge. M2KO virus elicits both humoral and mucosal immune responses in mice, and protects mice from lethal homosubtypic and heterosubtypic challenge. Vaccines comprising M2 mutant virus as described herein provide effective protection against influenza challenge and have the advantage of being attenuated in mammalian hosts. These findings demonstrate that the M2 mutant viruses described herein are useful for vaccines against influenza.

IV. Cell-Based Virus Production System

A. Producing "First Generation" Mutant Viruses

Mutant virus, such as those carrying mutant M2 nucleic acid, can be generated by plasmid-based reverse genetics as described by Neumann et al., *Generation of influenza A viruses entirely from clone cDNAs*, Proc. Natl. Acad. Sci. USA 96:9345-9350 (1999), herein incorporated by reference in its entirety. Briefly, eukaryotic host cells are transfected with one or more plasmids encoding the eight viral RNAs. Each viral RNA sequence is flanked by an RNA polymerase I promoter and an RNA polymerase I terminator. Notably, the viral RNA encoding the M2 protein includes the mutant M2 nucleic acid sequence. The host cell is additionally transfected with one or more expression plasmids encoding the viral proteins (e.g., polymerases, nucleoproteins and structural proteins), including a wild-type M2 protein. Transfection of the host cell with the viral RNA plasmids results in the synthesis of all eight influenza viral RNAs, one of which harbors the mutant M2 sequence. The co-transfected viral polymerases and nucleoproteins assemble the viral RNAs into functional vRNPs that are replicated and transcribed, ultimately forming infectious influenza virus having a mutant M2 nucleic acid sequence, yet having a functional M2 polypeptide incorporated into the viral lipid envelope.

Alternative methods of producing a "first generation" mutant virus include a ribonucleoprotein (RNP) transfection system that allows the replacement of influenza virus genes with in vitro generated recombinant RNA molecules, as described by Enami and Palese, *High-efficiency formation of influenza virus transfectants*, J. Virol. 65(5):2711-2713, which is incorporated herein by reference.

The viral RNA is synthesized in vitro and the RNA transcripts are coated with viral nucleoprotein (NP) and polymerase proteins that act as biologically active RNPs in the transfected cell as demonstrated by Luytjes et al., *Amplification, expression, and packaging of a foreign gene by influenza virus*, Cell 59:1107-1113, which is incorporated herein by reference.

The RNP transfection method can be divided into four steps: 1) Preparation of RNA: plasmid DNA coding for an influenza virus segment is transcribed into negative-sense RNA in an in vitro transcription reaction; 2) Encapsidation of the RNA: the transcribed RNA is then mixed with gradient purified NP and polymerase proteins isolated from disrupted influenza virus to form a biologically active RNP complex; 3) Transfection and rescue of the encapsidated RNA: the artificial ribonucleocapsid is transfected to the cells previously infected with a helper influenza virus that contains a different gene from the one being rescued; the helper virus will amplify the transfected RNA; 4) Selection of transfected gene: because both the helper virus and the transfectant containing the rescued gene are in the culture supernatant, an appropriate selection system using antibodies is necessary to isolate the virus bearing the transfected gene.

The selection system allows for the generation of novel transfectant influenza viruses with specific biological and molecular characteristics. Antibody selection against a target surface protein can then be used for positive or negative selection.

For example, a transfectant or mutant virus that contains an M2 gene that does not express an M2 protein can be grown in a suitable mammalian cell line that has been modified to stably express the wild-type functional M2 protein. To prevent or inhibit replication of the helper virus expressing the wild-type M2 gene, and therefore the M2e protein at the membrane surface, antibodies against M2e can be used. Such antibodies are commercially available and would inhibit the replication of the helper virus and allow for the transfectant/mutant virus containing the mutant M2 to grow and be enriched in the supernatant. Inhibition of influenza virus replication by M2e antibodies has been described previously in *Influenza A virus M2 protein: monoclonal antibody restriction of virus growth and detection of M2 in virions*, J Virol 62:2762-2772 (1988) and Treanor et al, *Passively transferred monoclonal antibody to the M2 protein inhibits influenza A virus replication in mice*, J. Virol. 64:1375-1377 (1990).

Additionally or alternatively, the same antibodies can be used to 'capture' the helper virus and allow for the enrichment of the transfectant. For example, the antibodies can be used to coat the bottom of a tissue culture dish or can be used in a column matrix to allow for enrichment for the transfectant in the supernatant or eluate.

The transfectant virus can be grown in M2 expressing cells in multi-well plates by limit dilution and then be identified and cloned, for example, by creating replica plates. For example, one-half of an aliquot of a given well of the multi-well plate containing the grown virus can be used to infect MDCK cells and the other half to infect MDCK cells that express M2 protein. Both the transfectant virus and helper virus will grow in MDCK cells that express M2 protein. However, only helper virus will grow in standard MDCK cells allowing for identifying the well in the multi-well plate that contains the transfectant. The transfectant virus can be further plaque purified in the cells that express M2 protein.

B. Propagating Viral Mutants

In some embodiments, viral mutants described herein are maintained and passaged in host cells. By way of example, but not by way of limitation, exemplary host cells appropriate for growth of influenza viral mutants, such as influenza A viral mutants include any number of eukaryotic cells, including, but not limited to Madin-Darby canine kidney cells (MDCK cells), simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

Additionally or alternatively, in some embodiments, the eukaryotic host cell is modified to enhance viral production, e.g., by enhancing viral infection of the host cell and/or by enhancing viral growth rate. For example, in some embodiments, the host cell is modified to express, or to have increased expression, of 2,6-linked sialic acid on the cell surface, allowing for more efficient and effective infection of these cells by mutant or wild-type influenza A viruses. See e.g., U.S. Patent Publication No. 2010-0021499, and U.S. Pat. No. 7,176,021, herein incorporated by reference in their entirety. Thus, in some illustrative embodiments, Chinese Hamster Ovary Cells (CHO cells) and/or Vero cells modified to express at least one copy of a 2,6-sialyltransferase gene (ST6GAL 1) are used. By way of example, but not by way of limitation, the *Homo sapiens* ST6 beta-galatosamide alpha-2,6-sialyltransferase gene sequence denoted by the accession number BC040009.1, is one example of a ST6Gal gene that can be integrated into and expressed by a CHO cell. One or more copies of a polynucleotide that encodes a functional ST6Gal I gene product can be engineered into a cell. That is, cells which have been stably transformed to express 1, 2, 3, 4, 5, 6, 7, 8, 9, 10, 11, 12, or more than 12 copies of a ST6Gal I gene may be used. A single expression cassette may include one or more copies of the ST6Gal I gene to be expressed, which is operably linked to regulatory elements, such as promoters, enhancers, and terminator and polyadenylation signal sequences, to facilitate the expression of the ST6Gal I gene or its copies. Alternatively, a single expression cassette may be engineered to express one copy of an ST6Gal I gene, and multiple expression cassettes integrated into a host cell genome. Accordingly, in some embodiments, at least one ST6Gal I gene is incorporated into the genome of a host cell, such that the cell expresses the ST6Gal I gene and its enzymatic protein product. Depending on the copy number, a single host cell may express many functional ST6Gal I gene proteins.

Suitable vectors for cloning, transfecting and producing stable, modified cell lines are well known in the art. One non-limiting example includes the pcDNA3.1 vectors (Invitrogen).

Additionally or alternatively, in some embodiments, the eukaryotic host cell is modified to produce a wild-type version of a mutant viral gene, thereby providing the gene to the virus in trans. For example, a viral strain harboring a mutant M2 protein may exhibit an enhanced growth rate (e.g., greater viral production) when passaged in host cells producing the wild-type M2 protein. In some embodiments, the a viral strain harboring a mutant M2 protein may not grow or replicate in a cell which does not express a wild-type M2 gene. In addition, such host cells may slow or prevent viral reversion to a functional M2 sequence, because, for example, there is no selective pressure for reversion in such a host.

Method for producing both expression vectors and modified host cells are well known in the art. For example, an M2 expression vector can be made by positioning the M2 nucleic acid sequence (M2 ORF sequence; this is "wild-type" M2's start codon to stop codon (Table 5)) below in a eukaryotic expression vector.

TABLE 5

Wild-type M2 nucleic acid sequence atgagtcttctaaccgaggtcgaaacgcctatcagaaacgaatggggg tgcagatgcaacggttcaagtgatcctctcactattgccgcaaatatc attgggatcttgcacttgacattgtggattcttgatcgtcttttttc aaatgcatttaccgtcgctttaaatacggactgaaaggagggccttct acggaaggagtgccaaagtctatgagggaagaatatcgaaaggaacag cagagtgctgtggatgctgacgatggtcatttttgtcagcatagagctg gagtaa Host cells (e.g., MDCK cells) can then be transfected by methods known in the art, e.g., using commercially available reagents and kits, such as TransIT® LT1 (Mirus Bio, Madison, Wis.). By way of example, but not by way of limitation, cells can be selected and tested for M2 expression by cotransfection with a detectable marker or a selectable marker (e.g., hygromycin-resistance) and/or by screening, for example, with indirect immunostaining using an M2 antibody. M2 expression can be determined by indirect immunostaining, flow cytometry or ELISA.

By way of example, but not by way of limitation, 293T human embryonic kidney cells and Madin-Darby canine kidney (MDCK) cells were maintained in Dulbecco's modified Eagle's medium supplemented with 10% fetal calf serum and in minimal essential medium (MEM) containing 5% newborn calf serum, respectively. All cells were maintained at 37° C. in 5% $CO_2$. Hygromycin-resistant MDCK cells stably expressing M2 protein from A/Puerto Rico/8/34 (H1N1) were established by cotransfection with plasmid pRHyg, containing the hygromycin resistance gene, and plasmid pCAGGS/M2, expressing the full-length M2 protein, at a ratio of 1:1. The stable MDCK cell clone (M2CK) expressing M2 was selected in medium containing 0.15 mg/mL of hygromycin (Roche, Mannheim, Germany) by screening with indirect immunostaining using an anti-M2 (14C2) monoclonal antibody (Iwatsuki et al. JVI, 2006, vol. 80, No. 1, p. 5233-5240). The M2CK cells were cultured in MEM supplemented with 10% fetal calf serum and 0.15 mg/mL of hygromycin. In M2CK cells, the expression levels and localization of M2 were similar to those in virus-infected cells (data not shown). M2 expressing Vero cells can be made in a similar fashion.

In some embodiments, cells and viral mutants are cultured and propagated by methods well known in the art. By way of example, but not by way of limitation, in some embodiments, host cells are grown in the presence of MEM supplemented with 10% fetal calf serum. Cells expressing M2 are infected at an MOI of 0.001 by washing with PBS followed by adsorbing virus at 37° C. In some embodiments, viral growth media containing trypsin/TPCK is added and the cells are incubated for 2-3 days until cytopathic effect is observed.

Along these lines, disposable bioreactor systems have been developed for mammalian cells, with or without virus, whose benefits include faster facility setup and reduced risk of cross-contamination. The cells described herein, for instance, can be cultured in disposable bags such as those from Stedim, Bioeaze bags from SAFC Biosciences, HybridBag™ from Cellexus Biosytems, or single use bioreactors from HyClone or Celltainer from Lonza. Bioreactors can be 1 L, 10 L, 50 L, 250 L, 1000 L size formats. In some embodiments, the cells are maintained in suspension in optimized serum free medium, free of animal products. The system can be a fed-batch system where a culture can be expanded in a single bag from 1 L to 10 L for example, or a perfusion system that allows for the constant supply of nutrients while simultaneously avoiding the accumulation of potentially toxic by-products in the culture medium.

For long term storage, mutant virus can be stored as frozen stocks.

V. Vaccines and Method of Administration

A. Immunogenic Compositions/Vaccines

There are various different types of vaccines which can be made from the cell-based virus production system disclosed herein. The present disclosure includes, but is not limited to, the manufacture and production of live attenuated virus vaccines, inactivated virus vaccines, whole virus vaccines, split virus vaccines, virosomal virus vaccines, viral surface antigen vaccines and combinations thereof. Thus, there are numerous vaccines capable of producing a protective immune response specific for different influenza viruses where appropriate formulations of any of these vaccine types are capable of producing an immune response, e.g., a systemic immune response. Live attenuated virus vaccines have the advantage of being also able to stimulate local mucosal immunity in the respiratory tract.

In some embodiments, vaccine antigens used in the compositions described herein are "direct" antigens, i.e. they are not administered as DNA, but are the antigens themselves. Such vaccines may include a whole virus or only part of the virus, such as, but not limited to viral polysaccharides, whether they are alone or conjugated to carrier elements, such as carrier proteins, live attenuated whole microorganisms, inactivated microorganisms, recombinant peptides and proteins, glycoproteins, glycolipids, lipopeptides, synthetic peptides, or ruptured microorganisms in the case of vaccines referred to as "split" vaccines.

In some embodiments a complete virion vaccine is provided. A complete virion vaccine can be concentrated by ultrafiltration and then purified by zonal centrifugation or by chromatography. Typically, the virion is inactivated before or after purification using formalin or beta-propiolactone, for instance.

In some embodiments, a subunit vaccine is provided, which comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by standard methods.

In some embodiments, a split vaccine is provided, which comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

In some embodiments, inactivated influenza virus vaccines are provided. In some embodiments, the inactivated vaccines are made by inactivating the virus using known methods, such as, but not limited to, formalin or B-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Additionally or alternatively, in some embodiments, live attenuated influenza virus vaccines are provided. Such vaccines can be used for preventing or treating influenza virus infection, according to known method steps.

In some embodiments, attenuation is achieved in a single step by transfer of attenuated genes from an attenuated donor virus to an isolate or reassorted virus according to known methods (see, e.g., Murphy, Infect. Dis. Clin. Pract. 2, 174 (1993)). In some embodiments, a virus is attenuated by mutation of one or more viral nucleic acid sequences, resulting in a mutant virus. For example, in some embodiments, the mutant viral nucleic acid sequence codes for a defective protein product. In some embodiments, the protein product has diminished function or no function. In other embodiments, no protein product is produced from the mutant viral nucleic acid.

The virus can thus be attenuated or inactivated, formulated and administered, according to known methods, as an immunogenic composition (e.g., as a vaccine) to induce an immune response in an animal, e.g., an avian and/or a mammal. Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) or other mutant sequences (e.g., M2) are not present in the attenuated viruses. See, e.g., Robertson et al., Giornale di Igiene e Medicina Preventiva, 29, 4 (1988); Kilbourne, Bull. M2 World Health Org., 41, 643 (1969); and Robertson et al., Biologicals, 20, 213 (1

In some embodiments, the vaccine includes an attenuated influenza virus that lacks expression of a functional M2 protein. In some embodiments, the mutant virus replicates well in cells expressing M2 proteins, but in the corresponding wild-type cells, expresses viral proteins without generating infectious progeny virions.

Pharmaceutical compositions of the present invention, suitable for intradermal administration, inoculation or for parenteral or oral administration, comprise attenuated or inactivated influenza viruses, and may optionally further comprising sterile aqueous or non-aqueous solutions, suspensions, and emulsions. The compositions can further comprise auxiliary agents or excipients, as known in the art. See, e.g., Berkow et al., The Merck Manual, 15th edition, Merck and Co., Rahway, N.J. (1987); Goodman et al., eds., Goodman and Gilman's The Pharmacological Basis of Therapeutics, Eighth Edition, Pergamon Press, Inc., Elmsford, N.Y. (1990); Avery's Drug Treatment: Principles and Practice of Clinical Pharmacology and Therapeutics, Third Edition, ADIS Press, LTD., Williams and Wilkins, Baltimore, Md. (1987); and Katzung, ed., Basic and Clinical Pharmacology, Fifth Edition, Appleton and Lange, Norwalk, Conn. (1992).

In some embodiments, preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances that augment a specific immune response, can be used. Normally, the adjuvant and the composition are mixed prior to presentation to the immune system, or presented separately, but into the same site of the organism being immunized.

In some embodiments, the immunogenic compositions (e.g., vaccines) disclosed herein include multiple, different types of virus or viral antigens, at least one of which includes a mutant M2 gene (e.g., a virus comprising the M2KO (ΔTM) (SEQ ID NO:1) mutation), and/or a corresponding mutation in the M2 functional equivalent of that virus (e.g., the NB protein of influenza B, or the CM1 protein of influenza C). In other embodiments, the immunogenic compositions include a single type of virus or viral antigen which includes a mutant M2 gene (e.g., a virus comprising the M2KO(ΔTM) (SEQ ID NO:1) mutation) and/or a corresponding mutation in the M2 functional equivalent of that virus (e.g., the NB protein of influenza B, or the CM1 protein of influenza C). For example, in some embodiments, the main constituent of an immunogenic compositions such as a vaccine composition includes one or more influenza viruses of type A, B or C, or any combination thereof or any combination of antigens from these viruses, wherein at least one virus includes a mutant M2 gene (e.g., a virus comprising the M2KO(ΔTM) (SEQ ID NO:1) mutation) and/or a corresponding mutation in the M2 functional equivalent of that virus (e.g., the NB protein of influenza B, or the CM1 protein of influenza C) For example, in some embodiments, at least two of the three types, at least two of different subtypes, at least two of the same type, at least two of the same subtype, or a different isolate(s) or reassortant(s) are provided in an immunogenic composition (e.g., a vaccine). By way of example, but not by way of limitation, human influenza virus type A includes H1N1, H2N2 and H3N2 subtypes. In some embodiments, the immunogenic compositions (e.g., vaccines) include a virus comprising a mutant M2 gene (e.g., a virus comprising the M2KO(ΔTM) (SEQ ID NO:1) mutation) and/or a corresponding mutation in the M2 functional equivalent of that virus (e.g., the NB protein of influenza B, or the CM1 protein of influenza C) and about 0.1 to 200 μg, e.g., 10 to 15 μg of hemagglutinin from each of the strains entering into the composition. Heterogeneity in a vaccine may be provided by mixing replicated influenza viruses for at least two influenza virus strains, such as from 2-50 strains, or any range or value therein. In some embodiments, influenza A or B virus strains having a modern antigenic composition are used. In addition, immunogenic compositions (e.g., vaccines) can be provided for variations in a single strain of an influenza virus, using techniques known in the art.

In some embodiments, the vaccine comprises a virus comprising the M2KO(ΔTM) (SEQ ID NO:1) mutation together with other viral components and/or genes expressing other viral components. In some embodiments, the vaccine (e.g., a virus comprising the M2KO(ΔTM) (SEQ ID NO:1) mutation) comprises genes from other viral strains, including but not limited to, for example, HA and NA genes from other viral strains. In some embodiments, the vaccine comprises HA and NA genes from human influenza virus type A subtypes H5N1, H1N1, H2N2 or H3N2. In some embodiments, the vaccine comprises HA and NA genes from, for example, PR8xBrisbane/10/2007, A/Vietnam/1203/2004, or A/California/07/2009 (CA07) viruses.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-α, interferon-β, interferon-γ, tumor necrosis factor-α, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition of the invention is administered.

B. Administration

An immunogenic composition (e.g., vaccine) as disclosed herein may be administered via any of the routes conventionally used or recommended for vaccines: parenteral route, mucosal route, and may be in various forms: injectable or sprayable liquid, formulation which has been freeze-dried or dried by atomization or air-dried, etc. Vaccines may be administered by means of a syringe or by means of a needle-free injector for intramuscular, subcutaneous or intradermal injection. Vaccines may also be administered by means of a nebulizer capable of delivering a dry powder or a liquid spray to the mucous membranes, whether they are nasal, pulmonary, vaginal or rectal.

A vaccine as disclosed herein may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. In some embodiments, an immunogenic composition as disclosed herein is by intramuscular or subcutaneous application.

In some embodiments, a regimen for preventing, suppressing, or treating an influenza virus related pathology comprises administration of an effective amount of a vaccine composition as described herein, administered as a single treatment, or repeated as enhancing or booster dosages, over a period up to and including between one week and about 24 months, or any range or value therein. In some embodiments, an influenza vaccine as disclosed herein is administered annually.

According to the present invention, an "effective amount" of a vaccine composition is one that is sufficient to achieve a desired biological effect. It is understood that, in some embodiments, the effective dosage will be dependent upon the age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of an attenuated virus vaccine for a mammalian (e.g., human) adult can be from about $10^3$-$10^7$ plaque forming units (PFU), or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

C. Intracutaneous Delivery

Live flu vaccines are traditionally delivered intranasally to mimic the natural route of infection and promote a similar immune response to that of natural virus infection. As an alternative, disclosed herein are intradermal delivery methods which involve the use of a novel microneedle device to capitalize on the immunological benefits of intradermal delivery. In some embodiments, an attenuated virus (e.g., an M2 viral mutant) is used in a vaccine composition for intradermal administration. In some embodiments, an M2 viral mutant, which does not produce infectious progeny virus, is provided in a vaccine. Thus, any potential of reassortment with wild-type circulating influenza viruses is virtually eliminated.

In embodiments disclosed herein, intradermal delivery (intracutaneous) administers vaccine to the skin. In some embodiments, intradermal delivery is performed using a microneedle delivery device. As disclosed herein, intracutaneous delivery has numerous advantages. For example, the immunogenicity of the vaccine is enhanced by triggering the immunological potential of the skin immune system. The vaccine has direct access to the potent antigen-presenting dendritic cells of the skin, i.e., epidermal Langerhans Cells and dermal dendritic cells. Skin cells produce proinflammatory signals which enhance the immune response to antigens introduced through the skin. Further, the skin immune system produces antigen-specific antibody and cellular immune responses. Intradermal delivery allows for vaccine dose sparing, i.e., lower doses of antigen may be effective, in light of the above factors, when delivered intracutaneously.

And, because the vaccine is delivered to the skin through the device's microneedle array, the risk of unintended needle-sticks is reduced, and intracutaneous vaccine delivery via microneedle array is relatively painless compared to intramuscular injections with conventional needle and syringe.

Microneedle devices are known in the art, are known in the art, including, for example, those described in published U.S. patent applications 2012/0109066, 2011/0172645, 2011/0172639, 2011/0172638, 2011/0172637, and 2011/0172609. Microneedle devices may be made, for example, by fabrication from stainless steel sheets (e.g., Trinity Brand Industries, Georgia; SS 304; 50 µm thick) by wet etching. In some embodiments, individual microneedles have a length of between about 500 µm and 1000 µm, e.g., about 750 µm, and a width of between about 100 µm to 500 µm, e.g., about 200 µm. Vaccine can then be applied to the microneedles as a coating. By way of example, but not by way of limitation, a coating solution may include 1% (w/v) carboxymethyl cellulose sodium salt (low viscosity, USP grad; Carbo-Mer, San Diego Calif.), 0.5% (w/v) Lutrol F-68 NF (BASF, Mt. Olive, N.J.) and the antigen (e.g., soluble HA protein at 5 ng/ml; live, attenuated virus such as the M2 mutant virus described herein, etc.). To reach a higher vaccine concentration, the coating solution may be evaporated for 5 to 10 minutes at room temperature (~23° C.). Coating may be performed by a dip coating process. The amount of vaccine per row of microneedles can be determined by submerging the microneedles into 200 µl of phosphate-buffered saline (PBS) for 5 minutes and assaying for the antigen by methods known in the art.

In some embodiments, a microneedle device is used that is made mainly of polypropylene and stainless steel first-cut pieces that fit together with simple snap fits and heat seals. In some embodiments, the device is completely self-contained and includes the vaccine, a pump mechanism, an activation mechanism, and a microneedle unit. These components are hidden within a plastic cover. With the device, vaccine infusion is initiated by pressing an actuation button. Pressing the button simultaneously inserts the microneedles into the skin and initiates the pumping mechanism that exerts pressure on the primary drug container. When a spring mechanism exerts sufficient pressure on the vaccine reservoir, vaccine begins to flow through the microneedle array, and into the skin. In some embodiments, the delivery of the vaccine dose is completed within about 2 minutes after actuation of the device. After infusion is complete, the device is gently removed from the skin.

In some embodiments, a method for intracutaneous administration of an immunogenic composition (e.g., a vaccine) is provided using a microneedle device. In some embodiments, the microneedle device comprises a puncture mechanism and an immunogenic composition layer comprising a plurality of microneedles capable of puncturing skin and allowing an immunogenic composition to be administered intracutaneously. In some embodiments, the method comprises depressing the puncture mechanism. In some embodiments, the immunogenic composition (e.g. vaccine) comprises a virus comprising a nucleic acid sequence encoding a mutant M2 protein that is expressed or a mutant M2 protein that is not expressed; wherein the expressed mutant M2 protein comprises, or consists of, the amino acid sequence of SEQ ID NO: 4. In some embodiments, the microneedle array is initially positioned inside of a device housing, and upon actuation of a lever allows the microneedles to extend through the device bottom and insert into the skin thereby allowing infusion of the vaccine fluid into the skin.

The delivery device described herein may be utilized to deliver any substance that may be desired. In one embodiment, the substance to be delivered is a drug, and the delivery device is a drug delivery device configured to deliver the drug to a subject. As used herein the term “drug” is intended to include any substance delivered to a subject for any therapeutic, preventative or medicinal purpose (e.g., vaccines, pharmaceuticals, nutrients, nutraceuticals, etc.). In one such embodiment, the drug delivery device is a vaccine delivery device configured to deliver a dose of vaccine to a subject. In one embodiment, the delivery device is configured to deliver a flu vaccine. The embodiments discussed herein relate primarily to a device configured to deliver a substance transcutaneously. In some embodiments, the device may be configured to deliver a substance directly to an organ other than the skin.

EXAMPLES

While the following examples are demonstrated with influenza A, it is understood that the mutations and methods described herein are equally applicable to other viruses which express an M2, an M2-like protein or a protein with the same or similar function as the influenza A M2 protein.

Example 1: Generation of M2 Viral Mutants

M2 mutants were constructed as follows.

a) M2-1: M2 ectodomain+2 stop codons+TM deletion (PR8 M segment+2 stops (786-791) without 792-842 (TM))

Partial wild-type M genes from PR8 were amplified by PCR using oligo set 1 and oligo set 2 as shown below.

TABLE 6

| Oligo Set 1 |
|---|
| acacacCGTCTCTAGgatcgtatttttttcaaatgcatttacc |
| CACACACGTCTCCTATTAGTAGAAACAAGGTAGTTTTT |
| Oligo Set 2 |
| acacacCGTCTCatcCTATTAatcacttgaaccgttgc |
| CACACACGTCTCCGGGAGCAAAAGCAGGTAG |

The PCR products were then digested with BsmBI. An expression vector (pHH21) was also digested with BsmBI, and the digested PCR products were ligated into the vector using T4 DNA ligase. *E. coli* cells were transformed with the vector, and after appropriate incubation, vectors were isolated and purified by methods known in the art. The mutant M2 portion of the vector was characterized by nucleic acid sequencing.

b) M2-2: M2 ectodomain+2 stops+splice defect (PR8 M segment+2 stops (786-791)+splice defect nt 51)

Partial wild-type M genes from PR8 were amplified by PCR using the primer set shown below.

TABLE 7

| PCR primers |
|---|
| 5'acacacCGTCTCcCTACGTACTCTCTATCATCCCG |
| 5'CACACACGTCTCCTATTAGTAGAAACAAGGTAGTTTTT |

The PCR products were then digested with BsmBI. An expression vector (pHH21) was also digested with BsmBI. A double-stranded DNA fragment was then made by annealing the two nucleotides shown below.

TABLE 8

| Annealing nucleotides |
|---|
| 5'GGGAGCAAAAGCAGGTAGATATTGAAAGatgagtcttctaaccgag gtcgaaac |
| 5'GTAGgtttcgacctcggttagaagactcatCTTTCAATATCTACCT GCTTTTGC |

The digested vector, PCR product and double-stranded fragment were then ligated using T4 DNA ligase. *E. coli* cells were transformed with the vector, and after appropriate incubation, the vectors were isolated and purified by methods known in the art. The mutant M2 portion of the vector was characterized by nucleic acid sequencing.

c) M2-3: M2 ectodomain+2 stops+splice defect+TM deletion (PR8 M segment+2 stops (786-791) without 792-842 (TM)+splice defect nt 51)

The partial M2-1 mutant (M2 ectodomain+2 stop codons+TM deletion (PR8 M segment+2 stops (786-791) without 792-842 (TM)) was amplified from PR8 by PCR using the following primers:

TABLE 9

| PCR primers |
|---|
| 5'acacacCGTCTCcCTACGTACTCTCTATCATCCCG |
| 5'CACACACGTCTCCTATTAGTAGAAACAAGGTAGTTTTT |

The PCR products were then digested with BsmBI. An expression vector (pHH21) was also digested with BsmBI. A double-stranded DNA fragment was then made by annealing the two nucleotides shown below.

TABLE 10

| Annealing nucleotides |
|---|
| 5'GGGAGCAAAAGCAGGTAGATATTGAAAGatgagtcttctaaccgag gtcgaaac |
| 5'GTAGgtttcgacctcggttagaagactcatCTTTCAATATCTACCT GCTTTTGC |

The digested vector, PCR product and double-stranded fragment were then ligated using T4 DNA ligase. E. coli cells were transformed with the vector, and after appropriate incubation, the vectors were isolated and purified by methods known in the art. The mutant M2 portion of the vector was characterized by nucleic acid sequencing.

The sequence of each of the three M2 mutant constructs is provided in Tables 1-3.

Example 2: Generation and Culturing of M2 Mutant Virus

This example demonstrates the culturing of the PR8 virus comprising the M2KO(ΔTM) (SEQ ID NO:1) mutation. Mutant viruses were generated as reported in Neumann et al., *Generation of influenza A viruses entirely from clone cDNAs*, Proc. Natl. Acad. Sci. USA 96:9345-9350 (1999), with some modifications. Briefly, 293T cells were transfected with 17 plasmids: 8 PolI constructs for 8 RNA segments, one of which harbors the mutant M2 sequence, and 9 protein-expression constructs for 5 structural proteins as follows: NP (pCAGGS-WSN-NP0/14); M2 (pEP24c); PB1 (pcDNA774); PB2 (pcDNA762); and PA (pcDNA787) of A/Puerto Rico/8/34 (H1N1) virus.

The plasmids were mixed with transfection reagent (2 μL of Trans IT® LT-1 (Mirus, Madison, Wis.) per μg of DNA), incubated at room temperature for 15-30 minutes, and added to $1 \times 10^6$ 293 T cells. Forty-eight hours later, viruses in the supernatant were serially diluted and inoculated into M2CK cells. Two to four days after inoculation, viruses in supernatant of the last dilution well in which cells showing clear cytopathic effect (CPE) were inoculated into M2CK cells for the production of stock virus. The M genes of generated viruses were sequenced to confirm the gene and the presence of the intended mutations and to ensure that no unwanted mutations were present.

Mutant M2 viruses were grown and passaged as follows. M2CK host cells were grown in the presence of MEM supplemented with 10% fetal calf serum. Cells were infected at an MOI of 0.001 by washing with PBS followed by adsorbing virus at 37° C. Virus growth media containing trypsin/TPCK was added and the cells were incubated for 2-3 days until cytopathic effect was observed.

Example 3 M2KO Replication is Restricted in Normal Cells

Figure 4A:
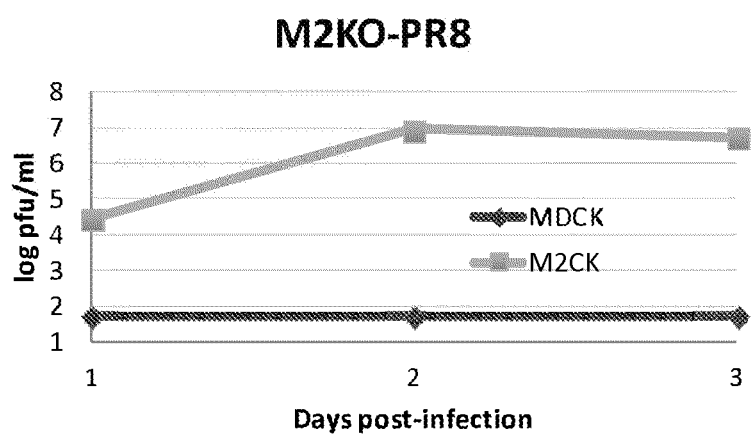
FIGS. 4A and 4B are charts showing the growth kinetics of M2KO(ΔTM) (4A) and wild-type PR8 (4B) viruses in normal MDCK cells and MDCK cells stably expressing M2 protein (M2CK). Cells were infected with viruses at multiplicity of infection of $10^{-5}$. Virus titers in cell supernatants were determined. Wild-type PR8 grew to high titers in both cell types whereas M2KO(ΔTM) grew well only in M2CK cells and not at all in MDCK cells.
Figure 4B:
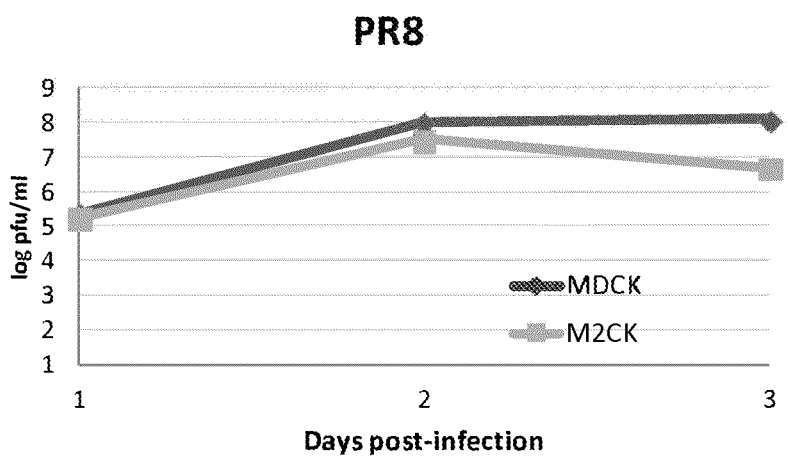

Growth kinetics of the PR8 virus with the M2KO(ΔTM) (SEQ ID NO:1) mutation and wild-type PR8 were analyzed in both normal MDCK cells and MDCK cells stably expressing M2 protein (M2CK). Cells were infected with viruses at multiplicity of infection of $10^{-5}$. Virus titers in cell supernatant were determined in MDCK or M2CK cells. Wild-type PR8 grew to high titers in both cell types whereas M2KO grew well only in M2CK cells and not at all in MDCK cells (FIGS. 4A and 4B).

Example 4: M2KO Virus Produces Viral Antigens, but not M2, in Normal Cells

Figure 5A:
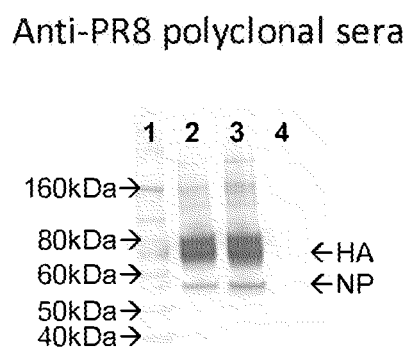
FIGS. 5A and 5B are western blots showing that M2KO (ΔTM) virus produces viral antigens, but not M2, in normal cells. Cellular lysates were probed with PR8-infected mouse sera (5A) or anti-M2 monoclonal antibody (5B). Lane 1, Molecular weight marker; Lane 2, MDCK cells infected with PR8; Lane 3 MDCK cells infected with M2KO(ΔTM); Lane 4, Uninfected MDCK cells.
Figure 5B:
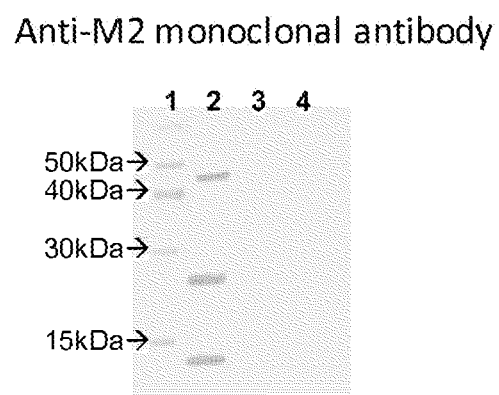

This example demonstrates that the PR8 virus with the M2KO(ΔTM) (SEQ ID NO:1) mutation produces viral antigens, but not M2 protein, in normal cells. Viral protein expression was evaluated by infecting wild-type MDCK cells with wild-type PR8 or M2KO at a multiplicity of infection (MOI) of 0.5 in medium without trypsin to ensure that viruses complete only one life cycle. Viral proteins in the cell lysates were separated on a 4-12% SDS-PAGE gel and detected by Western blot using PR8 infected mouse sera (Panel A) or anti-M2 monoclonal antibody (14C2, Santa Cruz Biotechnology) (Panel B). FIG. 3A shows that antisera against PR8 detects similar levels of protein expression for both PR8 and M2KO. When the lysates are probed with an anti-M2 monoclonal antibody (Panel B), M2 expression is detected only in PR8 infected cells, not M2KO. These results indicate that M2KO virus expresses all viral proteins, except M2 protein, to similar levels as PR8 virus (FIGS. 5A and 5B)

Example 5: M2 Mutants are Attenuated In Vivo

An experiment was performed to demonstrate that M2 mutant viruses are attenuated in vivo. Six weeks old BALB/c, female mice (23 per group) were inoculated intranasally with one of the following mutants: M2KO(yk) as described in J. Virol (2009) 83:5947-5950; M2-1 (TM del M2KO aka M2KO(ΔTM)) and M2-2 (Splice def M2KO) (collectively termed "M2KO variants"). The mutant was administered at a dose of $1.2 \times 10^4$ pfu per mouse. A control group of mice was given PBS. The mice were observed for 14 days after inoculation for any change in body weight and symptoms of infection. Additionally, after 3 days post-inoculation, virus titers were taken from the lungs and nasal turbinates (NT) from 3 mice in each group.

Figure 6:
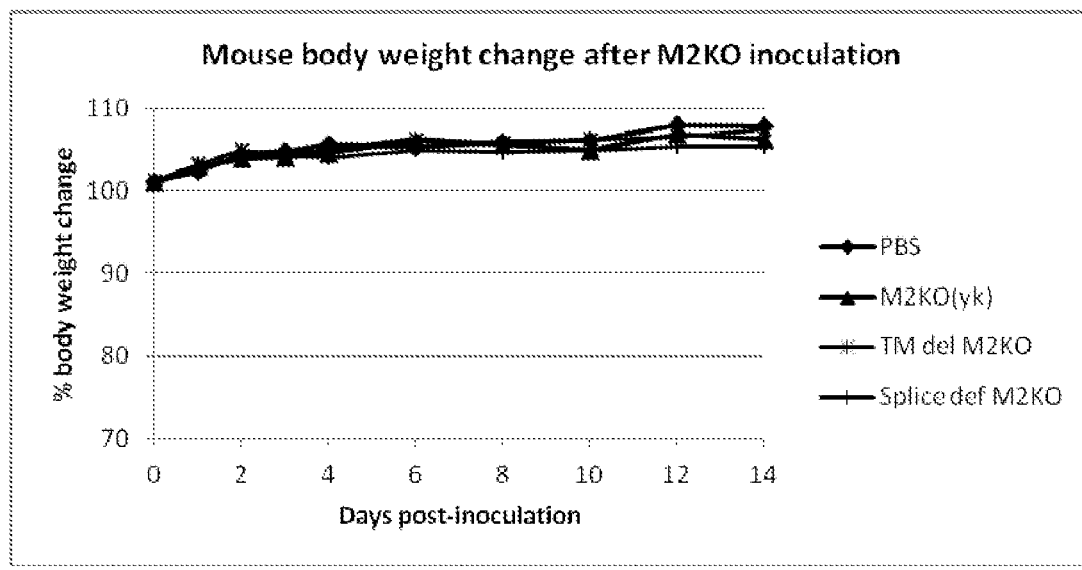
FIG. 6 is a chart showing the change in mouse body weight after inoculation with M2KO variants.

As shown in FIG. 6, mice inoculated with the M2KO variants and PBS did not show any clinical symptoms of infection nor lose any body weight over the 14 day period. The change in body weight between the groups were comparable over the 14 day period. Additionally, no virus was detected in the titers that were gathered from the lungs and NT. Together, the lack of clinical symptoms, lack of loss of body weight and absence of virus indicate that the M2 mutant viruses are attenuated and not pathogenic in mice.

Figure 7A:
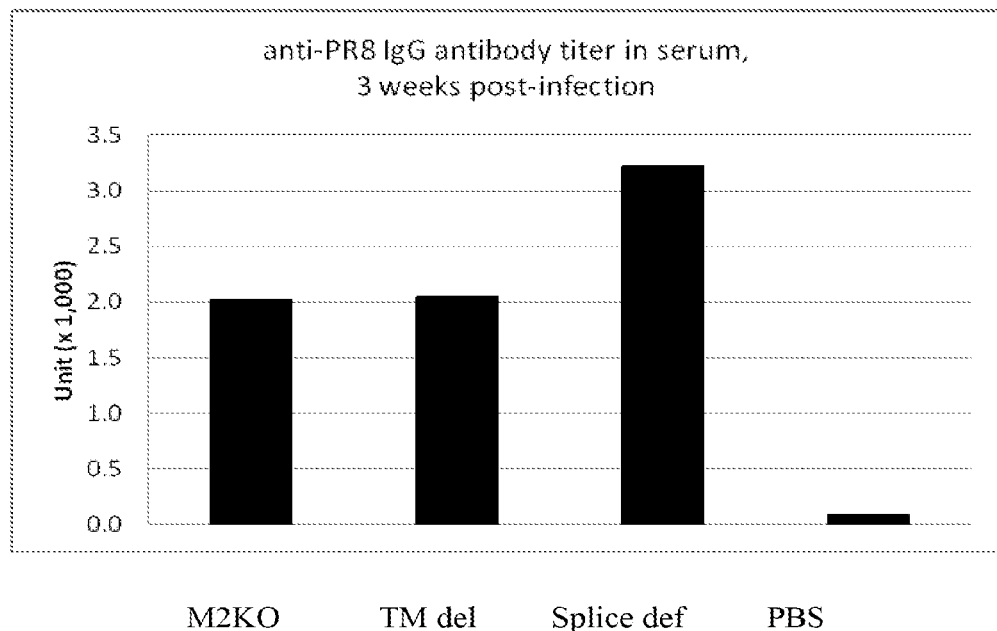
FIG. 7A is a chart showing antibody response in mice inoculated with M2KO variants.

Example 6: M2 Mutants Induce Antibodies Against Influenza Virus and Protect Mice from Lethal Virus Challenge Testing was also performed to determine antibody titers from the mice described in Example 5 above and their survival after being challenged with a lethal viral dose. Serum samples were taken 3 weeks after inoculation and anti-virus IgG antibody titers from the serum samples were determined by enzyme-linked immunosorbent assay (ELISA). The humoral response is shown in FIG. 7, which shows that all three M2 mutants elevated anti-influenza virus antibodies higher than the control PBS group.

Figure 7B:
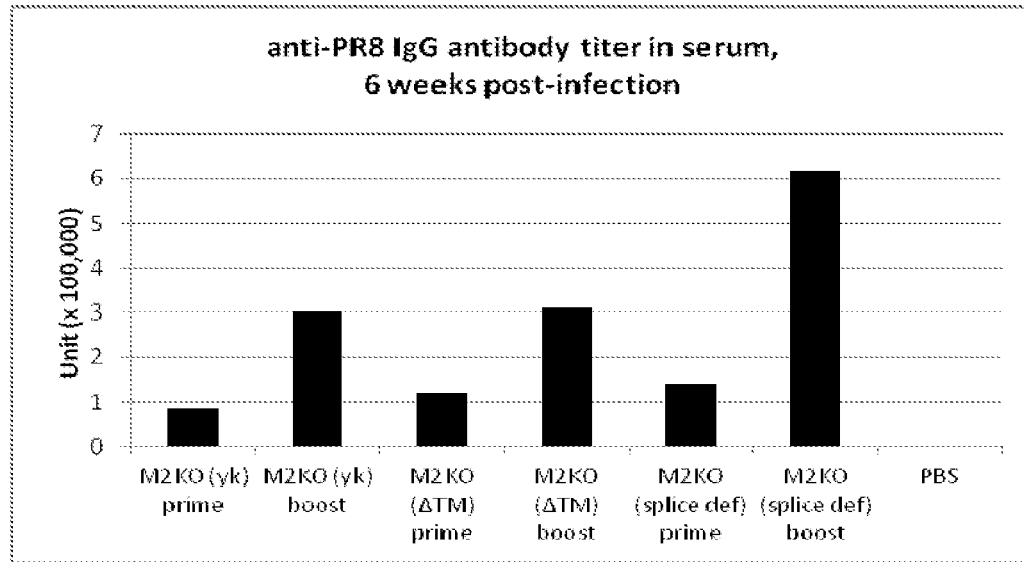
FIG. 7B is a chart showing anti-PR8 IgG antibody titer in the serum of boosted mice 6 weeks post infection.

In addition, half of the mice within each of the groups were boosted 28 days after inoculation with same amount of M2 mutant virus. Serum was then collected 6 weeks after the first inoculation and IgG titers against the virus were determined. As shown in FIG. 7B, mice boosted by M2 mutant viruses had a higher level of anti-influenza virus antibodies than ones were not boosted.

Figure 8:
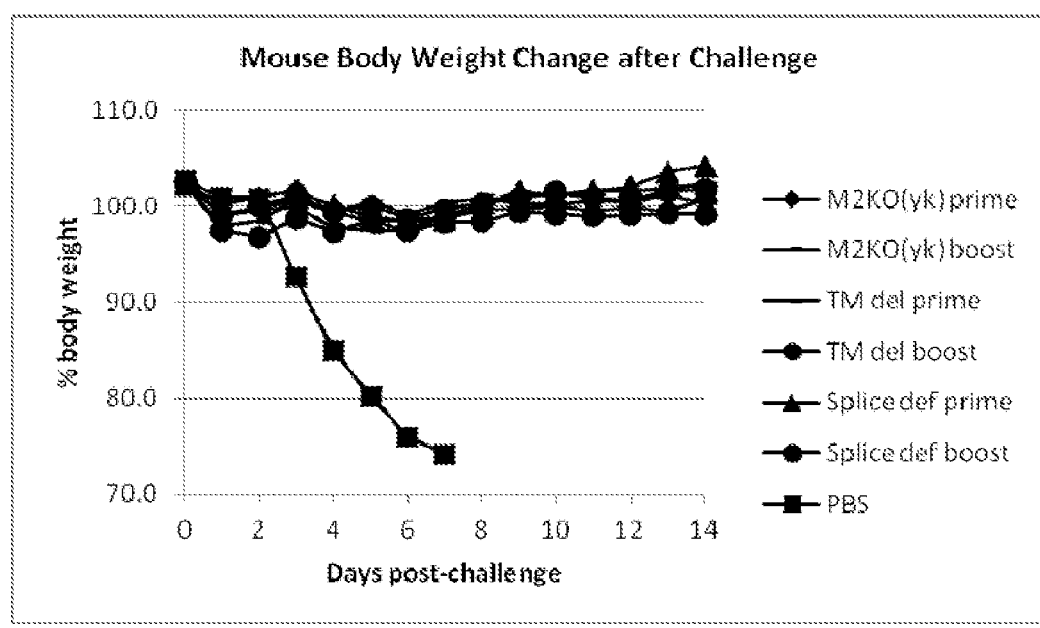
FIG. 8 is a chart showing change in mouse body weight after influenza challenge, post-inoculation with M2KO variants.
Figure 9:
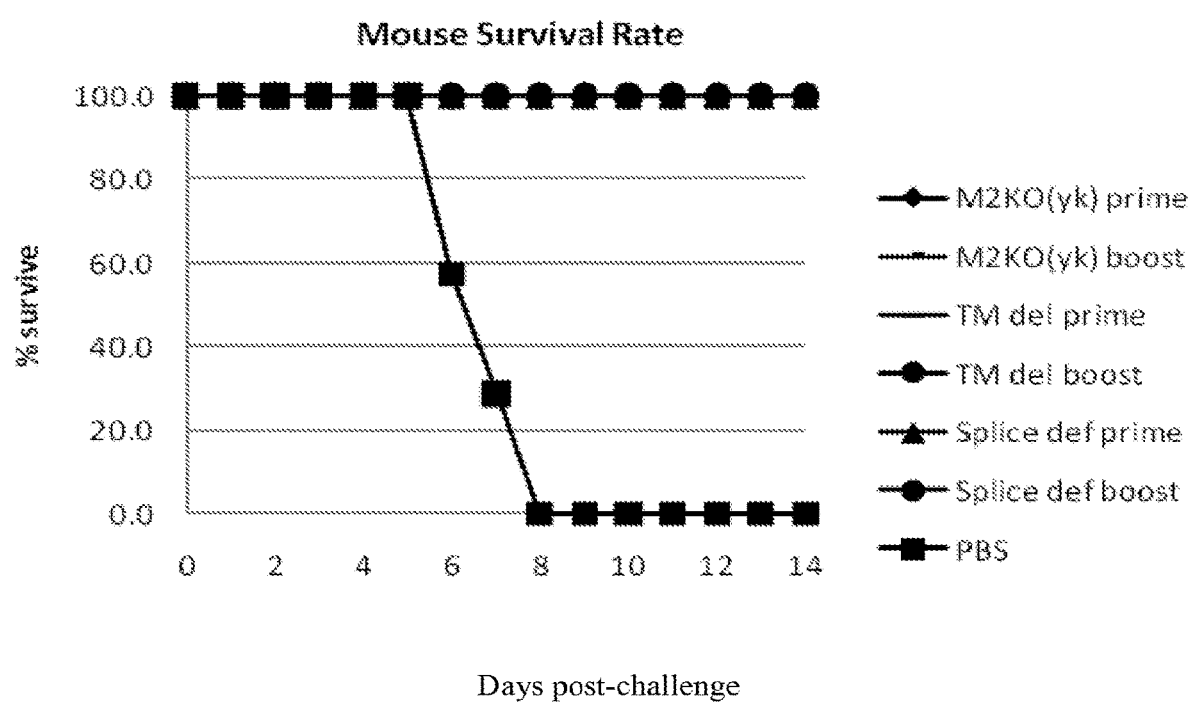
FIG. 9 is a chart showing mouse survival after influenza challenge, post-inoculation with M2KO variants.

49 days after the first inoculation (3 weeks after the boost), the mice were challenged with a lethal dose of PR8 virus (40 mouse 50% lethal dose ($MLD_{50}$)). As shown in FIG. 8 and FIG. 9, all mice vaccinated with the M2KO variants survived the challenge and lost no weight. The control mice that were given only PBS, however, lost body weight and did not survive 8 days past the challenge date. On day 3 after the challenge, lungs and NT were obtained and virus titers determined in MDCK cells by plaque assay. As depicted in Table 11, lung virus titers in M2KO variants were at least one log lower than titers in naïve control PBS. And almost no viruses were detected in nasal turbinates in M2KO variants groups but more than 100,000 PFU/g were detected in the naïve control PBS group, indicating that the M2 mutant vaccines confer protection and limits the replication of the challenge virus.

TABLE 11

| Virus Titer (log10 PFU/g) in Mouse Tissue After Challenge | | |
|---|---|---|
| | Lung | Nasal Turbinates |
| M2KO (yk) | 6.1, 5.9, ND | 1.7, ND, ND |
| M2KO (ΔTM) | 5.8 ± 0.25 | 2.5, ND, ND |
| M2KO (splice def) | ND, ND, ND | ND, ND, ND |
| PBS | 7.9 ± 0.27 | 5.3 ± 0.55 |

Figure 16:
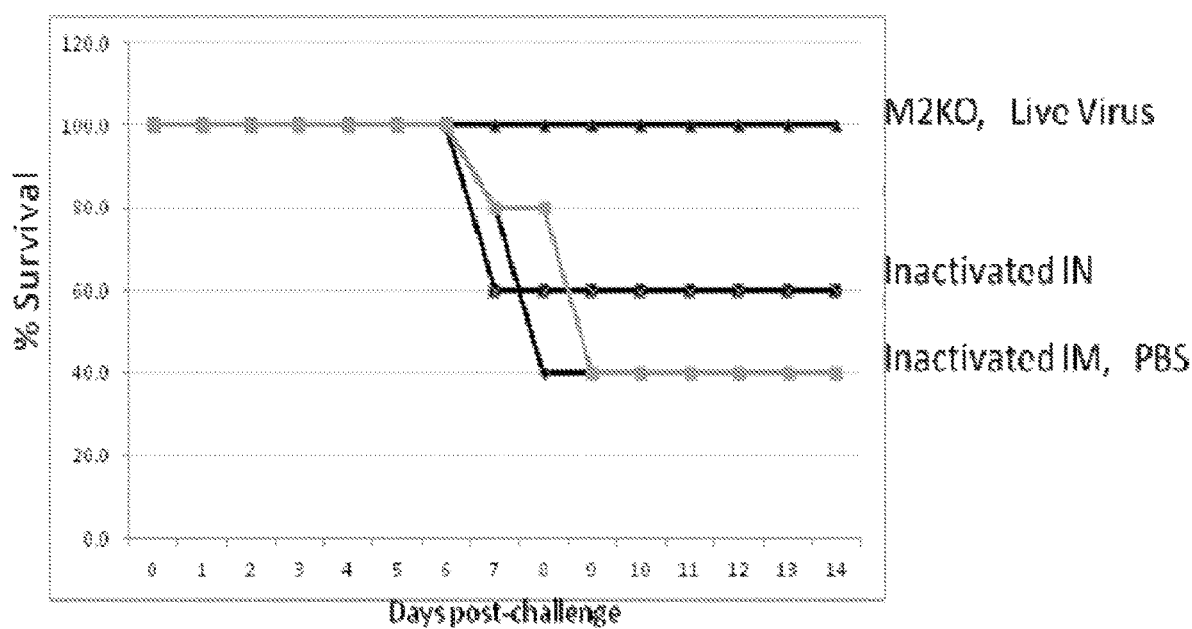
FIG. 16 is a chart showing % survival post challenge for mice infected with a heterosubtypic virus.

In another experiment, six weeks after immunization, the M2KO(ΔTM) groups were challenged with homosubtypic or heterosubtypic influenza viruses. Mice were challenged with Aichi (H3N2) virus and scored for survival for 14 days. Results for the heterotypic challenge are shown in FIG. 16.

Example 7: Intradermal Vaccine Delivery

An experiment was performed to show that intradermal vaccine delivery/immunizing will protect a subject from influenza. BALB/c female, 6-7 weeks old mice (5 per group) (Harland Laboratories) were inoculated either intranasally (IN), intramuscularly (IM) or intradermally (ID) with PR8 virus ($3.5 \times 10^7$ pfu) at a concentration of $1.8 \times 10^1$, $1.8 \times 10^2$, $1.8 \times 10^3$ or $1.8 \times 10^4$ pfu (50 µl) per mouse. Control mice were also given PBS through the three different routes of administration. Body weight and survival were monitored for 14 days after inoculation. For the mouse experiments, allergy syringes with intradermal bevel needles were used.

Most vaccines are administered by intramuscular or subcutaneous injection using conventional needles and syringes. However, recent studies demonstrate that intradermal vaccine delivery achieves better immunogenicity than intramuscular or subcutaneous administration. Intradermal vaccination delivers antigen directly to the enriched skin immune system and has been shown to be effective for a range of vaccines, including rabies, hepatitis B and influenza. Intradermal delivery may also provide dose sparing, achieving the same immune response using less vaccine than required with intramuscular injection. The current state-of-the-art for intradermal delivery (using conventional needles and syringes) is the Mantoux technique, which requires extensive training, is difficult to perform, and often results in misdirected (subcutaneous) or incomplete administration. The lack of suitable delivery devices has hampered intradermal vaccination research and product development even though superior immune responses with this administration route have been documented.

Figure 10:
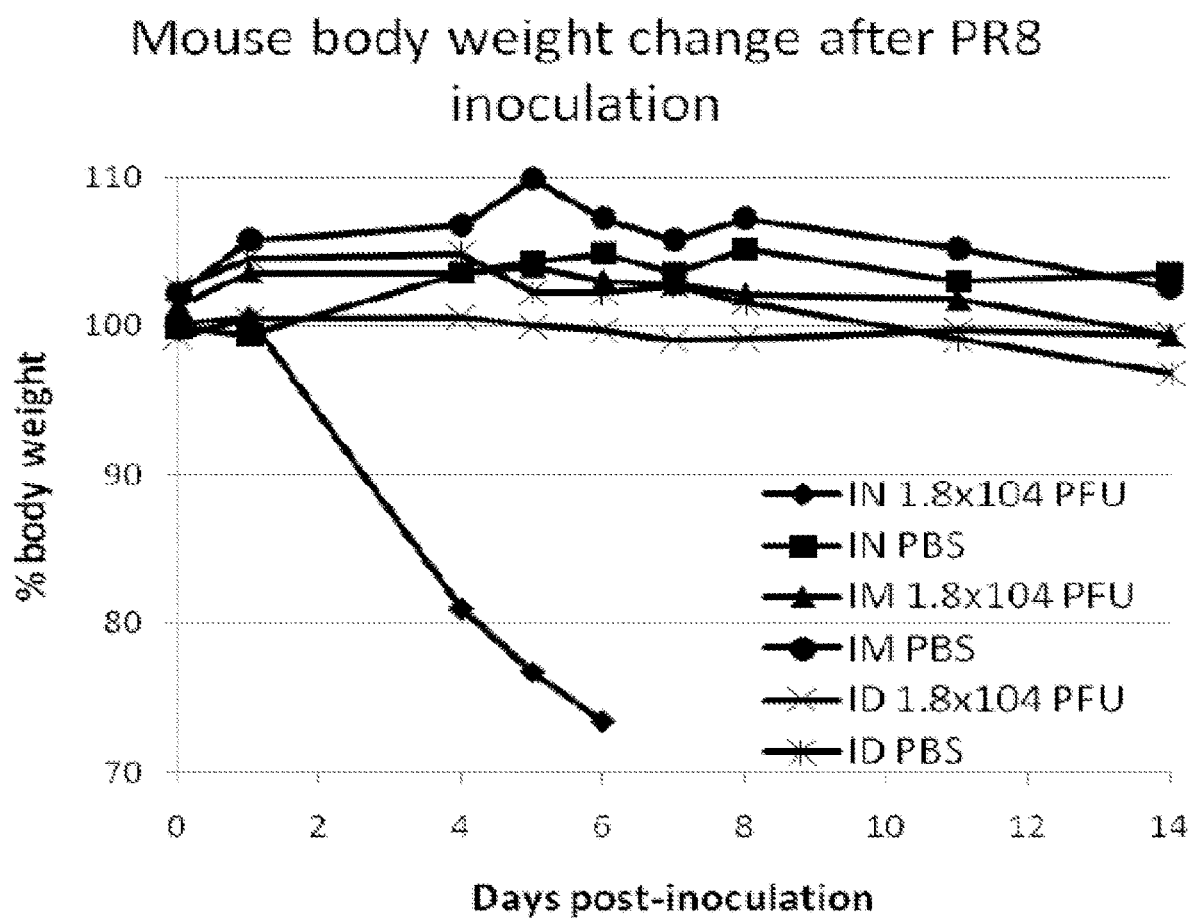
FIG. 10 is a chart showing the change in mouse body weight after inoculation with PR8 intranasally (IN), intradermally (ID) or intramuscularly (IM).

As shown in Table 12, IN-inoculated mice succumbed to influenza infection at the higher doses of $1.8 \times 10^3$ and $1.8 \times 10^4$ pfu per mouse, with complete survival only at the lowest dose of $1.8 \times 10^1$. However, IM- and ID-inoculated mice at all dosages survived. Table 13 shows the median lethal dose for mice in the IN-inoculated group ($MLD_{50}$). FIG. 10 shows that IM- and ID-inoculated mice inoculated with $1.8 \times 10^4$ pfu of the virus displayed no change in body weight, and shows the lack of survival for IN-inoculated mice inoculated with $1.8 \times 10^4$ pfu of virus.

TABLE 12

Mice survival after PR8 inoculation

| Virus Dose (pfu) | Route of Administration | | |
|---|---|---|---|
| | IM | ID | IN |
| $1.8 \times 10^1$ | 5/5 | 5/5 | 5/5 |
| $1.8 \times 10^2$ | 5/5 | 5/5 | 1/5 |
| $1.8 \times 10^3$ | 5/5 | 5/5 | 0/5 |
| $1.8 \times 10^4$ | 5/5 | 5/5 | 0/5 |
| PBS | 5/5 | 5/5 | 5/5 |

TABLE 13

Median lethal dose for mice ($MLD_{50}$).

| Route | $MLD_{50}$ (pfu[a]/mouse) |
|---|---|
| IN | 76 |
| IM | $>1.8 \times 10^4$ |
| ID | $>1.8 \times 10^4$ |

[a]pfu: plaque forming unit.

Figure 11A:
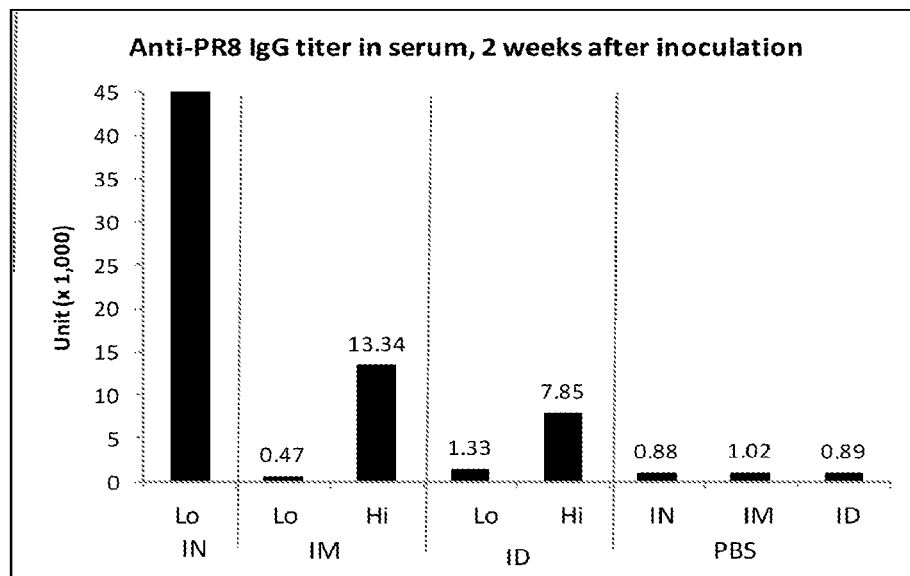
FIG. 11A is a chart showing antibody titer in serum, collected at 2 weeks post-inoculation with PR8, from mouse with $1.8 \times 10^1$ pfu (Lo) or $1.8 \times 10^4$ pfu (Hi) concentration of virus.
Figure 11B:
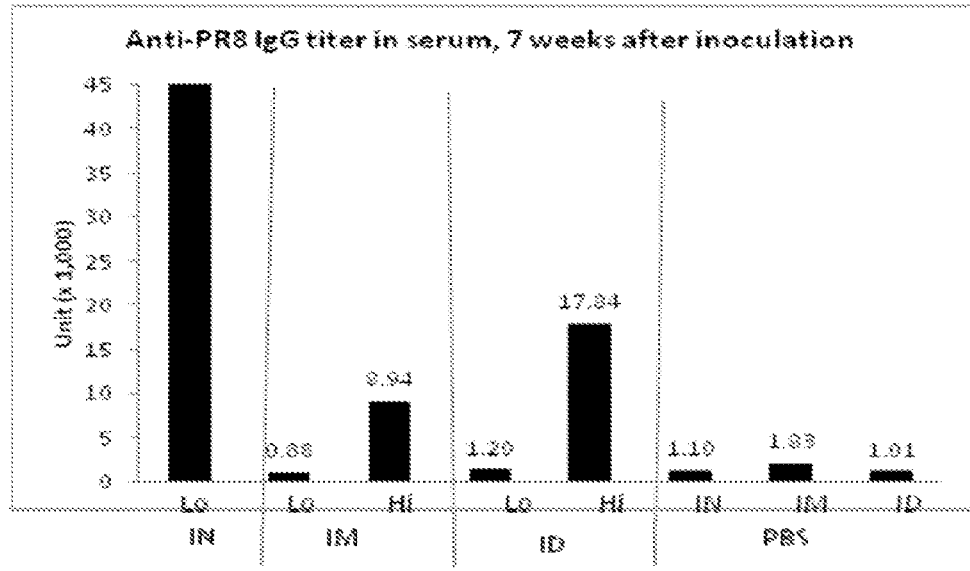
FIG. 11B is a chart showing antibody titer in serum, collected at 7 weeks post-inoculation with PR8, from mouse with $1.8 \times 10^1$ pfu (Lo) or $1.8 \times 10^4$ pfu (Hi) concentration of vaccine.

Serum was collected at 2 weeks (FIG. 11A) and 7 weeks (FIG. 11B) after inoculation and evaluated for anti-PR8 IgG antibody as determined by an ELISA. "Hi" represents $1.8 \times 10^4$ pfu inoculations, and "Lo" represents $1.8 \times 10^1$ pfu. The responses of the IN-, IM- and ID-inoculated mice at both time periods are similar. At each time period, IN-inoculated mice presented the highest number of antibodies. Only IN-inoculated mice inoculated with $1.8 \times 10^1$ pfu were identified (i.e., "Lo"), because by this time, the IN-inoculated mice inoculated with higher doses had expired. IM- and ID-inoculated mice presented lower levels of antibodies than the IN-inoculated mice, although mice inoculated at the higher doses exhibited greater amounts of antibodies when compared with the control mice given only PBS. Additionally, over time, the intradermal administration route produced more antibodies than the intramuscular route, as demonstrated by the higher titer levels shown in FIG. 11B.

In another experiment, groups of IN-, IM- and ID-inoculated mice (5 mice per group, except for 4 mice in $1.8 \times 10^3$ group) were challenged 8 week after vaccination. Specifically, $1.8 \times 10^1$ IN-inoculated mice, $1.8 \times 10^3$ IM-inoculated mice, $1.8 \times 10^4$ IM-inoculated mice, $1.8 \times 10^3$ ID-inoculated mice and $1.8 \times 10^4$ ID-inoculated mice were challenged. Mice that lost more than 25% of their body weight were euthanized.

Figure 12:
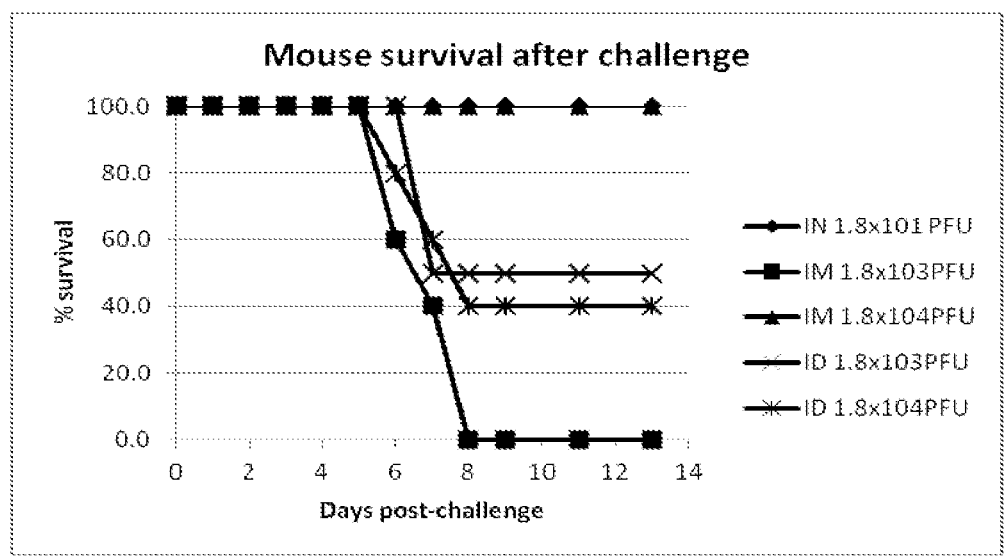
FIG. 12 is a chart showing mouse survival after influenza challenge, post-inoculation with PR8.
Figure 13:
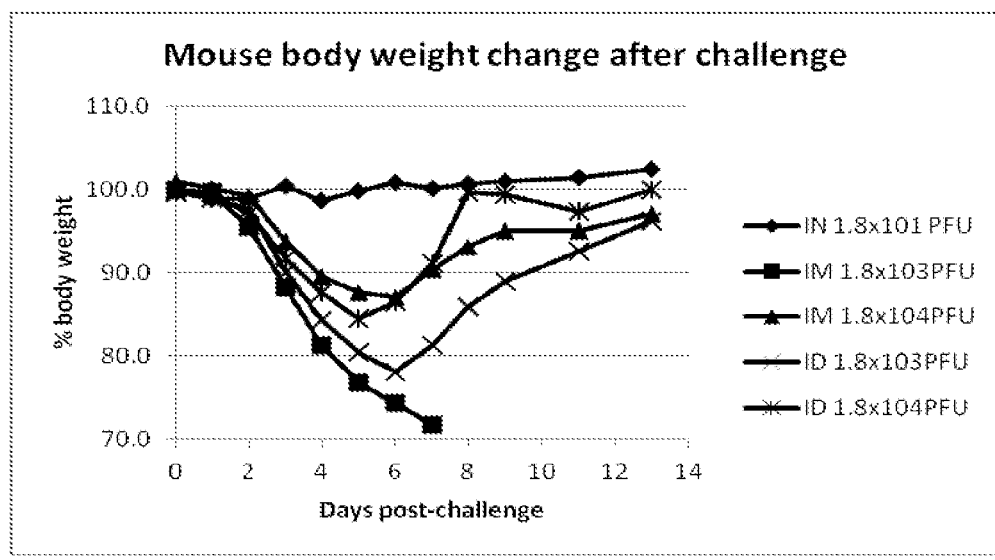
FIG. 13 is a chart showing change in mouse body weight after influenza challenge, post-inoculation with PR8.

As shown in FIG. 12, 100% of IM-inoculated mice at a dose of $1.8 \times 10^3$ did not survive 8 days after the challenge. The survival rate of all ID-inoculated mice was between 40% and 60%. The survival rate of IM-inoculated mice at $1.8 \times 10^4$, however, was 100%. FIG. 13 shows that the ID-inoculated and IM-inoculated ($1.8 \times 10^4$) groups of mice had an initial average weight loss, but ended up with a relative low weight loss from the challenge date.

Figure 14:
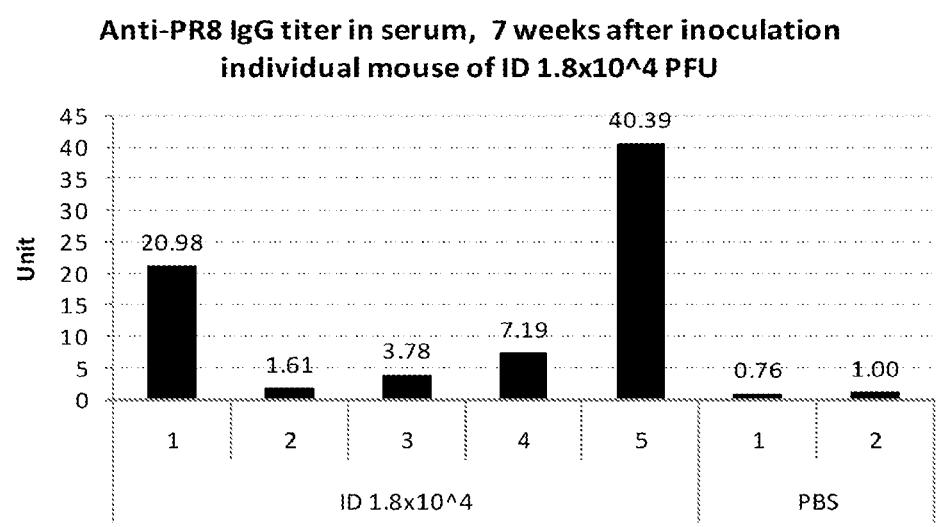
FIG. 14 is a chart showing antibody titer in serum, collected from a mouse inoculated with $1.8 \times 10^4$ pfu PR8 intradermally at 7 weeks post-inoculation.
Figure 15:
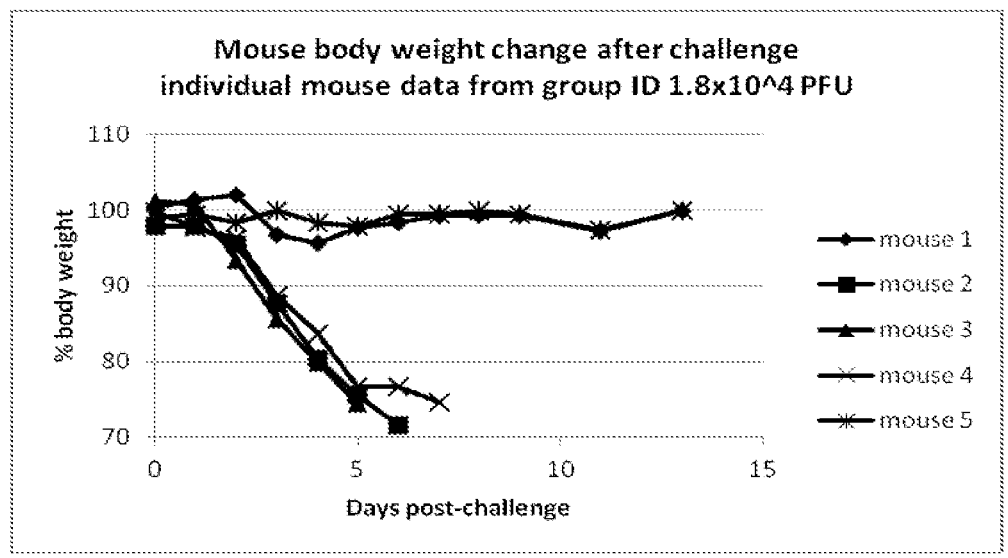
FIG. 15 is a chart showing the change in body weight of mice inoculated with $1.8 \times 10^4$ pfu PR8 intradermally.

An evaluation of the ID-inoculated mice ($1.8 \times 10^4$) showed that two mice (1 and 5 in FIG. 14 and FIG. 15), elicited a better immune response than the other mice, and further did not develop symptoms of influenza infection (e.g., body weight loss, rough fur, quietness, etc.). However, all mice in the IM-inoculated group ($1.8 \times 10^4$) showed some symptoms and lost at least 10% in body weight.

Example 8: Stability of M2KO Variants

To test the stability of M2 gene of M2KO variants in wild-type cells, the M type MDCK cells, which lacks M2 protein expression, along with M2CK cells which are M2 protein expressing MDCK cells. All M2KO variants were passageable in M2CK cells without any mutations until at least passage 10. Although, M2-1 (TM del M2KO), M2-2 (Splice def M2KO), and M2-3 (TM del+Splice def M2KO) were not able to be passaged in wild-type MDCK cells (no cytopathic effect (CPE) is seen in wild-type MDCK cells), M2KO(yk) showed CPE even after $4^{th}$ passage in MDCK cells. M segment RNAs were extracted from M2KO(yk) passage 4 in wild-type MDCK and the cDNA were sequenced. As shown in Table 14, two inserted stop codons of M2KO(yk) were edited and M2KO (yk) passage 4 in wild-type MDCK possessed full length M2 protein gene.

TABLE 14

Sequence around inserted 2 stop codons (nt 700-800 of M segment, stop codons at nt 786-791.)

| Virus | Sequence |
|---|---|
| Original M2KO(yk) | 3'CAACGGTTCAAGTGATTAATAAACTATTGCC |
| M2KO(yk) passage 2 in M2CK | 3'CAACGGTTCAAGTGATTAATAAACTATTGCC |
| M2KO(yk) passage 4 in MDCK | 3'CAACGGTTCAAGTGATTGGTGGACTGTTGCC |

Example 9: M2KO Vaccinations

To demonstrate that the M2KO vaccine can stimulate an immune response similar to a natural influenza infection, a vaccine experiment was conducted. Natural influenza infection was represented by a low inoculum of PR8 virus and the standard inactivated flu vaccine was represented by inactivated PR8 virus (Charles River) delivered the standard intramuscular route and intranasally.

Figure 17:
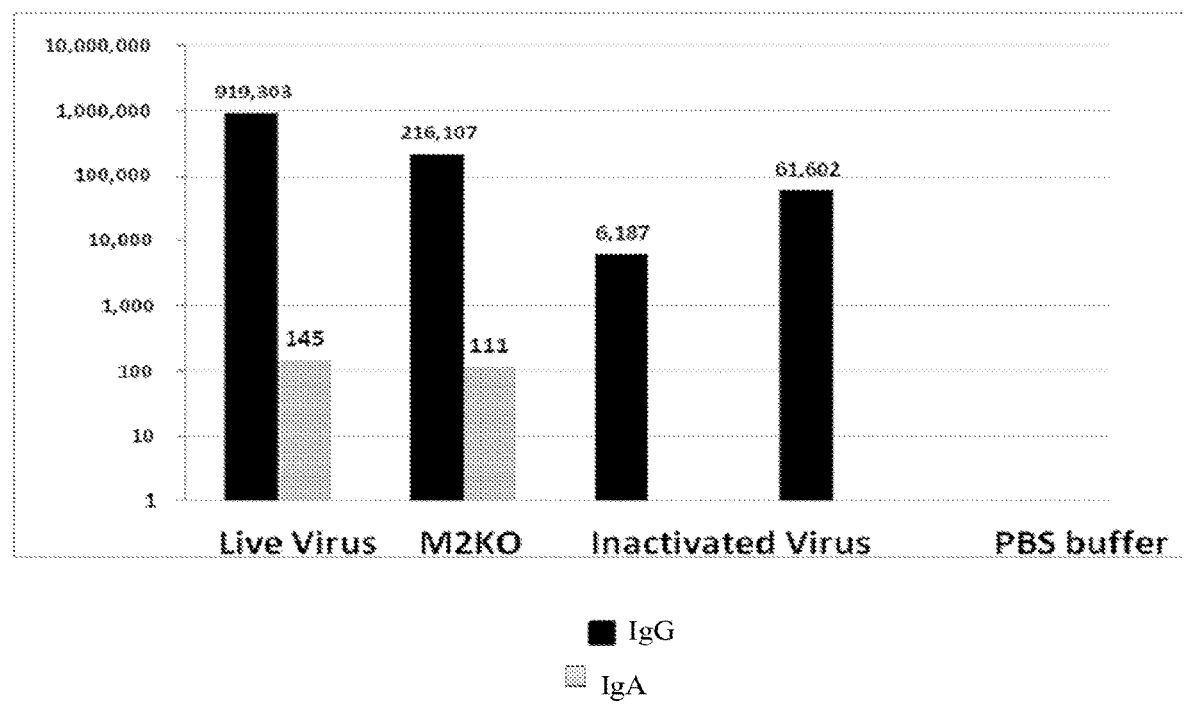
FIG. 17 is a chart showing ELISA titers of mice from different vaccination groups.

Six to seven week old BALB/c mice were immunized intranasally with live virus (10 pfu PR8), PR8 virus comprising M2KO(ΔTM) ($10^4$ pfu), or 1 µg inactivated PR8 virus, delivered both intranasally and intramuscularly. Mice given $10^4$ infectious particles of M2KO(ΔTM) intranasally lost no weight and showed no signs of infection. Furthermore, the lungs of mice treated with M2KO(ΔTM) contained no detectable infectious particles three days post-inoculation. Sera was obtained from the immunized mice on day 21 and antibody titers against the hemagglutinin were determined by a standard ELISA assay. FIG. 17 shows that anti-HA IgG titers were highest in the live virus and M2KO (ΔTM) groups relative to the inactivated vaccine groups. Mucosal IgA antibody against influenza was detected in sera only in the live PR8 or M2KO vaccinated mice.

Figure 18:
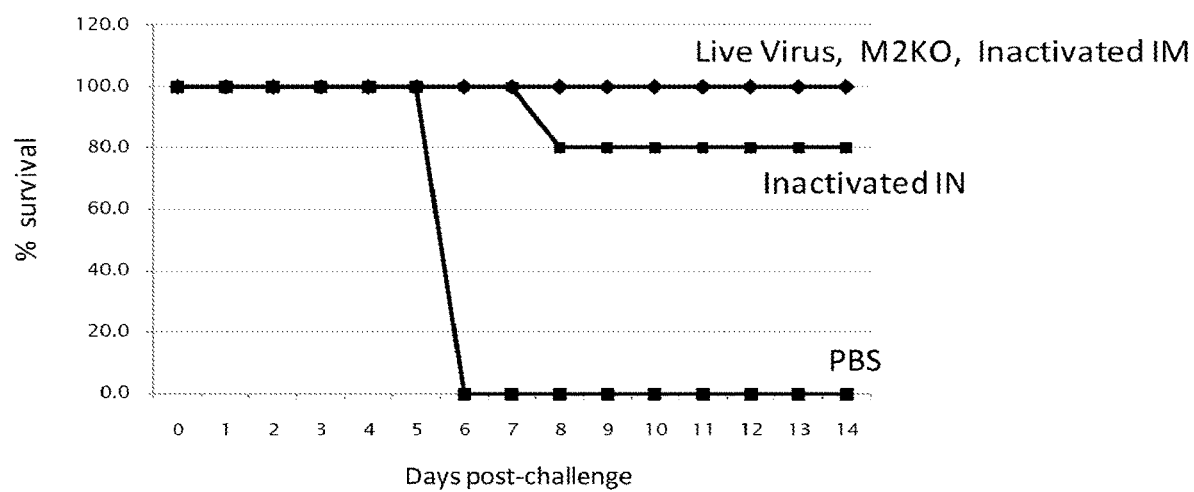
FIG. 18 is a chart showing % survival of mice after homosubtypic virus infection.
Figure 19:
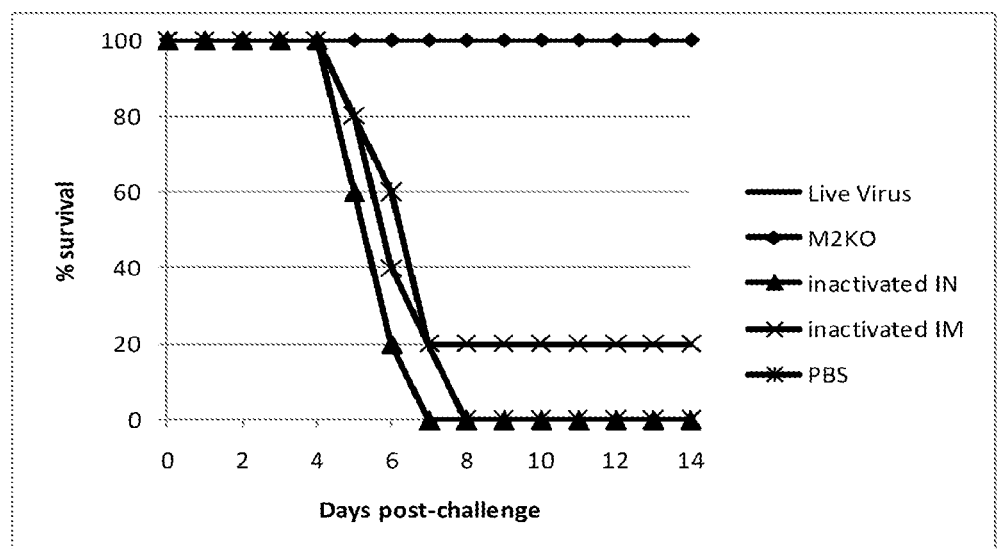
FIG. 19 is a chart showing % survival of mice after hetersubtypic virus challenge.
Figure 20A:
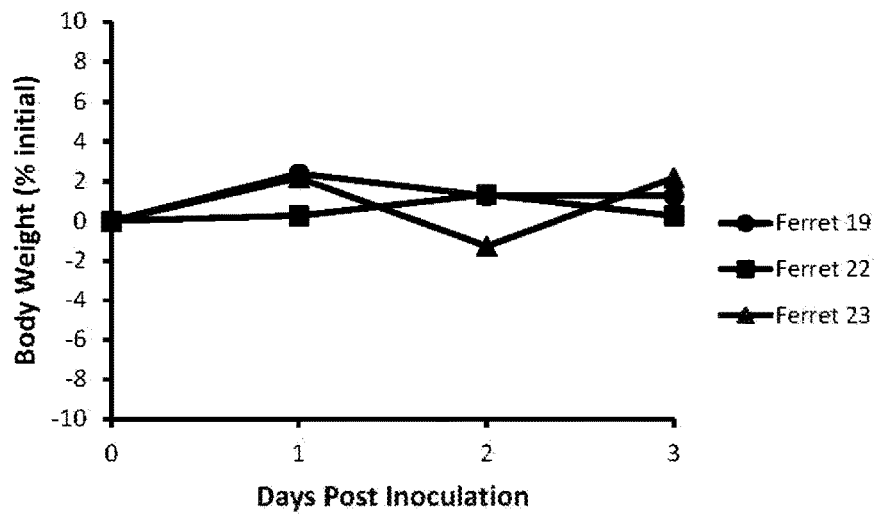
FIGS. 20A and 20B are charts showing changes in body weight of inoculated ferrets. Ferrets were inoculated with $10^7$ $TCID_{50}$ of M2KO($\Delta$TM) virus (20A) or with $10^7$ $TCID_{50}$ of A/Brisbane/10/2007 (H3N2) influenza A virus (20B). Body weight was monitored for 3 days post inoculation.
Figure 20B:
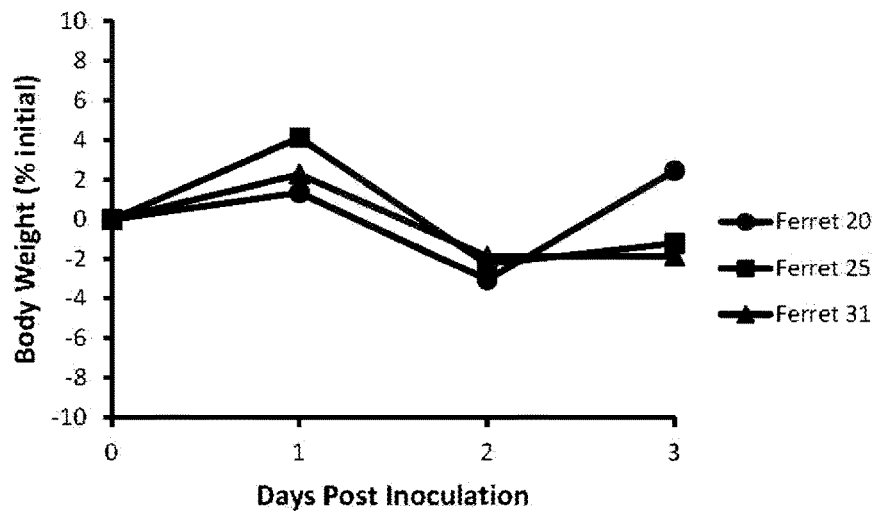
Figure 21A:
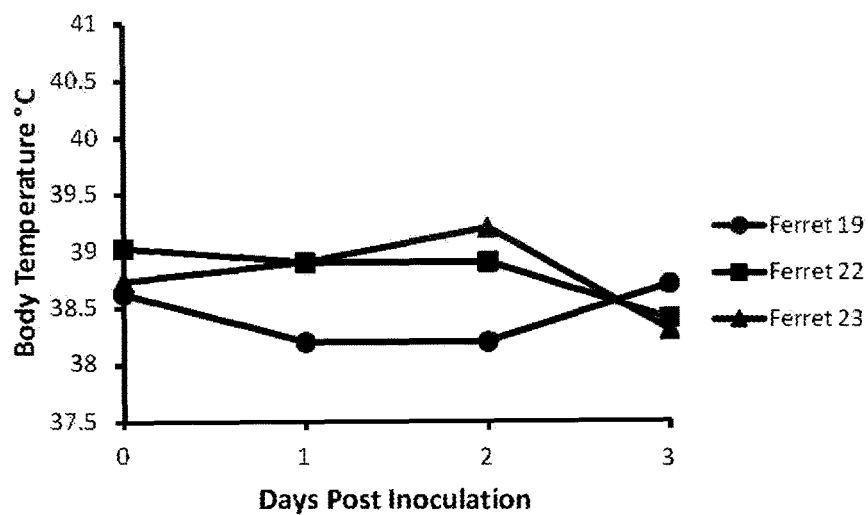
FIGS. 21A and 21B are charts showing changes in body temperature of inoculated ferrets. Ferrets were inoculated with $10^7$ $TCID_{50}$ of M2KO($\Delta$TM) virus (21A) or with $10^7$ $TCID_{50}$ of A/Brisbane/10/2007 (H3N2) influenza A virus (21B). Body temperature was monitored for 3 days post inoculation.
Figure 21B:
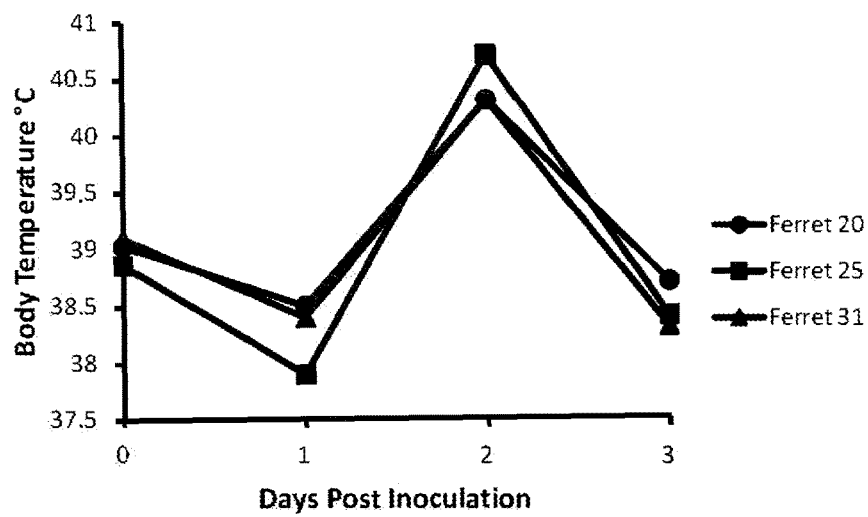

Six weeks after immunization, all groups were challenged with homosubtypic (PR8, H1N1) or heterosubtypic (Aichi, H3N2) influenza viruses. Both M2KO and inactivated vaccinations protected mice from homosubtypic virus infection (FIG. 18). However, only M2KO vaccinated mice were protected from heterosubtypic virus challenge (FIG. 19). The mice immunized with inactivated vaccine succumbed to infection similar to naïve mice.

Example 10 the M2KO(ΔTM) Virus does not Replicate in the Respiratory Tract or Other Organs Summary—This example demonstrates that the M2KO (ΔTM) virus does not replicate in the respiratory tract or disseminate to other organs in the ferret model. The M2KO (ΔTM) virus was administered intranasally to 3 male ferrets at a dose level of $1\times10^7$ $TCID_{50}$. As a control, second group of 3 male ferrets was administered A/Brisbane/10/2007 (H3N2) influenza A virus intranasally at a dose of $1\times10^7$ $TCID_{50}$. Following virus inoculation, ferrets were observed until Day 3 post inoculation for mortality, with body weights, body temperatures and clinical signs measured daily. Necropsy was performed on all animals 3 days post inoculation. Organs were collected for histopathology and viral titers.

The control group receiving A/Brisbane/10/2007 (H3N2) exhibited a transient reduction in weight and an increase in body temperature 2 days after inoculation which was not observed in the M2KO(ΔTM) group. Activity levels were also reduced in the A/Brisbane/10/2007 group with sneezing observed on days 2-3 post infection. No changes in activity level or clinical signs associated with virus exposure were observed in the M2KO(ΔTM) group. Histopathological analysis revealed changes in the nasal turbinates in animals exposed to influenza A/Brisbane/10/2007 (H3N2) that were not seen in ferrets exposed to the M2KO(ΔTM) virus. Exposure to A/Brisbane/10/2007 resulted in atrophy of respiratory epithelium, infiltrates of neutrophils and edema in the nasal turbinates. No other organ was affected by the virus inoculation. Under the conditions of the experiment, the M2KO(ΔTM) virus did not induce clinical signs of infection or result in histological changes in the organs analyzed.

Materials and Methods

A. Vaccine Material and Control Virus: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007(H3N2). The A/Brisbane/10/2007 (H3N2) wild type virus served as the control virus and was supplied by IITRI. The viruses were kept frozen at −65° C. until used.

B. Test Article and Positive Control Dose Formulation: The M2KO(ΔTM) virus dosing solution of $1\times10^7$ $TCID_{50}$/mL per 316 µL was prepared by diluting 8 µL of $1\times10^{10}$ $TCID_{50}$/mL into 2.528 mL PBS. The A/Brisbane/10/2007 (H3N2) at a titer of $1\times10^7$ $TCID_{50}$/mL per 316 was used undiluted.

C. Animals and Animal Care: Eight male ferrets were purchased from Triple F Farms and six of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least once daily. Fluorescent lighting in the animal rooms was maintained on a 12-hr light/dark cycle. Animal room temperature and relative humidity were within respective protocol limits and ranged from 22.0 to 25.0° C. and 33 to 56%, respectively, during the study.

D. Animal Quarantine and Randomization: The ferrets were held in quarantine for five days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: All animal procedures were performed in an animal biosafety level-2 facility in accordance with the protocols approved by the animal care and use committee at IIT Research Institute. 6 male ferrets (Triple F Farms, Sayre Pa.), 4 months of age at the time of study initiation were utilized for the study. Prior to infection, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation via the jugular vein, and serum tested for influenza antibodies. Study animals free of influenza antibodies were randomized and divided into two groups (3 ferrets/group) as shown in Table 15. A group of 3 ferrets was anesthetized and inoculated intranasally with a single dose of 316 μL at $1 \times 10^7$ TCID$_{50}$ of M2KO(ΔTM) virus. A control group (3 ferrets) was inoculated with 316 μL at $1 \times 10^7$ TCID$_{50}$ of A/Brisbane/10/2007 (H3N2). Ferrets were observed daily to monitor body weight, body temperature and clinical symptoms. On Day 3 post-inoculation, ferrets (3 ferrets per group) were euthanized and necropsied. The following tissue samples were collected: nasal turbinates, trachea, lungs, kidneys, pancreas, olfactory bulbs, brains, livers, spleens, small and large intestines. One part of the collected samples was fixed with buffered neutral formalin for histological evaluation and the other part of the samples were stored at −65° C. for virus titration.

TABLE 15

Immunization and sample collection schedule

| Group | Dose | N | Organ collection (days post infection) |
|---|---|---|---|
| M2KO | $1 \times 10^7$ TCID$_{50}$ | 3 | 3 |
| Brisbane/10 | $1 \times 10^7$ TCID$_{50}$ | 3 | 3 |

F. Virus Inoculation: Ferrets were inoculated with either the M2KO(ΔTM) virus or wild type A/Brisbane/10/2007 (H3N2) influenza A virus. A vial of frozen stock was thawed and diluted to the appropriate concentration in phosphate buffered saline solution. Ferrets were anesthetized with ketamine/xylazine and the virus dose administered intranasally in a volume of 316 μL for the M2KO(ΔTM) virus and 316 μL for the A/Brisbane/10/2007 (H3N2) virus. To confirm the inoculation titer of the A/Brisbane/10/2007 (H3N2) virus, a TCID$_{50}$ assay was performed at IITRI on a portion of the prepared viral challenge solution. The viral titer assay was performed according to Illinois Institute of Technology Research Institute (IITRI) Standard Operating Procedures.

G. Moribundity/Mortality Observations: Following challenge, all animals were observed twice daily for mortality or evidence of moribundity. Animals were observed for 3 days post-challenge. Animals were euthanized by overdose with Sodium Pentobarbital 150 mg/kg, administered intravenously.

H. Body Weights and Body Weight Change: Body weights of animals were recorded upon receipt (random 10% sample), at randomization (Day −3 to 0), and daily after virus inoculation.

I. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," *J. Virol*, Methods 24:27-34 (1989), was used to assess the activity level as follows: 0, alert and playful; 1, alert but playful only when stimulated; 2, alert but not playful when stimulated; and 3, neither alert nor playful when stimulated. A relative inactivity index (RII) was calculated as the mean score per group of ferrets per observation (day) over the duration of the study.

J. Euthanasia: Study animals were euthanized by an intravenous dose of sodium pentobarbital 150 mg/kg. Death was confirmed by absence of observable heartbeat and respiration. Necropsies were performed on all study animals.

K. Necropsy: Nasal turbinates, trachea, lungs, kidneys, pancreas, olfactory bulbs, brain, liver, spleen, small and large intestines were harvested. One portion of each tissue was fixed in formalin and the other portion given to IITRI staff for freezing and storage. Tissue harvested for titers are: right nasal turbinates, upper 1/3 of trachea, right cranial lung lobe, right kidney, right arm of pancreas (near duodenum), right olfactory bulb, right brain, right lateral lobe of liver, right half of spleen (end of spleen seen on opening the abdominal cavity), small intestine and large intestine.

L. Histopathological analysis: Tissues were processed through to paraffin blocks, sectioned at approximately 5-microns thickness, and stained with hematoxylin and eosin (H & E).

M. Serum Collection: Pre-vaccination (Day −3) serum was collected from all ferrets. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected. Individual pre-inoculation serum samples were collected and two aliquots made from each sample. One aliquot was tested prior to the initiation of the study to confirm ferrets are free of antibodies to influenza A viruses and one aliquot of the serum stored at −65° C.

N. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% chicken red blood cells were added to each sample and incubated. Presence or absence of hemagglutination was then scored.

O. Virus Titers: The concentration of infectious virus in the pre- and post-challenge virus inoculum samples was determined by $TCID_{50}$ in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Penicillin/Streptomycin, 0.1% Gentamicin, 3% $NaCO_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 100 L was transferred into respective wells of a 96-well plate which contained a monolayer of MDCK cells. Plates were incubated at 37° C.±2° C. in 5±2% $CO_2$ 70% humidity. After 48 hours, the wells were observed for cytopathogenic effect (CPE). Supernatant from each well (50 μl) was transferred to a 96 well plate and the hemagglutination (HA) activity determined and recorded. The HA activity of the supernatant was assessed by HA assay with 0.5% packed turkey red blood cells (cRBCs). $TCID_{50}$ titers were calculated using the method of Reed LJ and Muench H, "A simple method for estimating 50% endpoints," *Am. J. Hygiene* 27: 493-497 (1938).

P. Data Analysis: Body weights and body weight gains (losses) and changes in body temperature were determined for each individual animal expressed as mean and standard deviations of the mean for each test group.

Results

After inoculation with either the M2KO(ΔTM) virus or A/Brisbane/10/2007 (H3N2) influenza A virus, ferrets were monitored for survival and clinical signs of infection. Results are presented in Table 16A and 16B. All ferrets survived infection with M2KO(ΔTM) virus and A/Brisbane/10/2007 (H3N2). Ferrets inoculated with A/Brisbane/10/2007 presented respiratory signs (sneezing) on Day 2 and 3. The relative inactivity index of ferrets inoculated with A/Brisbane/10/2007 was 0.67; whereas ferrets inoculated with M2KO(ΔTM) showed no reduction activity level with a relative inactivity index of 0.0.

Changes in body weight and temperature after virus inoculation are shown in FIGS. 20A and 20B and FIGS. 21A and 21B. After inoculation with A/Brisbane/10/2007 (H3N2), a 2-3% loss of body weight was observed on Day 2 post inoculation in all animals. Minimal to zero weight loss was observed in ferrets inoculated with the M2KO (ΔTM) virus. One M2KO(ΔTM) inoculated ferret exhibited weight loss on Day 2 post inoculation of 1%. Elevated body temperatures of 40.3-40.7° C. were observed in ferrets inoculated with A/Brisbane 10/2007 on Day 2 post inoculation. Body temperatures returned to normal range by Day 3. Body temperatures for M2KO(ΔTM) inoculated ferrets remained in normal range throughout the duration of the study. To determine if the M2KO(ΔTM) virus would replicate in the respiratory tract or other organs and induce pathology, tissues of ferrets were histologically examined on day 3 post inoculation and compared to those from ferrets inoculated with A/Brisbane/10/2007. In ferrets inoculated with A/Brisbane/10/2007, pathology was observed only in the nasal turbinates. Atrophy of respiratory epithelium, infiltrates of neutrophils and edema were observed in the nasal turbinates. No histopathological changes associated with viral infection were observed in ferrets inoculated with the M2KO(ΔTM) virus. The concentrations of pre- and post-challenge virus dosing solutions were $10^{7.5}$ $TCID_{50}$/mL and $10^{7.75}$ $TCID_{50}$/mL, respectively, indicating good stability of the challenge material throughout administration.

TABLE 16A

Effect of virus inoculation on survival and clinical signs of infection in ferrets.

| Group | N | Serum HI Titer[a] | Total number dead | Respiratory signs (observed day of onset) | Loss of Appetite | Lethargy (RII)[c] |
|---|---|---|---|---|---|---|
| M2KO | 3 | <10 | 0/3 | 0/3 | 0/3 | 0 |
| Brisbane/10 | 3 | <10 | 0/3 | 2/3 (2) | 0/3 | 0.67 |

[a]Hemagglutination inhibition (HI) antibody titers to homologous virus in ferret serum prior to virus inoculation.
[b]Clinical signs were observed for 3 days after virus inoculation. Except for lethargy, findings for clinical signs are given as no. of ferrets with sign/total no. Respiratory signs included sneezing.
[c]Determined twice daily for 3 days of observation based on the scoring system and was calculated as the mean score per group of ferrets per observation (day) over the 3-day period. The relative inactivity index before inoculation was 0.

TABLE 16B

M2KO(ΔTM) Does Not Replicate in Ferret Respiratory Organs Harvested On Day 3
Virus Titer (log pfu/g)

| | Brisbane/10 | M2KO(ΔTM) |
|---|---|---|
| Nasal Turbinates | 5.43 | 0 |
| Lung | 0 | 0 |

Conclusion

This example shows that by Day 3 post inoculation, the M2KO(ΔTM) virus does not induce clinical signs of disease or histopathological changes associated with infection of wild type virus. This shows that the M2KO(ΔTM) virus of the present technology is useful for intranasal influenza vaccines.

Example 11: Immune Response and Protective Effects M2KO(ΔTM) Virus Relative to Other Vaccines Summary—This example demonstrates the immune response elicited by the M2KO(ΔTM) vaccine and the protective effects of the vaccine in the ferret model. The M2KO(ΔTM) virus was administered intransally to 12 male ferrets at a dose level of $1\times10^7$ $TCID_{50}$. As a control, a second group of 12 male ferrets was administered the FM #6 virus intranasally at a dose of $1\times10^7$ $TCID_{50}$. A third group of ferrets was administered OPTI-MEM™ as a placebo control. A prime only or prime-boost vaccination regimen was utilized for each treatment group. Ferrets receiving the prime-boost vaccination regimen were administered the prime vaccine (Day 0) and the boost vaccination 28 days later (Day 28). Ferrets receiving only the prime vaccine were administered a single vaccination on the same day as the booster vaccine was given to the prime-boost ferrets (Day 28). Following each vaccination, ferrets were observed for 14 days post inoculation for mortality, with body weights, body temperatures and clinical signs measured daily. Nasal washes were collected from ferrets on days 1, 3, 5, 7 and 9 post-prime vaccination to look for viral shedding. Nasal washes and serum were collected weekly from all ferrets post-vaccination to evaluate antibody levels over time.

All animals were challenged intranasally on Day 56 with $1\times10^7$ TCID$_{50}$ of A/Brisbane/10/2007 (H3N2). Following challenge, ferrets were monitored for 14 days post inoculation for mortality, with body weights, body temperatures and clinical signs measured daily. Nasal washes were collected on days 1, 3, 5, 7, 9 and 14 post challenge from ferrets in each group for viral titers. Additionally, serum was collected post-challenge (day 70) from surviving ferrets for analysis. Necropsy was performed on 3 ferrets per group 3 days post challenge. Organs were collected for histopathology and viral titers.

No vaccine related adverse events were observed among the 5 groups. After challenge, the placebo control group exhibited an increase in body temperature 2 days after challenge and a reduction in weight. A reduction in weight was also observed in M2KO(ΔTM) and FM #6 vaccinated groups; however, the reduction was to less than that observed in the OPTI-MEM™ group. Activity levels were not reduced in any groups; however sneezing was observed in all groups after challenge. Histopathological analysis revealed an increase in severity of mixed cell infiltrates in the lung of vaccinated ferrets when compared to the lung infiltrates in the OPTI-MEM™ control group. In the nasal turbinates, animals receiving a prime or prime plus boost regimen of either M2KO(ΔTM) or FM #6 had lower severity of atrophy of respiratory epithelium when compared to the OPTI-MEM™ control group. Vaccination with the M2KO (ΔTM) virus appeared to provides similar protection against viral challenge as the FM #6 virus.

Materials and Methods

A. Vaccine Material: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007 (H3N2). The FM #6 virus is clone #6 of the A/Uruguay/716/2007 (H3N2) influenza A virus from FluMist® (2009-2010 formula). The M2KO(ΔTM) virus and FM #6 virus were administered intranasally to the animals in a 316 μL dose of $1\times10^7$ $TCID_{50}$ (50% Tissue Culture Infectious Doses).

B. Test Article and Positive Control Dose Formulation: The M2KO(ΔTM) virus dosing solution of $1\times10^7$ $TCID_{50}$/mL per 316 μL was prepared by diluting 120 μL of $1\times10^9$ $TCID_{50}$/mL into 3.680 mL PBS. The FM #6 virus at a titer of $1\times10^7$ $TCID_{50}$/mL per 316 μL was prepared by diluting 120 μL of $1\times10^9$ $TCID_{50}$/mL into 3.680 mL PBS.

C. Animals and Animal Care: Thirty-six male ferrets were purchased from Triple F Farms and 30 of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least three time per week. Fluorescent lighting in the animal rooms was maintained on a 12-hr light/dark cycle. Animal room temperature and relative humidity were within respective protocol limits and ranged from 20.0 to 25.0° C. and 30 to 63%, respectively, during the study.

D. Animal Quarantine and Randomization: The ferrets were held in quarantine for seven days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: To assess the M2KO(ΔTM) vaccine efficacy, ferrets were immunized with M2KO(ΔTM) virus, cold adapted live attenuated virus (FM #6) or mock immunized by medium (OPTI-MEM™). The animals body weight, body temperature and clinical symptoms were monitored and immunological responses evaluated. 30 male ferrets (Triple F Farms, Sayre Pa.), 4 months of age at the time of study initiation were utilized for the study. All animal procedures were performed in an animal biosafety level-2 or biosafety level-3 facility in accordance with the protocols approved by the animal care and use committee at IIT Research Institute. Prior to inoculation, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation, and serum tested for influenza antibodies. Only ferrets with HAI (hemagglutination inhibition) titers 40 to A/Brisbane/10/2007 (H3N2) were considered seronegative and used in this study. Study animals were randomized and divided into 5 groups (6 ferrets/group) as shown in Table 17. Two groups (1 & 3) received the M2KO(ΔTM) virus and 2 groups (2 & 4) received the FM #6 virus. One group (5) was mock immunized with OPTI-MEM™. Within each vaccine group, ferrets were divided into two vaccine regimens, six receiving a prime vaccination only (Prime only) and six receiving a prime vaccination followed by a booster vaccine 28 days after prime vaccination (Prime/Boost). Prime/Boost Groups: Ferrets were inoculated intranasally with a single dose of 316 μL of $1\times10^7$ $TCID_{50}$ of M2KO(ΔTM) virus on days 0 and 28. Control groups were inoculated intranasally with 316 μL of $1\times10^7$ $TCID_{50}$ (same dose as M2KO(ΔTM)) of FM #6 or mock inoculated with 316 μL of OPTI-MEM™ on days 0 and 28. Ferret body temperatures, weights, and clinical symptoms were monitored daily for 14 days post-inoculations. Nasal washes were collected from all ferrets, including OPTI-MEM™ control group, on days 1, 3, 5, 7, 9 and 14 post prime vaccination for virus titration in cells and on days 21 and 49 for antibody titration. Nasal wash samples were kept at −65° C. Blood was collected prior to inoculation (day −3 to −5) and days 7, 14, 21 35, 42, and 49 and serum kept at −65° C. until measurement of antibody titer by ELISA and HI assay.

Prime only Groups: Ferrets were inoculated intranasally with a single dose of 316 μL of $1\times10^7$ $TCID_{50}$ of M2KO (ΔTM) virus on day 28. Control groups were inoculated intranasally with 316 μL of 1×10⁷ TCID₅₀ (same dose as M2KO(ΔTM)) of FM #6 or mock inoculated with 316 μL of OPTI-MEM™ on day 28. Ferret body temperatures, weights, and clinical symptoms were monitored daily for 14 days post-inoculation. Nasal washes were collected from all ferrets on days 29, 31, 33, 35, 37, and 42 for virus titration in cells and on day 49 for antibody titration. Nasal wash samples were kept at −65° C. Blood was collected prior to inoculation (day 23 to 25) and days 35, 42, and 49 and serum was kept at −65° C. until measurement of antibody titer by ELISA and HAI assay. All ferrets were challenged with a dose of 316 μL of 1×10⁷ TCID₅₀ of wild-type A/Brisbane/10/2007 (H3N2) influenza virus on day 56, 4 weeks after the prime/boost vaccine was administered. Ferret body weight, body temperature and clinical symptoms were monitored for 14 days after challenge and nasal washes and organs collected. Nasal washes were collected from challenged ferrets on days 1, 3, 5, 7, 9, and 14 post-challenge (days 57, 59, 61, 63, 65, and 70) and the samples kept at −65° C. for virus titration in cells. On Day 3 post-challenge (day 59), the animals (3 animals per group, total 15 animals) were euthanized and the following tissue samples collected: nasal turbinates, trachea, and lungs. One part of the collected samples was fixed with buffered neutral formalin for histological evaluation and the other part of the samples was stored at −65° C. for virus titration. Blood was collected 14 days post-challenge (day 70) and all surviving animals were euthanized.

a portion of the prepared viral challenge solution. The viral titer assay was performed according to IITRI Standard Operating Procedures.

H. Moribundity/Mortality Observations: Following challenge, all animals were observed twice daily for mortality or evidence of moribundity. Animals were observed for 14 days after vaccine inoculation and for 14 days after challenge.

I. Body Weights and Body Weight Change: Body weights were recorded within two days of receipt and at randomization. All study animals were weighed prior to inoculation, daily for 14 days following each vaccination and assessed daily for 14 days post challenge. Prior to inoculation, ferrets were monitored for 3-5 days to measure establish baseline body temperatures. Temperature readings were recorded daily for 14 days following each vaccination and recorded daily for 14 days post challenge through a transponder (BioMedic data systems, Seaford, Del.) implanted subcutaneously in each ferret. The change in temperature (in degrees Celsius) was calculated at each time point for each animal.

J. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," *J. Virol*, Methods 24:27-34 (1989), was used to assess the activity level as follows: 0, alert and playful; 1, alert but playful only when stimulated; 2, alert but

TABLE 17

Vaccination and sample collection schedule

| Group | Vaccine Virus[1] | N | Vaccination (days) | Nasal Washes[2] (days) | Challenge (day) | Nasal Washes (days) | Organs[3] n = 3 (day) | Serum collections |
|---|---|---|---|---|---|---|---|---|
| | | | | Prime only | | | | |
| 1 | M2KO | 6 | 28 | 29, 31, 33, 35, 37, 42, 49 | 56 | 57, 59, 61, 63, 65, 70 | 59 | 35, 42, 49, 70 |
| 2 | FM#6 | 6 | 28 | 29, 31, 33, 35, 37, 42, 49 | 56 | 57, 59, 61, 63, 65, 70 | 59 | 35, 42, 49, 70 |
| | | | | Prime/Boost | | | | |
| 3 | M2KO | 6 | 0, 28 | 1, 3, 5, 7, 9, 14, 21, 49 | 56 | 57, 59, 61, 63, 65, 70 | 59 | 7, 14, 21, 35, 42, 49, 70 |
| 4 | FM#6 | 6 | 0, 28 | 1, 3, 5, 7, 9, 14, 21, 49 | 56 | 57, 59, 61, 63, 65, 70 | 59 | 7, 14, 21, 35, 42, 49, 70 |
| 5 | Vehicle (Control) | 6 | 0, 28 | 1, 3, 5, 7, 9, 14, 21, 49 | 56 | 57, 59, 61, 63, 65, 70 | 59 | 7, 14, 21, 35, 42, 49, 70 |

[1]Intranasally inoculated with a dose of 1 × 10⁷ TCID₅₀
[2]Nasal Washes only collected from animals after prime vaccination.
[3]Organs (nasal turbinated, trachea and lung) collected from 3 ferrets per group for histology and viral titers.

F. Virus Inoculation: Ferrets were inoculated with either the M2KO(ΔTM) virus or FM #6 influenza A virus. A vial of frozen stock was thawed and diluted to the appropriate concentration in phosphate buffered saline solution. Ferrets were anesthetized with ketamine/xylazine and the virus dose administered intranasally in a volume of 316 μL for the M2KO(ΔTM) virus and 316 μL for the FM #6 virus. To confirm the inoculation titer of the M2KO(ΔTM) and FM #6 viruses, aliquots of the dosing solutions were collected prior to dosing (pre-dose) and after dosing (post-dose). The aliquots were stored at −65° C. for virus titration.

G. Challenge Virus: Influenza A virus, strain A/Brisbane/10/2007, serotype H3N2 was used to challenge the ferrets. The virus was stored at approximately −65° C. prior to use. The dose level of challenge virus used was prepared at 1×10⁷ TCID₅₀ in a volume of 316 μL. A quantitative viral infectivity assay, TCID₅₀ assay was performed at IITRI on not playful when stimulated; and 3, neither alert nor playful when stimulated. A relative inactivity index (RII) was calculated as the mean score per group of ferrets per observation (day) over the duration of the study.

K. Survival Checks: Two survival checks were performed daily on all study animals throughout the study. Both survival checks occurred simultaneously with the clinical observations. The second check was performed later within the same day.

L. Nasal Washes: Ferrets were anesthetized with a ketamine (25 mg/kg) and xylazine (2 mg/kg) mixture, and 0.5 ml of sterile PBS containing penicillin (100 U/ml), streptomycin (100 μg/ml), and gentamicin (50 μg/ml) was injected into each nostril and collected in a specimen cup when expelled by the ferret. The nasal wash was collected into a cryovial and the recovered volume recorded.

M. Euthanasia: Study animals were euthanized by an intravenous dose of sodium pentobarbital 150 mg/kg. Death was confirmed by absence of observable heartbeat and respiration.

N. Necropsy: Necropsy was performed by Charles River Laboratories, Pathology Associates (PAI). The PAI team was comprised of a supervising pathologist and two prosectors. Nasal turbinates, trachea and lungs were harvested. One portion of each tissue was fixed in formalin and the other portion given to IITRI staff for freezing and storage. Tissue harvested for titers are: right nasal turbinates, upper ⅓ of trachea and right cranial lung lobe.

O. Histopathological analysis: Following each necropsy, tissues were transported to the PAI Chicago facility. Upon receipt, partial tissues from all 15 ferrets were processed through to paraffin blocks, sectioned at approximately 5-microns thickness, and stained with hematoxylin and eosin (H & E). All paraffin H & E slides were evaluated microscopically.

P. Serum Collection: Pre-vaccination serum (days −3 to −5 for groups 3, 4, and 5, and days 23 to 25 for groups 1 and 2) serum was collected from the ferrets. Post inoculation, serum was collected on days 7, 14, 21, 35, 42, 49, and 70 from groups 3, 4, and 5. Serum was collected on days 35, 42, 49, and 70 from groups 1 and 2. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected.

Q. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% avian red blood cells were added to each sample and incubated for 30±5 minutes. Presence or absence of hemagglutination was then scored.

R. Virus Titers: The concentration of infectious virus in the pre- and post-challenge virus inoculum samples was determined by $TCID_{50}$ assay in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Pencillin/Streptomycin, 0.1% Gentamicin, 3% $NaCO_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 100 µL was transferred into respective wells of a 96-well plate which contained a monolayer of MDCK cells. Plates were incubated at 37° C.±2° C. in 5±2% $CO_2$ 70% humidity. After 48 hours, the wells were observed for cytopathogenic effect (CPE). Supernatant from each well (50 µl) was transferred to a 96 well plate and the hemagglutination (HA) activity determined and recorded. The HA activity of the supernatant was assessed by HA assay with 0.5% packed turkey red blood cells (tRBCs). $TCID_{50}$ titers were calculated using the method of Reed LJ and Muench H, "A simple method for estimating 50% endpoints," *Am. J. Hygiene* 27: 493-497 (1938).

S. Data Analysis: Body weights and body weight gains (losses) and changes in body temperature were determined for each individual animal expressed as mean and standard deviations of the mean for each test group.

Results

After intranasal vaccination with either the M2KO(ΔTM) virus or the FM #6 virus, ferrets were monitored daily for clinical signs of infection. Nasal washes were collected after prime vaccination to monitor viral shedding and serum collected to measure serum antibody titers. Results are presented in Tables 18A, 18B, and 18C.

TABLE 18A

Effect of vaccination on survival and clinical signs of infection in ferrets.

| Group | Treatment | N | Serum HI Titer[a] | Total number dead | Respiratory signs (observed day of onset) | Loss of Appetite | Lethargy (RII)[c] |
|---|---|---|---|---|---|---|---|
| | | | | Prime | | | |
| 1 | M2KO | 6 | <10 | 0/6 | 2/6 (8) | 0/6 | 0 |
| 2 | FM#6 | 6 | <10 | 0/6 | 0/6 | 0/6 | 0 |
| 3 | M2KO | 6 | <10 | 0/6 | 0/6 | 0/6 | 0.07 |
| 4 | FM#6 | 6 | <10 | 0/6 | 0/6 | 0/6 | 0.29 |
| 5 | Vehicle (Control) | 6 | <10 | 0/6 | 0/6 | 0/6 | 0 |
| | | | | Boost | | | |
| 3 | M2KO | 6 | <10 | 0/6 | 0/6 | 0/6 | 0 |
| 4 | FM#6 | 6 | <10 | 0/6 | 2/6 (7) | 0/6 | 0 |

TABLE 18A-continued

Effect of vaccination on survival and clinical signs of infection in ferrets.

| | | | | | Clinical signs[b] | | |
|---|---|---|---|---|---|---|---|
| Group | Treatment | N | Serum HI Titer[a] | Total number dead | Respiratory signs (observed day of onset) | Loss of Appetite | Lethargy (RII)[c] |
| 5 | Vehicle (Control) | 6 | <10 | 0/6 | 2/6 (4) | 0/6 | 0 |

[a]Hemagglutination inhibition (HI) antibody titers to homologous virus in ferret serum prior to virus inoculation.
[b]Clinical signs were observed for 3 days after virus inoculation. Except for lethargy, findings for clinical signs are given as no. of ferrets with sign/total no. Respiratory signs included sneezing.
[c]Determined twice daily for 3 days of observation based on the scoring system and was calculated as the mean score per group of ferrets per observation (day) over the 3-day period. The relative inactivity index before inoculation was 0.

TABLE 18B

Virus Titers in Ferret Respiratory Organs After Challenge

| | Nasal Turbinates (N = 3, Log pfu/g) | Trachea (N = 3, Log pfu/g) |
|---|---|---|
| M2KO(ΔTM) prime only | 5.23 ± 0.24 | ** |
| FluMist ® prime only | 5.53 ± 0.82 | 2.52 ± 1.73 |
| M2KO(ΔTM) prime-boost | 6.16 ± 1.17 | 1.37 ± 1.06 |
| FluMist ® prime-boost | 6.24 ± 1.31 | 3.30 ± 1.96 |

** Not Detected

TABLE 18C

Mucosal IgA Responses in Ferret
α-HA ELISA IgA titers 14 days post-challenge:

| | Nasal Wash | Sera |
|---|---|---|
| M2KO(ΔTM) prime only | 14 | Not Tested |
| FluMist ® prime only | 29 | Not Tested |

Figure 22A:
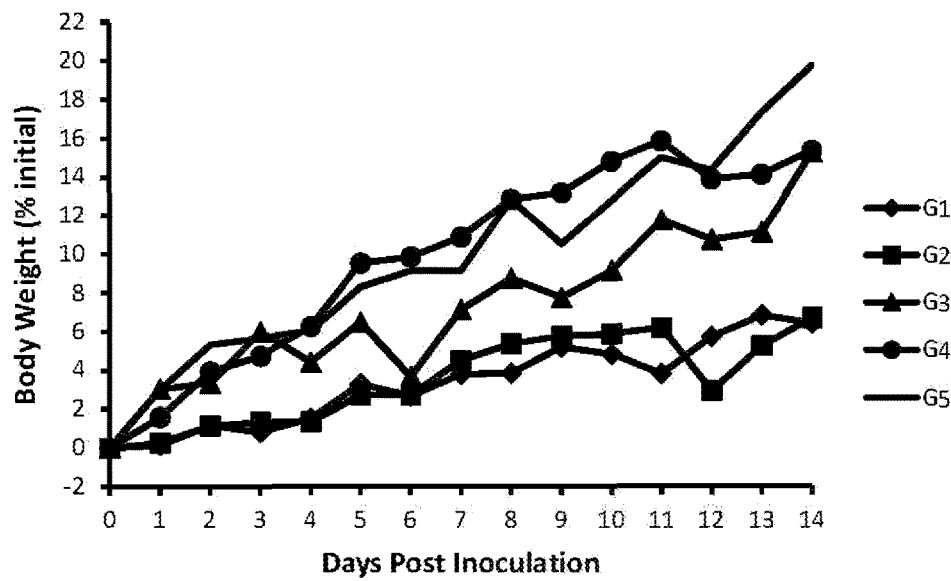
FIGS. 22A and 22B are charts showing changes in body weight of ferrets after vaccination. Ferrets were inoculated with $10^7$ $TCID_{50}$ of M2KO($\Delta$TM) virus [G1 and G3], with $10^7$ $TCID_{50}$ of FM #6 virus [G2 and G4] or OPTI-MEM™ [G5]. Changes in body weight were monitored for 14 days following prime vaccination (22A) and after receiving a booster vaccine (22B).
Figure 22B:
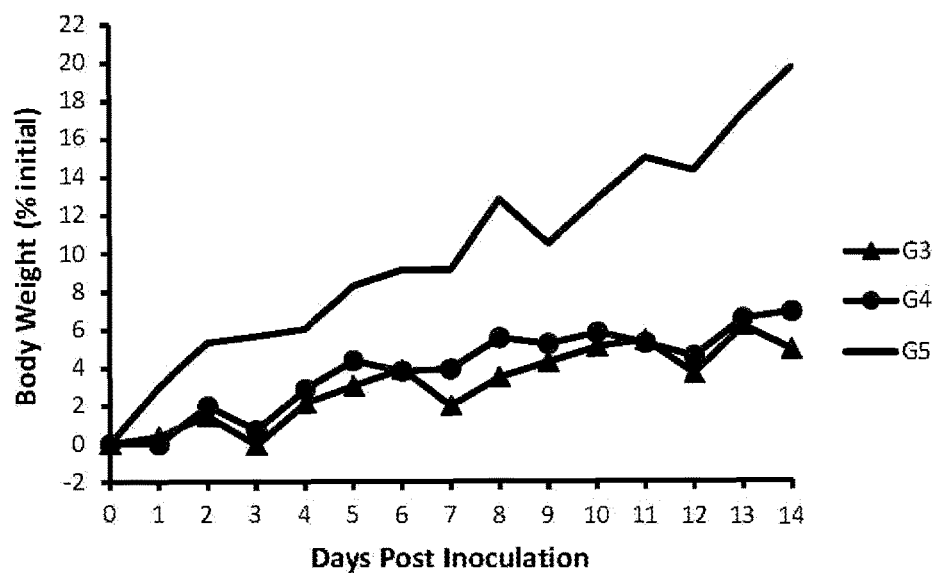
Figure 23:
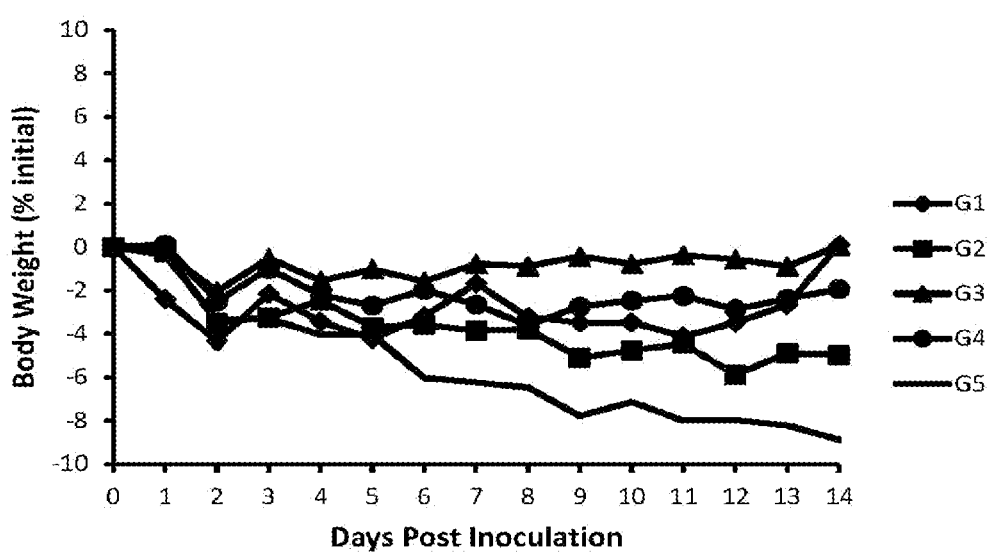
FIG. 23 is a chart showing changes in body weight of ferrets after challenge. Ferrets were challenged with $10^7$ $TCID_{50}$ of A/Brisbane/10/2007 (H3N2) influenza A virus. Body weight was monitored for 14 days post inoculation.
Figure 24A:
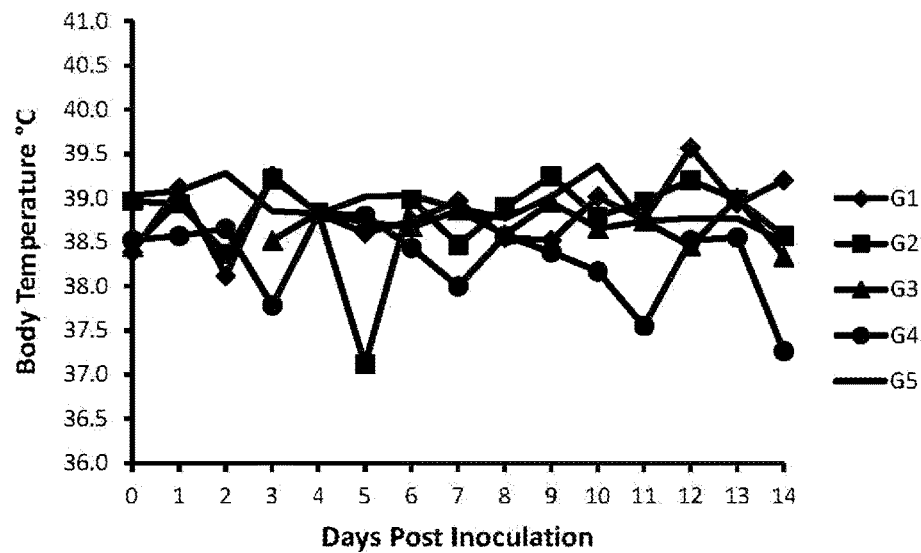
FIGS. 24A and 24B are charts showing changes in body temperature of ferrets after vaccination. Ferrets were inoculated with $10^7$ $TCID_{50}$ of M2KO($\Delta$TM) virus [G1 and G3], with $10^7$ $TCID_{50}$ of FM #6 virus [G2 and G4] or OPTI-MEM™ [G5]. Changes in body temperature were monitored for 14 days following prime vaccination (24A) and after receiving a booster vaccine (24B).
Figure 24B:
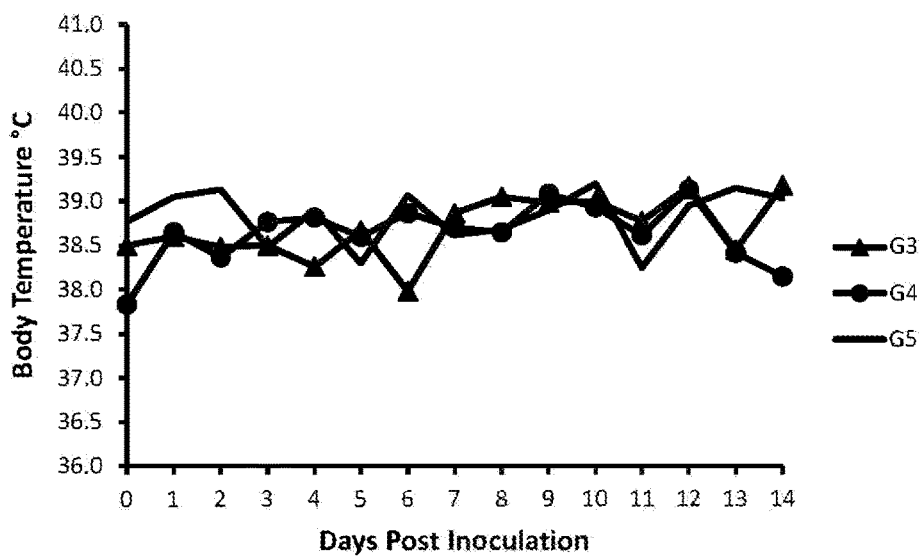
Figure 25:
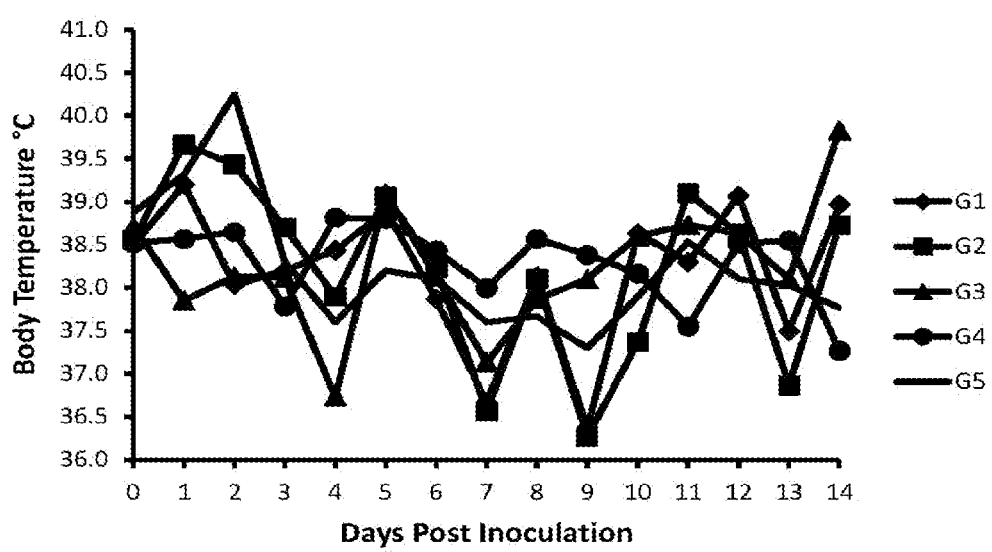
FIG. 25 is a chart showing changes in body temperature of ferrets after challenge. Ferrets were challenged with $10^7$ $TCID_{50}$ of A/Brisbane/10/2007 (H3N2) influenza A virus. Body temperature was monitored for 14 days post inoculation.

All ferrets survived vaccination with M2KO(ΔTM) virus and FM #6 virus. After prime vaccination, two ferrets inoculated with M2KO(ΔTM) virus presented respiratory signs (sneezing) on Day 8. After boost vaccination, ferrets inoculated with the FM #6 virus presented respiratory signs (sneezing) 7 days post vaccination. Sneezing was also observed in the OPTI-MEM™ ferrets on day 4 post boost. After prime vaccination, the relative inactivity index of ferrets inoculated with M2KO(ΔTM) virus and FM #6 virus was 0.07 and 0.27, respectively. This reduction in activity was only observed in one group per virus after prime vaccination. After boost vaccination no reduction in activity level was observed. Changes in body weight and temperature after virus inoculation are shown in FIGS. 22A and 22B. No weight loss was observed after vaccination; however, vaccination appeared to have an effect on weight gain. After vaccination, body weights of OPTI-MEM™ control ferrets increased 20% during the 14 day observation whereas body weight gain of the M2KO(ΔTM) or FM #6 vaccinated ferrets ranged from 6-15% after prime and 4-6% after boost. No increase in body temperature was observed in any groups after vaccination. Changes in body weight and temperature after challenge are shown in FIGS. 24A and 24B and FIG. 25 and clinical signs summarized in Table 19.

TABLE 19

Effect of virus challenge on survival and clinical signs of infection in ferrets.

| | | | | Clinical signs [a] | | |
|---|---|---|---|---|---|---|
| Group | Treatment | N | Total number dead | Respiratory signs (observed day of onset) | Loss of Appetite | Lethargy (RII)[b] |
| 1 | M2KO | 6 | 0/6 | 5/6 (2) | 0/6 | 0 |
| 2 | FM#6 | 6 | 0/6 | 5/6 (1) | 0/6 | 0 |
| 3 | M2KO | 6 | 0/6 | 3/6 (2) | 0/6 | 0 |
| 4 | FM#6 | 6 | 0/6 | 3/6 (2) | 0/6 | 0 |
| 5 | Vehicle (Control) | 6 | 0/6 | 3/6 (3) | 0/6 | 0 |

[a] Clinical signs were observed for 3 days after virus inoculation. Except for lethargy, findings for clinical signs are given as no. of ferrets with sign/total no. Respiratory signs included sneezing.
[b]Determined twice daily for 3 days of observation based on the scoring system and was calculated as the mean score per group of ferrets per observation (day) over the 3-day period. The relative inactivity index before inoculation was 0.

After challenge with A/Brisbne/10/2007 (H3N2), a 2-4% loss of body weight was observed on Day 2 post challenge in all animals. Throughout the 14 day observation period animal body weights remained below their initial weight. OPTI-MEM™ ferrets lost the most weight (8%). Weight loss among vaccinated ferrets was dependent on the vaccine regimen. Ferrets receiving the prime only regimen of M2KO (ΔTM) or FM #6 lost a maximum of 5% and 4% respectively. Ferrets receiving a booster lost a maximum of 3% for the FM #6 group and 2% for the M2KO(ΔTM) group. Elevated body temperatures post challenge were observed on Day 2 in OPTI-MEM™ ferrets and on Day 1 ferrets receiving the prime only regimens of M2KO(ΔTM) or FM #6 (FIG. 25). Body temperatures for ferrets receiving a booster remained within normal range.

To determine if the vaccination would prevent replication of challenge virus in the respiratory tract and reduce organ pathology tissues of challenged ferrets were histologically examined on day 3 post inoculation. Changes in the lungs of animals receiving the M2KO(ΔTM) prime only or prime/boost regimen were associated with increase in severity of mixed cell infiltrates in the lung when compared to the OPTI-MEM™ group. Minor differences in lung infiltrate incidences were observed between the M2KO(ΔTM) prime group and the M2KO(ΔTM) prime/boost group. An increase in the severity of mixed cell infiltrates in the lung was also seen in the FM #6 prime group and FM #6 prime/boost group when compared to the OPTI-MEM™ group. A slight increase in severity in lung mixed cell infiltrates was observed in the FM #6 prime/boost group over the FM #6 prime only group. In the nasal turbinates, animals receiving the prime or prime/boost of the M2KO(ΔTM) virus had lower severity of atrophy of respiratory epithelium when compared to the OPTI-MEM™ group. There were no differences in atrophy of the nasal turbinates when comparing prime versus prime/boost M2KO(ΔTM) groups. A slight increase in severity of atrophy of respiratory epithelium in animals receiving the FM #6 prime/boost regimen was observed versus animals FM #6 prime only regimen; the severity of atrophy of respiratory epithelium in all FM #6 animals was lower than that seen in the OPTI-MEM™ group. There was a decrease in incidence of neutrophilic infiltrates into the nasal cavity (lumen) in the M2KO(ΔTM) prime and prime/boost groups compared to the OPTI-MEM™ group. Neutrophilic luminal infiltrates in the M2KO(ΔTM) prime only group was interpreted as not different from the OPTI-MEM™ group. There was a slight increase in severity of luminal neutrophilic infiltrates in the FM #6 prime only and prime/boost groups when compared to the OPTI-MEM™ group. The concentrations of pre- and post-challenge virus dosing solutions were $10^7 0.83$ TCID$_{50}$/mL and $10^7 0.25$ TCID$_{50}$/mL, respectively, indicating good stability of the challenge material throughout administration.

Figure 45:
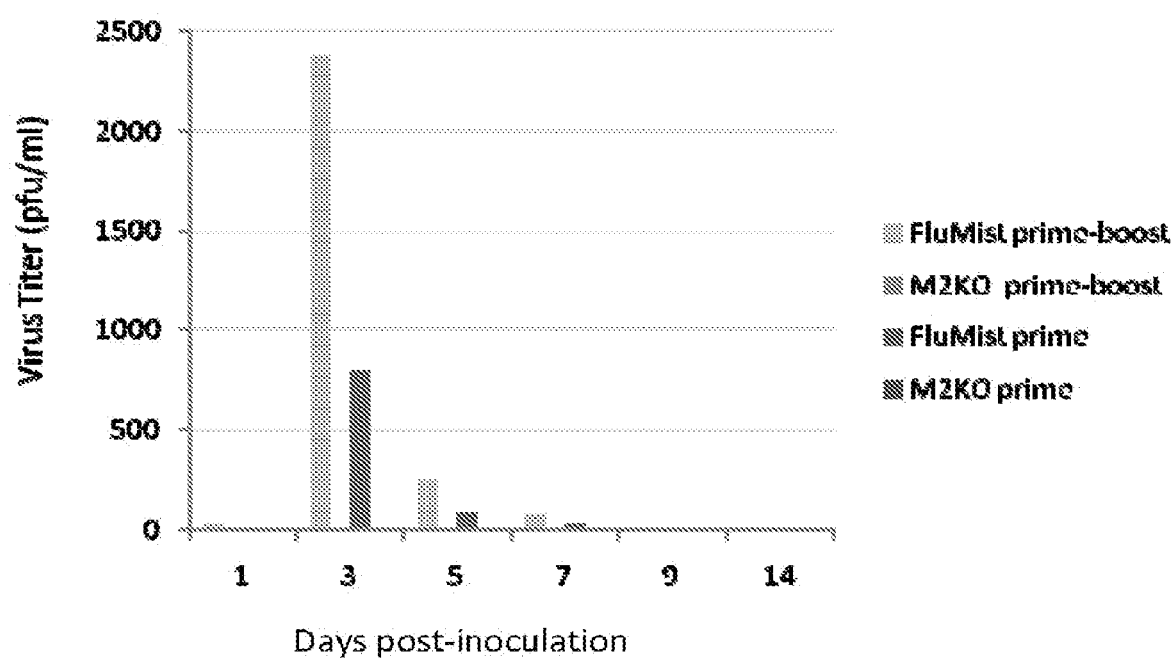
FIG. 45 is a chart showing M2KO(ΔTM) and FluMist® virus replication in the ferret respiratory tract.

FIG. 45 shows M2KO(ΔTM) and FluMist® virus replication in the ferret respiratory tract.

Figure 46:
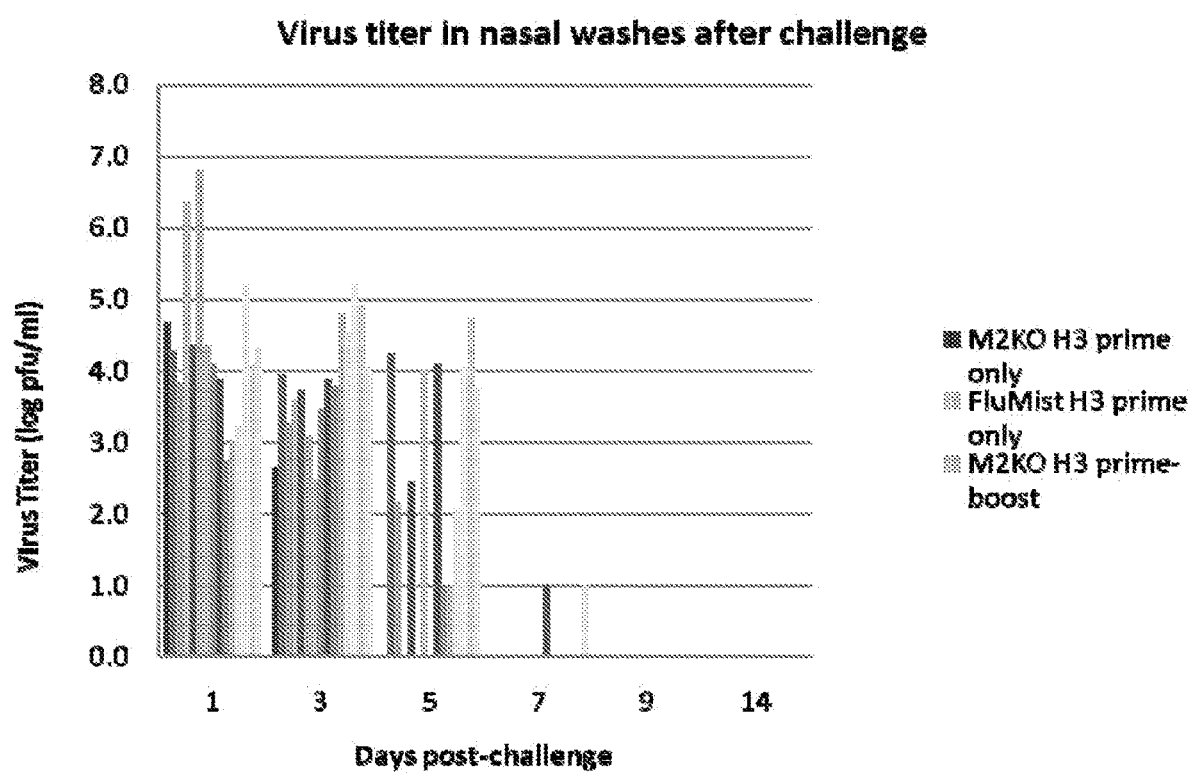
FIG. 46 is a chart showing M2KO(ΔTM) and FluMist® viral titers in nasal washes after intranasal challenge with A/Brisbane/10/2007 (H3N2) virus.

FIG. 46 shows M2KO(ΔTM) and FluMist® viral titers in nasal washes after intranasal challenge with A/Brisbane/10/2007 (H3N2) virus.

Figure 47:
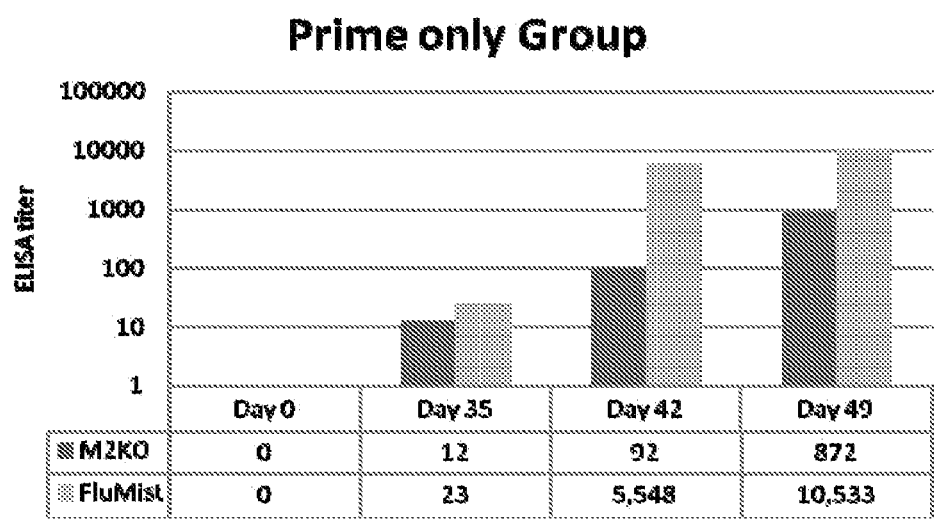
FIG. 47 is a chart showing IgG titers in ferrets following vaccination with M2KO(ΔTM) and FluMist® prime group only.

FIG. 47 shows IgG titers in ferrets following vaccination with M2KO(ΔTM) and FluMist,® prime group only.

Figure 48:
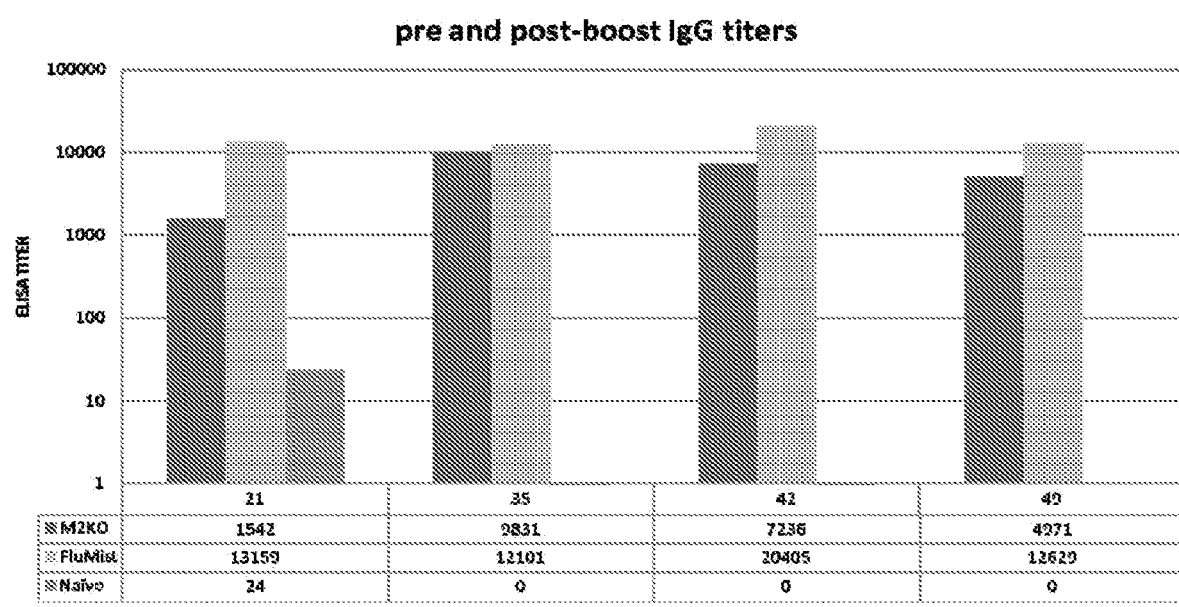
FIG. 48 is a chart showing IgG titers in ferrets following vaccination with M2KO(ΔTM) and FluMist,® prime-boost groups.

FIG. 48 shows IgG titers in ferrets following vaccination with M2KO(ΔTM) and FluMist,® prime-boost groups.

FIGS. 49A and 49B shows a summary of ELISA IgG titers in ferret sera from vaccination with M2KO(ΔTM) or FluMist® to post-challenge.

Conclusion

This example shows that intranasal administration of the M2KO(ΔTM) virus was not associated with any vaccine related adverse events (elevated body temperature, loss of weight or clinical signs). These results show that the M2KO (ΔTM) virus of the present technology is useful for use in an intranasal influenza vaccine.

Example 12: M2KO(ΔTM) Virus in not Transmitted in the Ferret Model

Summary—This example demonstrates that the M2KO (ΔTM) virus is not transmitted in the ferret model. The M2KO(ΔTM) virus was administered intransally to 3 female ferrets at a dose level of $1 \times 10^7$ TCID$_{50}$. As a control, a second group of 3 female ferrets was administered the A/Brisbane/10/2007 (H3N2) virus intranasally at a dose of $1 \times 10^7$ TCID$_{50}$. Twenty four hours after inoculation, each donor ferret was introduced into a transmission chamber with two naive ferrets (a direct contact and aerosol contact). Following inoculation, ferrets were observed for 14 days post inoculation for mortality, with body weights, body temperatures and clinical signs measured daily. Nasal washes were collected from all inoculated donor ferrets on days 1, 3, 5, 7, 9 and from all contact (direct and aerosol) ferrets on days 2, 4, 6, 8, 10 to look for viral shedding. Nasal washes and serum were collected from all ferrets at the inoculation of the study (Day 14) to evaluate antibody levels. No clinical signs of infection were observed in the M2KO(ΔTM) group; however, ferrets in the A/Brisbane/1 0/2007 (H3N2) group had weight loss, increased body temperatures and were sneezing. After inoculation with Brisbane/1 0, the donor ferrets exhibited an increase in body temperature 2 days after challenge and a reduction in weight. Activity levels were not reduced in any groups. Ferrets in direct contact with the donor ferrets showed progressive weight gain until day 4 post inoculation. A similar trend was observed in the aerosol contact ferrets beginning on day 6 post inoculation. The loss in body weight in the contact ferrets correlated with an increase in body temperature. Inoculation with the M2KO(ΔTM) virus does not elicit clinical signs of infection in inoculated animals. Spread to contact ferrets is unlikely.

Materials and Methods

A. Vaccine Material: The M2KO(ΔTM) virus is a recombinant virus which possesses internal 6 genes of PR8 (nucleoprotein (NP), polymerase genes (PA, PB1, PB2), non-structural (NS), matrix (M)), but which does not express functional M2 protein, as well as HA and NA genes of Influenza A/Brisbane/10/2007-like A/Uruguay/716/2007 (H3N2). M2KO(ΔTM) virus was administered intranasally to the animals in a 316 μL dose of 1×107 TCID$_{50}$ (50% Tissue Culture Infectious Doses).

B. Test Article Dose Formulation: The M2KO(ΔTM) virus dosing solution of $1 \times 10^7$ TCID$_{50}$/mL per 316 μL was prepared by diluting 45 of $1 \times 10^9$ TCID$_{50}$/mL into 1.377 mL PBS.

C. Animals and Animal Care: 22 female ferrets were purchased from Triple F Farms and 18 of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison Wis.) and city of Chicago tap water were provided ad libitum and were refreshed at least once daily. Fluorescent lighting in the animal rooms was maintained on a 12-hr light/dark cycle. Animal room temperature and relative humidity were within respective protocol limits and ranged from 23.0 to 25.0° C. and 36 to 50%, respectively, during the study.

D. Animal Quarantine and Randomization: The ferrets were held in quarantine for seven days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

E. Experimental Design: To assess the transmissibility of the M2KO(ΔTM) virus, ferrets were inoculated with M2KO (ΔTM) virus or A/Brisbane/10/2007 (H3N2) virus. The animals body weight, body temperature, clinical symptoms and viral shedding were monitored and immunological responses evaluated. 18 female ferrets (Triple F Farms, Sayre Pa.), 4 months of age at the time of study initiation were utilized for the study. All animal procedures were performed in an animal biosafety level-2 or level 3 facility. Prior to inoculation, ferrets were monitored for 3 days to measure body weight and establish baseline body temperatures. Temperature readings were recorded daily through a transponder (BioMedic data systems, Seaford, Del.) implanted subcutaneously in each ferret. Blood was collected prior to study initiation, and serum tested for influenza antibodies. Only ferrets with HI titers 40 to A/Brisbane/1 0/2007 (H3N2) virus were considered seronegative and used in this study. Study animals were randomized and divided into 2 groups (9 ferrets/group, 3/transmission chamber) as shown in Table 20. Ferrets in group 1 (Chambers A-C) were assigned to receive the M2KO(ΔTM) virus. Ferrets in group 2 (Chambers A-C) were assigned to receive the A/Brisbane/1 0/2007 (H3N2) virus. Within each group, ferrets were divided into inoculated donors or naive contacts.

exchange rate was 20 complete air changes per hour for each chamber, airflow was maintained as <0.1 m/sec. Chambers were maintained at a negative pressure of −0.15 inches of water. Ferrets were housed in wire cages with slat bottoms which were suspended over paper-lined waste pans. Ferrets were either dual housed in 32×24×14 cages or single housed in 24×24×14 wire cages which were placed inside each HEPA-filtered transmission chamber.

G. Virus Inoculation: Ferrets were inoculated with the M2KO(ΔTM) virus. A vial of frozen stock was thawed and diluted to the appropriate concentration in phosphate buffered saline solution. Ferrets were anesthetized with ketamine/xylazine and the virus dose administered intranasally in a volume of 316 μL for the M2KO(ΔTM). To confirm the inoculation titer of the M2KO(ΔTM) virus, aliquots of the

TABLE 20

Study Design

| Group | Chamber | Virus | N[1] | Inoculation (day)[2] | Donor Nasal Washes (days) | Contact Nasal Washes (days) | Serum collection |
|---|---|---|---|---|---|---|---|
| 1 | A | M2KO | 3 | 0 | 1, 3, 5, 7, 9, 14 | 2, 4, 6, 8, 10, 14 | 14 |
| 1 | B | M2KO | 3 | 0 | 1, 3, 5, 7, 9, 14 | 2, 4, 6, 8, 10, 14 | 14 |
| 1 | C | M2KO | 3 | 0 | 1, 3, 5, 7, 9, 14 | 2, 4, 6, 8, 10, 14 | 14 |
| 2 | A | Brisbane/10 | 3 | 0 | 1, 3, 5, 7, 9, 14 | 2, 4, 6, 8, 10, 14 | 14 |
| 2 | B | Brisbane/10 | 3 | 0 | 1, 3, 5, 7, 9, 14 | 2, 4, 6, 8, 10, 14 | 14 |
| 2 | C | Brisbane/10 | 3 | 0 | 1, 3, 5, 7, 9, 14 | 2, 4, 6, 8, 10, 14 | 14 |

[1]Each chamber consisted of three female ferrets: an infected donor ferret and 2 naïve contact ferrets (1 direct contact and 1 aerosol contact).
[2]Intranasally inoculated with a single dose of 316 μl of $1 \times 10^7$ TCID$_{50}$ of M2KO or $1 \times 10^7$ TCID$_{50}$ of A/Brisbane/10/2007 (H3N2) virus.

Each group was housed in separate rooms, and individuals working with the animals followed a strict work flow pattern to prevent cross contamination between the two groups In each group, one donor ferret was inoculated intranasally with a single dose of 316 μL of $1\times10^7$ TCID$_{50}$ of M2KO(ΔTM) (Group1) or $1\times10^7$ TCID$_{50}$ of A/Brisbane/10/2007 (H3N2) virus (Group 2). Twenty-four hours post inoculation; each donor was placed in the same cage with 1 naive ferret (direct contact), dual housed within a wire cage. An additional ferret (aerosol contact) was placed in a separate adjacent wire cage (single housed) within the transmission chamber separated from the donor's cage by a distance of 10-12 cm. Ferret body temperatures, weights, and clinical symptoms were monitored daily for 14 days post-inoculation. Nasal washes were collected from all inoculated donor ferrets on days 1, 3, 5, 7, 9 and from all contact (direct and aerosol) ferrets on days 2, 4, 6, 8, 10 for virus titration in cells. Nasal washes were collected from all ferrets on day 14 for antibody titration. Nasal wash samples were kept at −65° C.

F. Transmission Chambers: Each transmission chamber was 2 cubic meters. A computerized air handling unit was used for HEPA filtration and to monitor and control environmental conditions within the transmission chambers. To provide directional airflow, HEPA-filtered air was supplied through an inlet port located at one end of the chamber, exited through an outlet port at the opposite end the chamber, HEPA filtered and exhausted into the room. Air dosing solutions were collected prior to dosing (pre-dose) and after dosing (post-dose). The aliquots were stored at 65° C. for virus titration.

H. Challenge Virus: Influenza A virus, strain A/Brisbane/10/2007, serotype H3N2 was used to inoculate the control ferrets. The virus was stored at approximately −65° C. prior to use. The dose level of challenge virus used was prepared at $1\times1\,07$ TCID$_{50}$ in a volume of 316 μL. A quantitative viral infectivity assay, TCID$_{50}$ assay was performed at IITRI on a portion of the prepared viral challenge solution. The viral titer assay was performed according to IITRI Standard Operating Procedures.

I. Moribundity/Mortality Observations: Following challenge, all animals were observed twice daily for mortality or evidence of moribundity. Animals were observed for 14 days after vaccine inoculation and for 14 days after challenge.

J. Body Weights and Body Weight Change: Body weights were recorded within two days of receipt and at randomization. All study animals were weighed prior to inoculation, daily for 14 days following each vaccination and assessed daily for 14 days post challenge. Prior to inoculation, ferrets were monitored for 3-5 days to measure establish baseline body temperatures. Temperature readings were recorded daily for 14 days following each vaccination and recorded daily for 14 days post challenge through a transponder (BioMedic data systems, Seaford, Del.) implanted subcutaneously in each ferret. The change in temperature (in degrees Celsius) was calculated at each time point for each animal.

K. Clinical Observations: The change in temperature (in degrees Celsius) was determined daily for each ferret. Clinical signs of, inappetence, respiratory signs such as dyspnea, sneezing, coughing, and rhinorrhea and level of activity was assessed daily. A scoring system based on that described by Reuman, et al., "Assessment of signs of influenza illness in the ferret model," *J. Virol*, Methods 24:27-34 (1989), was used to assess the activity level as follows: 0, alert and playful; 1, alert but playful only when stimulated; 2, alert but not playful when stimulated; and 3, neither alert nor playful when stimulated. A relative inactivity index (RII) was calculated as the mean score per group of ferrets per observation (day) over the duration of the study.

L. Survival Checks: Two survival checks were performed daily on all study animals throughout the study. Both survival checks occurred simultaneously with the clinical observations. The second check was performed later within the same day.

M. Nasal Washes: Ferrets were anesthetized with a ketamine (25 mg/kg) and xylazine (2 mg/kg) mixture, and 0.5 ml of sterile PBS containing penicillin (100 U/ml), streptomycin (100 and gentamicin (50 was injected into each nostril and collected in a specimen cup when expelled by the ferret.

N. Euthanasia: Study animals were euthanized by an intravenous dose of sodium pentobarbital 150 mg/kg. Death was confirmed by absence of observable heartbeat and respiration. Necropsies were performed on all study animals.

O. Serum Collection: Pre-vaccination serum (days −3 to −5) and post inoculation serum (day 14) was collected from all ferrets. Ferrets were anesthetized with a ketamine (25 mg/kg) and xylazine (2 mg/kg) mixture. A sample of blood (approximately 0.5-1.0 mL) was collected via the vena cava from each ferret and processed for serum. Blood was collected into Serum Gel Z/1.1 tubes (Sarstedt Inc. Newton, N.C.) and stored at room temperature for not more than 1 hour before collecting serum. Serum Gel Z/1.1 tubes were centrifuged at 10,000×g for 3 minutes and the serum collected. Individual pre-inoculation serum samples were collected and two aliquots made from each sample. One aliquot was tested prior to the initiation of the study to confirm ferrets are free of antibodies to influenza A viruses and one aliquot of the serum stored at −65° C.

P. Hemagglutination Inhibition (HI) Assay: Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2) influenza A virus. After incubation, 0.5% avian red blood cells were added to each sample and incubated for 30±5 minutes. Presence or absence of hemagglutination was then scored.

Q. Virus Titers: The concentration of infectious virus in the pre- and post-challenge virus inoculum samples was determined by $TCID_{50}$ assay in Madin-Darby Canine Kidney (MDCK) cells. Briefly, samples kept at −65° C. were thawed and centrifuged to remove cellular debris. The resulting supernatant were diluted 10-fold in triplicate in 96-well microtiter plates in Dulbecco's Modified Eagle Medium (DMEM) (Gibco, Carlsbad, Calif., USA) containing Pencillin/Streptomycin, 0.1% Gentamicin, 3% $NaCO_3$, 0.3% BSA fraction V (Sigma St. Louis, Mo.), 1% MEM vitamin solution (Sigma) and 1% L-glutamine (Mediatech, Manassas, Va., USA). After 10-fold serial dilutions were made, 1 OOflL was transferred into respective wells of a 96-well plate which contained a monolayer of MDCK cells. Plates were incubated at 37° C.±2° C. in 5±2% $CO_2$ 70% humidity. After 48 hours, the wells were observed for cytopathogenic effect (CPE). Supernatant from each well (50 µl) was transferred to a 96 well plate and the hemagglutination (HA) activity determined and recorded. The HA activity of the supernatant was assessed by HA assay with 0.5% packed turkey red blood cells (tRBCs). $TCID_{50}$ titers were calculated using the method of Reed LJ and Muench H, "A simple method for estimating 50% endpoints," *Am. J. Hygiene* 27: 493-497 (1938).

R. Data Analysis: Body weights and body weight gains (losses) and changes in body temperature were determined for each individual animal expressed as mean and standard deviations of the mean for each test group.

Results

After inoculation of donor ferrets with either the M2KO (ΔTM) virus or the A/Brisbane/1 0/2007 (H3N2) influenza A virus donor ferrets were introduced into transmission chambers containing naive contact ferrets. Ferrets were monitored daily for clinical signs of infection, nasal washes were collected to monitor viral shedding and serum collected to measure serum antibody titers. All ferrets survived inoculation with M2KO(ΔTM) virus and A/Brisbane/10/2007 (Table 21). No clinical signs of disease were observed in ferrets in the M2KO(ΔTM) group. Two of the three donor ferrets inoculated with A/Brisbane/10/2007 virus presented respiratory signs (sneezing) on Day 6 and 8. Direct contact ferrets in all chambers presented with sneezing on Day 8. No sneezing was observed in the aerosol contact ferrets. A reduction in activity level was not observed.

TABLE 21

Clinical signs in inoculated donor ferrets and contact ferrets.

| | | | | | Clinical signs[b] | | |
|---|---|---|---|---|---|---|---|
| Group | Treatment | N | Serum HI Titer[a] | Total number dead | Respiratory signs (observed day of onset) | Loss of Appetite | Lethargy (RII)[c] |
| | | | | M2KO | | | |
| Donors | M2KO | 3 | <10 | 0/3 | 0/3 | 0/3 | 0 |
| Direct Contracts | M2KO | 3 | <10 | 0/3 | 0/3 | 0/3 | 0 |

TABLE 21-continued

Clinical signs in inoculated donor ferrets and contact ferrets.

| Group | Treatment | N | Serum HI Titer[a] | Total number dead | Respiratory signs (observed day of onset) | Loss of Appetite | Lethargy (RII)[c] |
|---|---|---|---|---|---|---|---|
| Aerosol Contracts | M2KO | 3 | <10 | 0/3 | 0/3 | 0/3 | 0 |
| Brisbane | | | | | | | |
| Donors | Brisbane/10 | 3 | <10 | 0/3 | 2/3 (6, 8) | 0/3 | 0 |
| Direct Contracts | Brisbane/10 | 3 | <10 | 0/3 | 3/3 (8, 8, 8) | 0/3 | 0 |
| Aerosol Contracts | Brisbane/10 | 3 | <10 | 0/3 | 0/3 | 0/3 | 0 |

[a]Hemagglutination inhibition (HI) antibody titers to homologous virus in ferret serum prior to virus inoculation.
[b]Clinical signs were observed for 14 days after virus inoculation. Except for lethargy, findings for clinical signs are given as no. of ferrets with sign/total no. Respiratory signs were sneezing, day of onset for each ferret in parentheses.
[c]Determined twice daily for 14 days of observation based on the scoring system and was calculated as the mean score per group of ferrets per observation (day) over the 14-day period. The relative inactivity index before inoculation was 0.

Figure 26A:
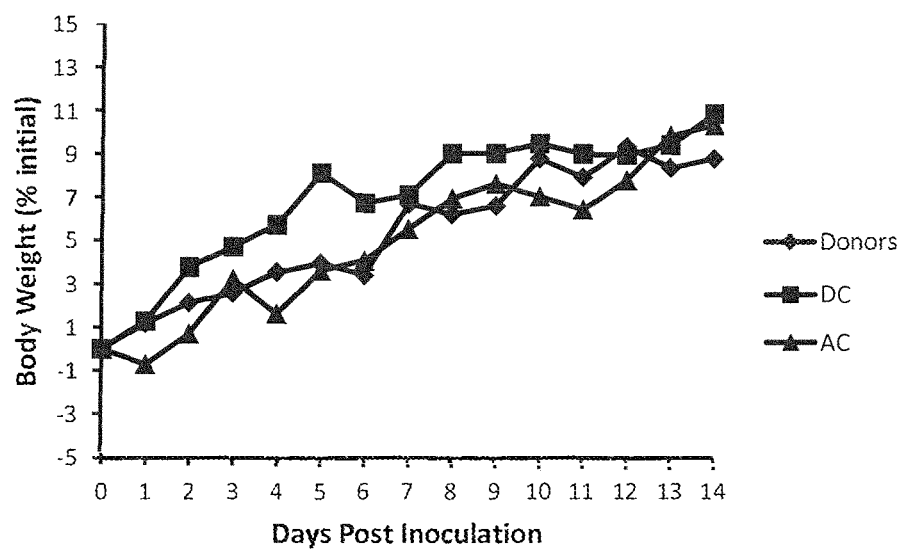
FIGS. 26A and 26B are charts showing changes in weight of ferrets after virus inoculation. Donor ferrets were inoculated on day 0 with either 10 7 $TCID_{50}$ of M2KO($\Delta$TM) virus (26A) or with $10^7$ $TCID_{50}$ of A/Brisbane/10/2007 (H3N2) virus (26B). 24 hours (Day 1) after inoculation donors were placed in a cage with direct contacts (DC) adjacent to a cage housing an aerosol contact (AC). Changes in body weight were monitored for 14 days following donor inoculation.
Figure 26B:
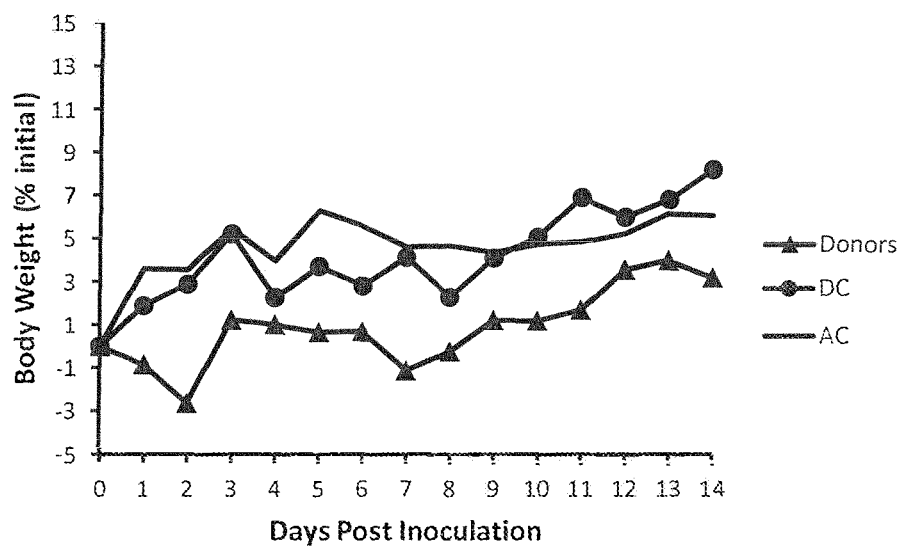
Figure 27A:
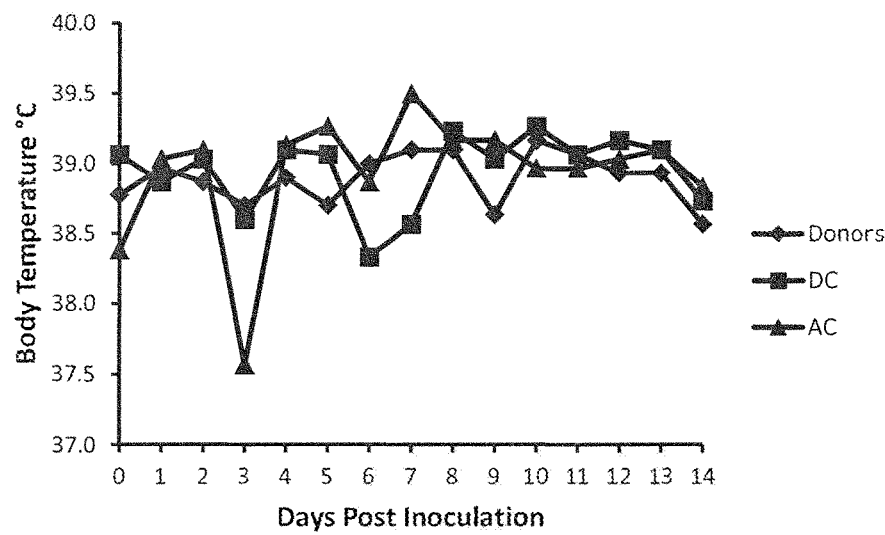
FIGS. 27A and 27B are charts showing changes in body temperature of ferrets after virus inoculation. Donor ferrets were inoculated on day 0 with either $10^7$ $TCID_{50}$ of M2KO ($\Delta$TM) virus (27A) or with $10^7$ $TCID_{50}$ of A/Brisbane/10/ 2007 (H3N2) virus (27B). 24 hours (Day 1) after inoculation donors were placed in a cage with direct contacts (DC) adjacent to a cage housing an aerosol contact (AC). Changes in body temperature were monitored for 14 days following donor inoculation.
Figure 27B:
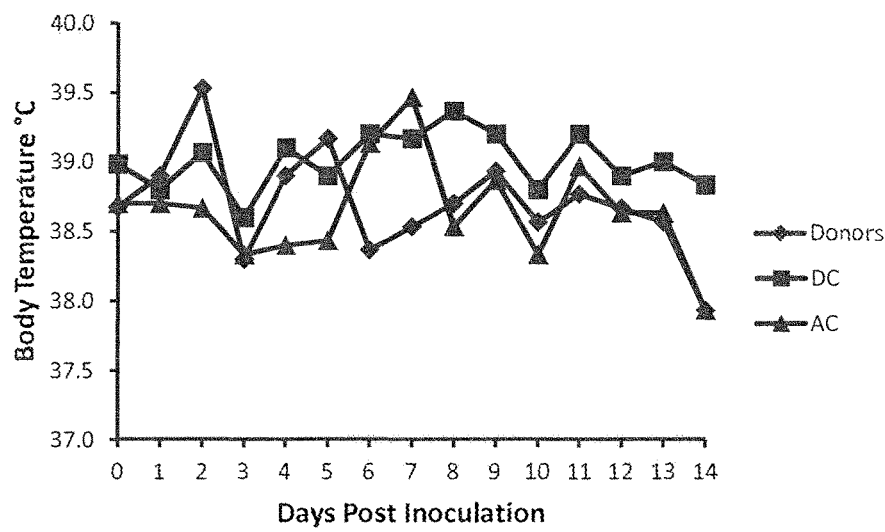

Changes in body weight and temperature after virus inoculation are shown in FIGS. 26A and 26B and FIGS. 27A and 27B. No significant weight loss was observed after inoculation with the M2KO(ΔTM) virus. The aerosol contacts averaged a 1% loss in weight on day; however, it is unlikely this due to exposure to virus. Body weights of ferrets in the M2KO(ΔTM) virus increased was 9% for donor ferrets and 10-11% for contact ferrets during the 14 day observation (FIG. 26A). Body weight gain of the A/Brisbane/10/2007 was only 3% for donor ferrets and 6-8% for contact ferrets indicating a viral infection (FIG. 26B). In the M2KO(ΔTM) group, body temperatures remained with in normal levels with the exception of Day 3 post infection (FIG. 27A). Body temperatures were lower than normal for the aerosol contact ferrets. This was attributed to faulty or failing temperature transponders, temperatures were recorded within normal range throughout the rest of the study. Elevated body temperatures were observed on Day 2 in A/Brisbane/10/2007 donor ferrets and on Day 7 for aerosol contacts (FIG. 27B). The concentrations of pre and post-challenge virus dosing solution were $10^{7.50}$ TCID$_{50}$/mL and $10^{7.25}$ TCID$_{50}$/mL, respectively, indicating good stability of the challenge material throughout administration.

FIG. 50 shows viral titers in nasal washes from ferrets in a virus transmission study. The data shows that M2KO(ΔTM) virus does not transmit (no virus detected), whereas the control Brisb/10 virus is transmitted.

Conclusion

This example shows that ferrets inoculated with the A/Brisbane/10/2007 virus exhibited clinical signs of infection (sneezing, loss in body weight and a transient elevated body temperature), whereas ferrets inoculated with the M2KO(ΔTM) virus showed no clinical signs of disease. Therefore, inoculation of donor ferrets with the M2KO(ΔTM) did not appear to cause an infection or transmit virus via contact or via aerosol. These findings show that the M2KO(ΔTM) virus of the present technology is useful for intranasal influenza vaccines.

Example 13. M2KO(ΔTM) Virus Elicits Both Humoral and Mucosal Immune Responses in Mice This examples demonstrates that the M2KO(ΔTM) virus elicits both humoral and mucosal immune responses in mice. The immunogenicity of M2KO(ΔTM) was evaluated in mice and compared to the immune responses generated by other modes of vaccination. An immunogenicity study was performed containing the following groups as outline in Table 22: 1. M2KO(ΔTM) virus, 2. PR8 virus (10 pfu), live vaccine representative, 3. Inactivated PR8 virus (Charles River Laboratories, Wilmington, Mass.), 1 µg, intranasal (IN) 4. Inactivated PR8 virus, 1 µg, intramuscular (IM), or PBS only.

TABLE 22

Vaccine Groups in Immunogenicity Study

| Immunogen | Route of Delivery | Dose | Rationale |
|---|---|---|---|
| M2KO(ΔTM) virus | Intranasal | 1 × 10$^4$ pfu | Comprises M2KO(ΔTM) (SEQ ID NO: 1) Mutation |
| PR8 virus | Intranasal | 10 pfu | Represents the immune responses associated with a natural infection and/or live flu vaccine |
| Inactivated PR8, whole virus | Intranasal | 1 µg | Demonstrates baseline response generated by killed flu virus delivered intranasally |
| Inactivated PR8, whole virus | Intramuscular | 1 µg | Standard delivery route for traditional inactivated flu vaccine |

To test the immunogenicity of M2KO(ΔTM) virus, mice were intranasally inoculated with 1.2×10$^4$ pfu of M2KO(ΔTM), 10 pfu of wild-type PR8, 1 µg of inactivated whole PR8 (Charles River Laboratories, Wilmington, Mass.), or PBS as control, along with a group intramuscularly administered 1 µg of inactivated whole PR8. Three weeks after the immunization, serum and trachea-lung washes were collected from mice and anti-PR8 immunoglobulin G (IgG) and IgA levels were measured by enzyme linked immunosorbent assay (ELISA). Briefly, ELISA plates were coated by whole inactivated PR8, blocked by bovine serum albumin (BSA), and samples were applied. Mouse IgG and IgA antibodies were detected by horseradish peroxidase labeled anti-mouse IgG- and IgA-goat antibodies (KPL, Inc., Gaithersburg, Md.) and SureBlue TMB (KPL, Inc.) substrate.

Figure 28A:
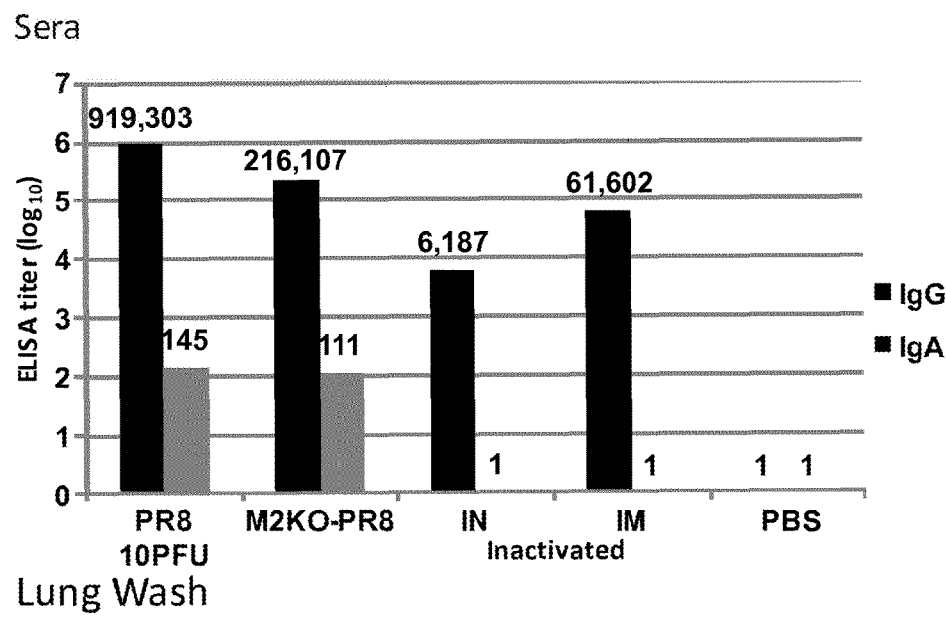
FIGS. 28A and 28B are charts showing that M2KO($\Delta$TM) vaccine elicits humoral and mucosal responses.
Figure 28B:
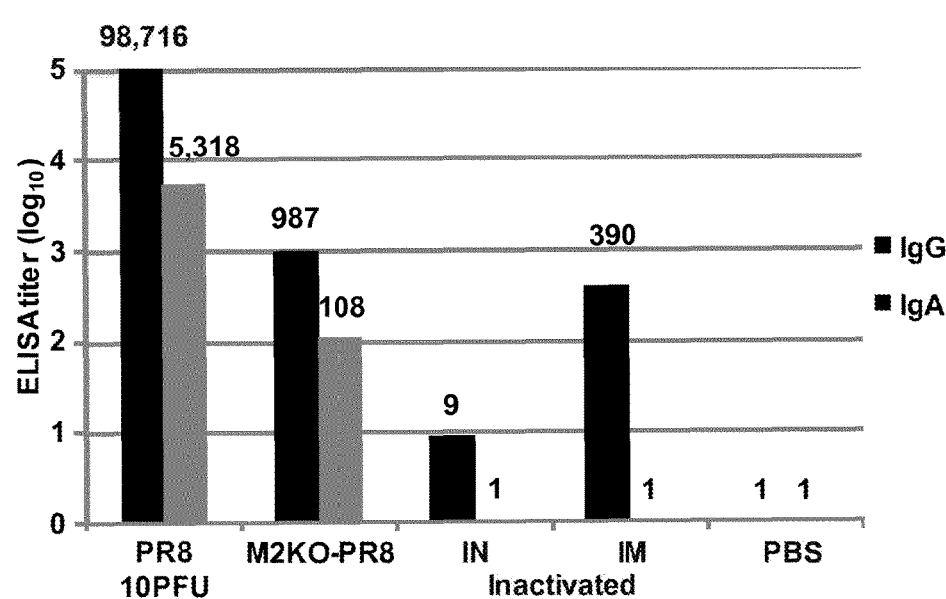

As expected, mice in the immunized groups showed significant elevation of anti-PR8 antibodies in serum and trachea-lung wash compare to the PBS only group (FIGS. 28A and 28B). Anti-PR8 IgG levels in sera for M2KO(ΔTM) virus are higher than the inactivated PR8 groups and similar to live PR8 virus. More importantly anti-PR8 IgA antibodies were present only in the PR8 and M2KO(ΔTM) immunized mice in both sera and trachea-lung washes. These data suggest that M2KO(ΔTM) virus elicits significant humoral and mucosal immune response in mice.

Figure 29A:
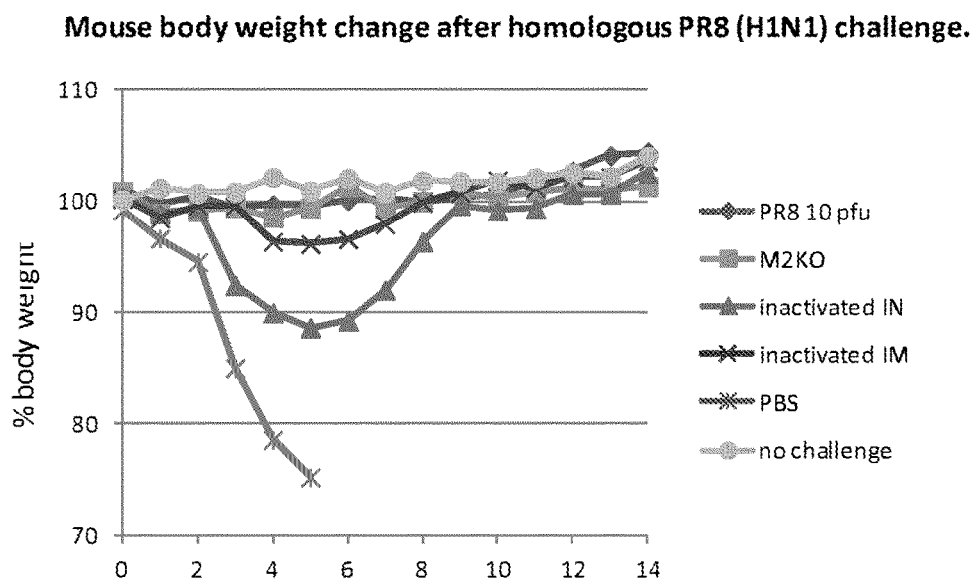
FIGS. 29A and 29B are charts showing that M2KO($\Delta$TM) vaccine protects mice from lethal homosubtypic and heterosubtypic viral challenge.
Figure 30A:
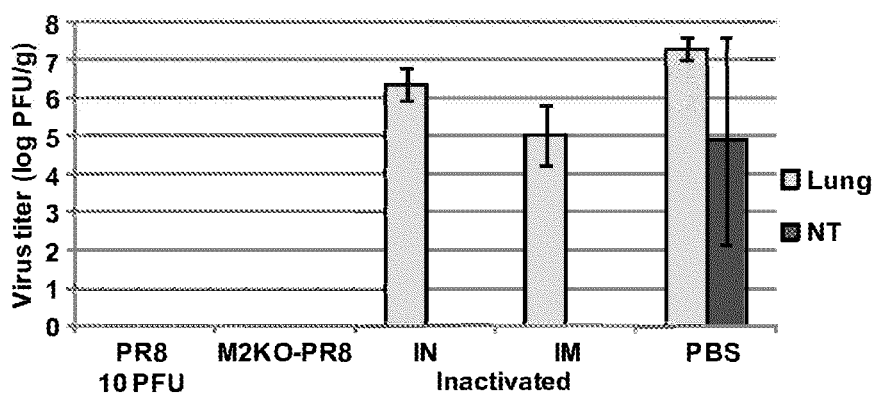
FIGS. 30A and 30B are charts showing that M2KO($\Delta$TM) vaccine controls challenge virus replication in respiratory tract.

Example 14 M2KO(ΔTM) Virus Protects Mice from Lethal Homosubtypic and Heterosubtypic Challenge This example demonstrates that the M2KO(ΔTM) virus protects mice from lethal homosubtypic and heterosubtypic challenge. The protective efficacy M2KO(ΔTM) virus was evaluated by challenging the immunized mice with lethal doses of the wild-type PR8 (H1N1; homosubtypic challenge) or mouse-adapted influenza A/Aichi/2/68 (Aichi; H3N2; heterosubtypic challenge) six weeks post-immunization. None of the mice immunized with either M2KO(ΔTM) or 10 pfu of PR8 and subsequently challenged by wild-type PR8 showed any clinical symptoms including weight loss (FIG. 29A). In contrast, naive PBS mice died or were euthanized due to greater than 20% weight loss by day 5. Virus replication in the respiratory tracts of challenged mice was determined on day 3 post-challenge by TCID$_{50}$ assay in MDCK cells. As shown in FIG. 30A, no virus was detected (limit of detection $10^{2.75}$TCID$_{50}$/organ) in the lungs of M2KO(ΔTM) or PR8 immunized mice indicating that M2KO(ΔTM) provided sterile immunity similar to PR8 infection. In contrast, challenge virus was recovered from the inactivated PR8 and PBS groups.

Figure 29B:
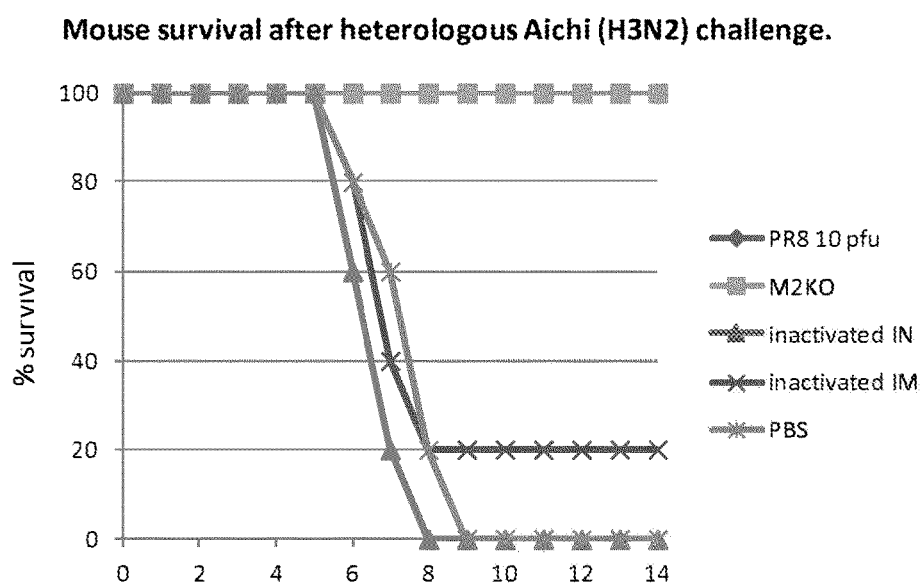
Figure 30B:
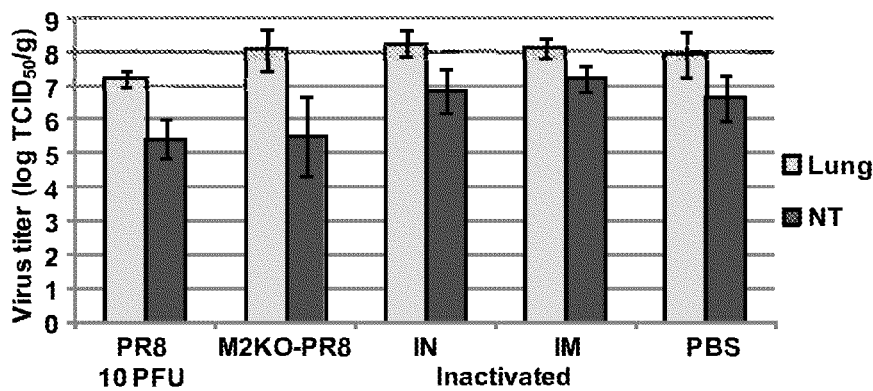

For heterosubtypic challenge, mice were challenged by Aichi (H3N2). M2KO(ΔTM) and wild-type PR8 immunized mice survived challenge whereas mice that received inactivated PR8 or PBS succumbed to infection (FIG. 29). Virus titers in mouse respiratory tracts on day 3 post-challenge did not show significant reduction in M2KO(ΔTM)-vaccinated mice compared to mice in other groups (FIGS. 30A and 30B). These results suggest that the cross-protection observed against Aichi challenge may in part be due to T-cell mediated immune responses induced by the M2KO(ΔTM) vaccine. Hemagglutination inhibition (HI) antibodies to Aichi were not detectable (less than 1:40) in post-challenge sera from challenged mice suggesting that protection was not mediated by neutralizing antibodies.

The M2KO(ΔTM) virus stimulates both humoral and cellular immune responses and confers protective immunity to animals against lethal homo- and hetero-subtypic challenge as summarized in Table 23.

TABLE 23

Protection After Homosubtypic (H1N1) and Heterosubtypic (H3N2) Influenza Challenge Survival (%)

| Vaccine Group | PR8 (H1N1) Challenge | Aichi (H3N2) Chalenge |
|---|---|---|
| M2KO(ΔTM) | 100% | 100% |
| PR8 | 100% | 100% |
| Inactivated PR8, IN | 100% | 0% |
| Inactivated PR8, IM | 100% | 20% |
| PBS | 0% | 0% |

Example 15 M2KO(ΔTM) Vaccine Compared to Fluzone® and FluMist®

This example demonstrates the efficacy of the M2KO (ΔTM) virus compared to ive attenuated virus (FluMist®), Fluzone® inactivated flu vaccine. Mice were immunized with M2KO(ΔTM) virus, cold adapted live attenuated virus (FluMist®), Fluzone® inactivated flu vaccine or mock immunized by PBS. M2KO(ΔTM)-H3 virus was constructed by inserting the HA and NA coding sequences of Influenza A/Brisbane/10/2007-like, A/Uruguay/716/2007 (H3N2) in to the M2KO(ΔTM) backbone (SEQ ID NO:1). FluMist®-H3, internal genes from the cold-adapted A/AA/6/60 backbone, containing the HA and NA genes of Influenza A/Brisbane/10/2007-like, A/Uruguay/716/2007(H3N2) was plaque purified from the 2009/2010 trivalent vaccine formulation. Fluzone® 2009/2010 formulation was used directly as the trivalent formulation.

Figure 31:
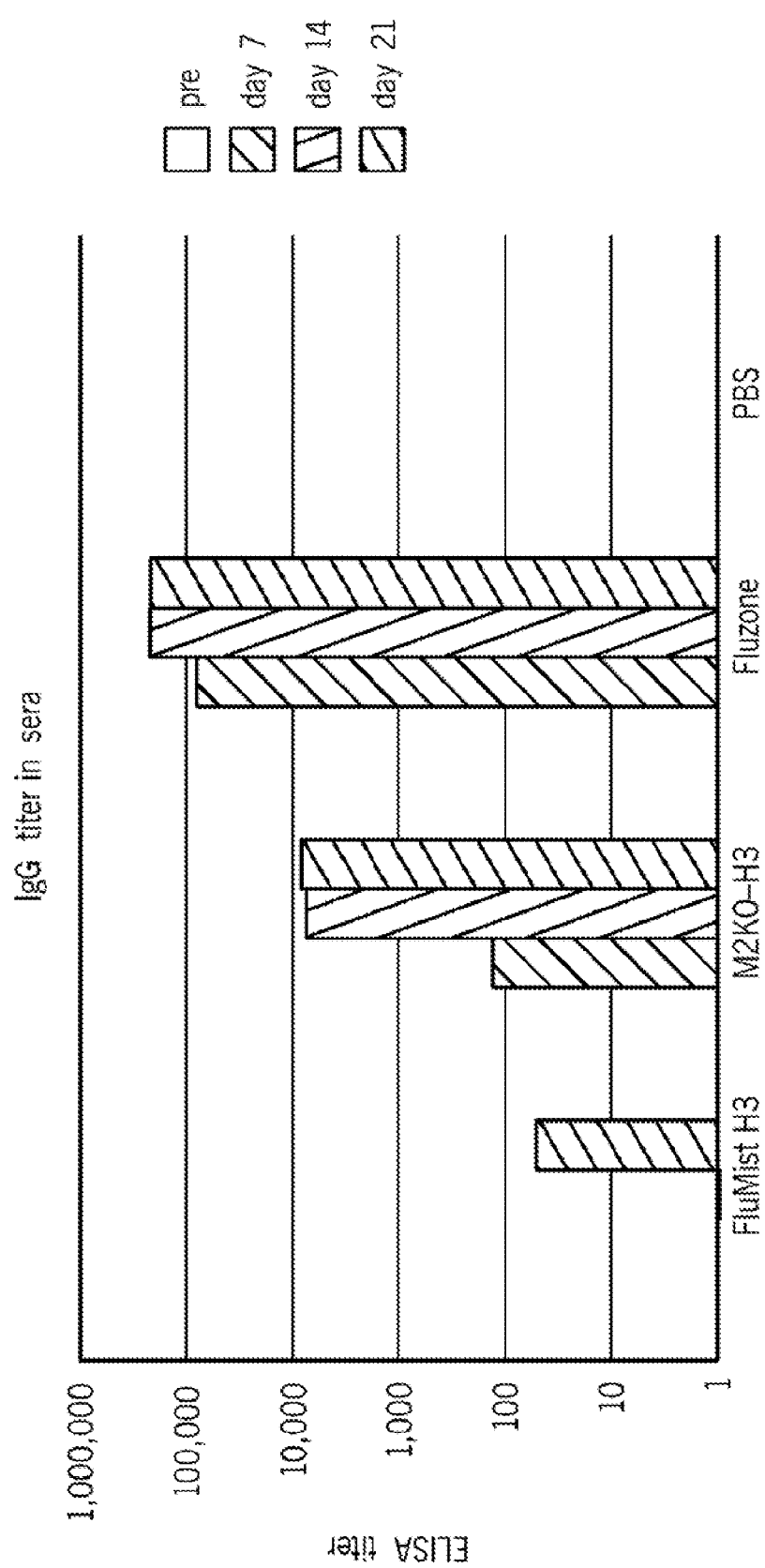
FIG. 31 is a chart showing the kinetics of antibody response to M2KO($\Delta$TM) vaccine in sera.

Sera was obtained on days 7, 14, 21 post-immunization to compare the kinetics of antibody response by ELISA (FIG. 31). M2KO(ΔTM)-H3 virus, a replication deficient virus, developed antibodies earlier than FluMist®-H3, a live flu virus vaccine that undergoes multi-cycle replication in an attenuated manner. The inactivated vaccine Fluzone® had the highest antibody titers in sera as it is a concentrated presentation of antigen.

Figure 32:
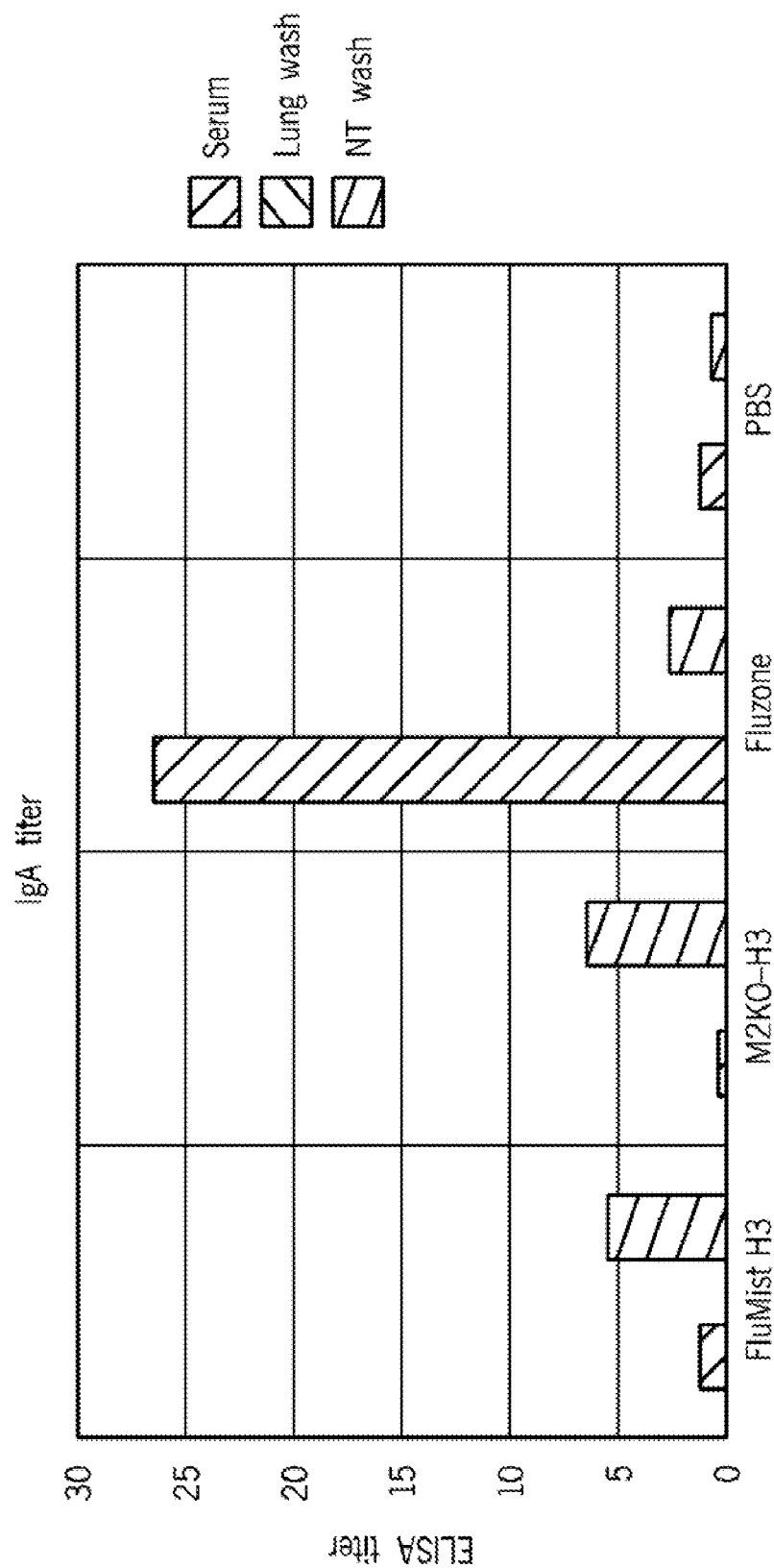
FIG. 32 is a chart showing the mucosal antibody response to M2KO($\Delta$TM) vaccine in sera and respiratory tract.

The presence of anti-HA mucosal antibody in sera, lung wash, and nasal turbinates was evaluated by ELISA. M2KO (ΔTM)-H3 and FluMist,® the two live flu vaccines, had higher IgA in the respiratory tract than the inactivated vaccine Fluzone®. (FIG. 32)

Figure 33:
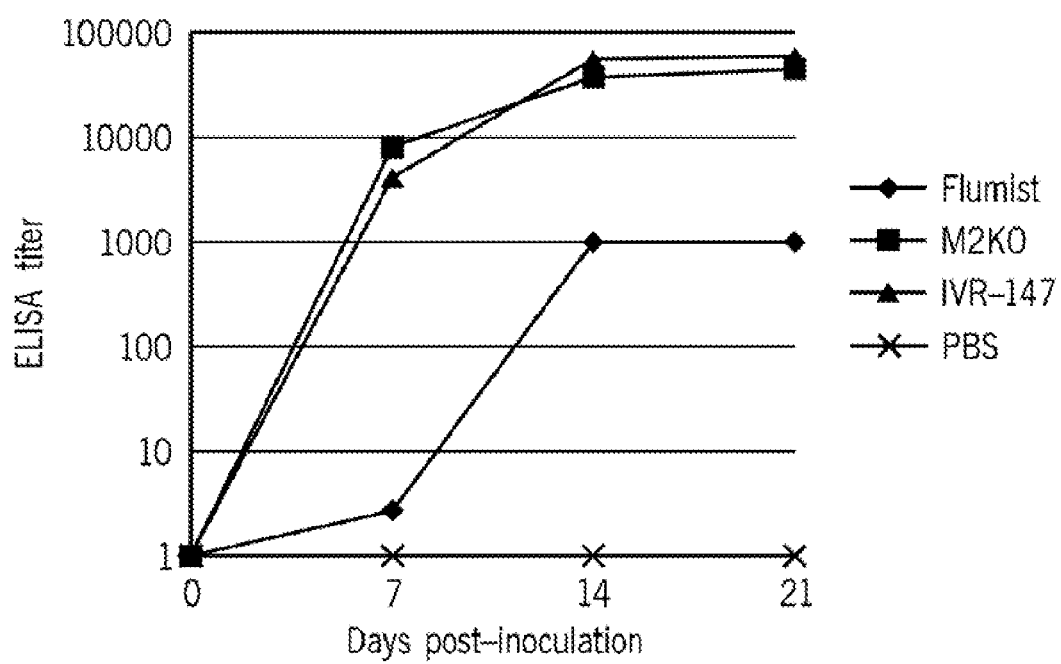
FIG. 33 is a chart showing the kinetics of anti-HA IgG in mice in response to M2KO($\Delta$TM) vaccine.

Example 16: Comparison of Protection and Immunogenicity Elicited by Live Viruses Six-week-old female BALB/c mice, anesthetized with isoflurane, were infected intranasally on days 0 and 28 with $10^6$ TCID$_{50}$/50 μl of M2KO(ΔTM)-H3 (described above), FluMist® (2009-2010) (H3N2) IVR-147 (PR8xBrisbane/10/2007). IVR-147 is the wild-type version of the M2KO (ΔTM) virus; i.e. contains a functional M2 protein. Mock-infected control mice received 50 μl PBS instead of virus. Serum was collected weekly from all the mice and analyzed for the presence of anti-HA antibodies by ELISA. As shown in FIG. 33, M2KO(ΔTM) virus and IVR-147 generated higher antibody levels with rapid kinetics compared to FluMist®.

Figure 34A:
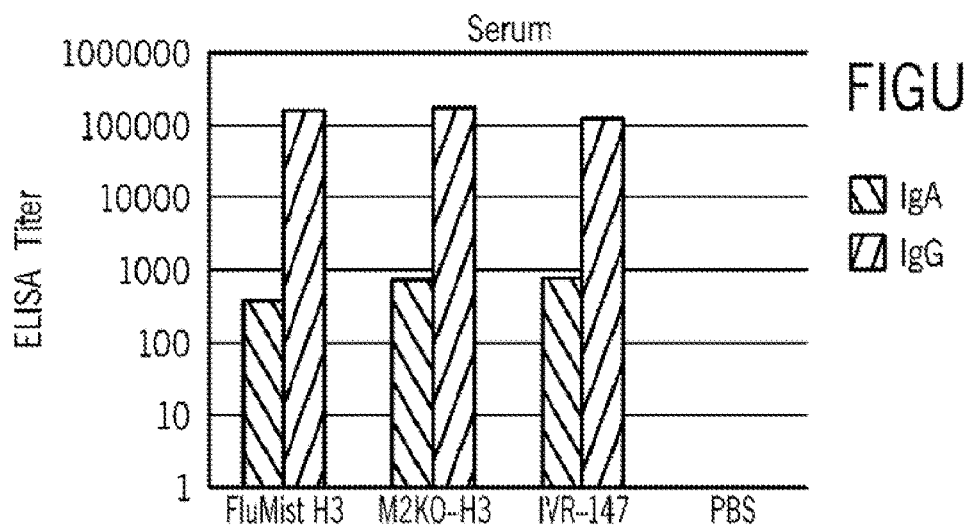
FIGS. 34A, 34B, and 34C are charts showing that M2KO ($\Delta$TM) vaccine induces immune responses similar to FluMist® and IVR-147.
Figure 34B:
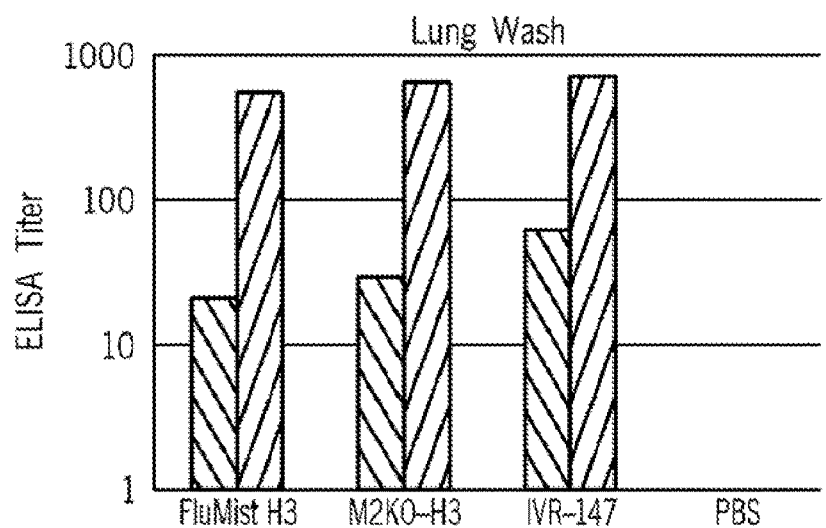
Figure 34C:
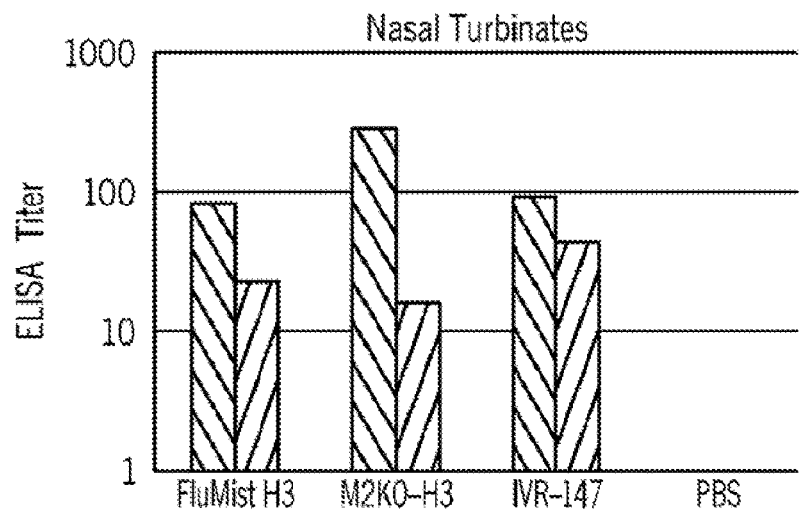

Body weights of animals were monitored for 14 days after infection. Vaccinated mice did not lose any weight. On day 21 post-boost, 3 mice per group were euthanized and their trachea-lung washes, nasal washes, and sera were collected for antibody titer determinations (FIGS. 34A, 34B, and 34C). M2KO(ΔTM) induced both humoral and mucosal antibodies to similar levels as FluMist® and IVR-147 in sera and respiratory tract.

Figure 35A:
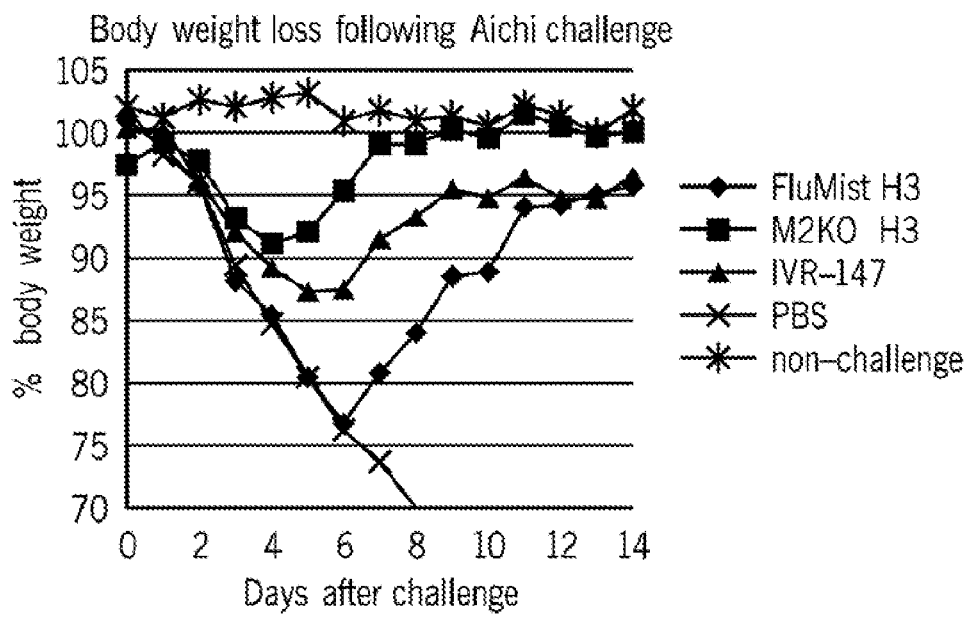
FIGS. 35A and 35B are charts showing that M2KO($\Delta$TM) vaccine protects against Aichi challenge.
Figure 35B:
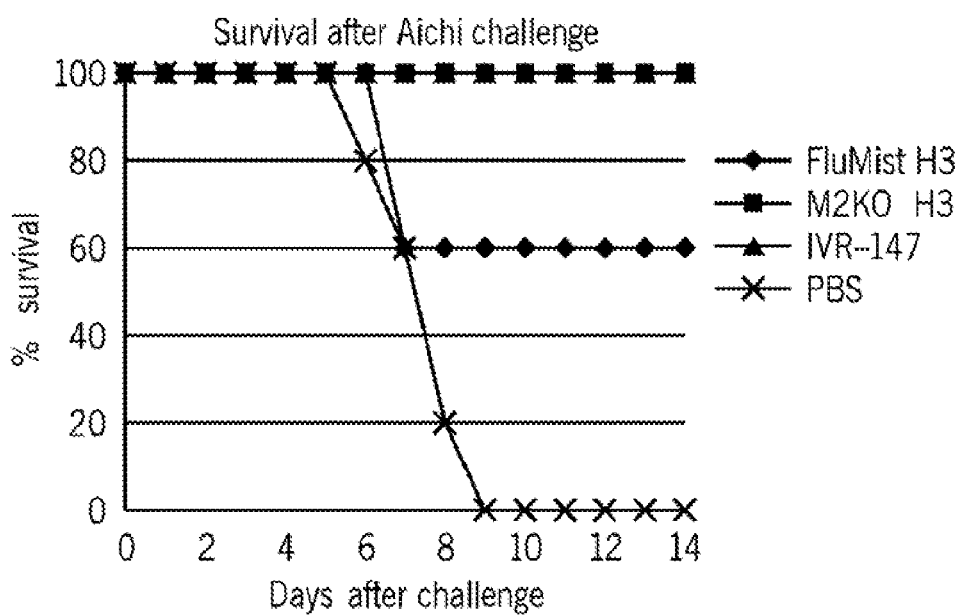

Mice were intranasally challenged with 40MLD$_{50}$ of A/Aichi/2/68 virus six weeks post-boost. Mice were observed for loss of body weight and survival for 14 days (FIGS. 35A and 35B). M2KO(ΔTM) protected mice from lethal Aichi challenge as indicated by less body weight loss (Panel A) and 100% survival (Panel B) in contrast to FluMist®. On day 3 post-challenge, 3 mice per group were euthanized and their lungs and nasal turbinates were collected for virus titer determinations (Table 24). M2KO (ΔTM) controlled the challenge virus better than FluMist® as shown in Table 24.

TABLE 24

Challenge virus titers in respiratory tract.

|  | Lung (Log TCID$_{50}$/g) Mean ± SD | Nasal Turbinate (Log TCID$_{50}$/g) Mean ± SD |
| --- | --- | --- |
| M2KO H3 | 7.05 ± 0.14 | 4.37 ± 1.01 |
| FluMist H3 | 7.32 ± 0.38 | 6.83 ± 1.50 |
| IVR 147 | 7.08 ± 0.14 | 4.87 ± 0.14 |
| PBS | 7.95 ± 0.63 | 6.25 ± 0.29 |

Example 17: Generation of an M2KO(ΔTM) Vaccine Against Highly Pathogenic Avian H5n1 Influenza Virus Summary: M2KO(ΔTM) is an influenza virus that lacks expression of a functional M2 protein. The M2 protein is crucial for initiation of influenza viral infection and for efficient viral RNA incorporation into progeny virions. M2KO(ΔTM) can enter cells and express viral proteins but cannot make infectious progeny viruses due to deletion of the M2 gene. M2KO(ΔTM) is produced in permissive M2 protein expressing cells but not in non-permissive wild-type cells. M2KO(ΔTM) elicits both mucosal and humoral immunity in mice and protects from both homo and heterosubtypic lethal challenge.

The H5N1 M2KO(ΔTM) virus contains the HA (avirulent) and NA genes of A/Vietnam/1203/2004 on the M2KO (ΔTM) backbone. By "M2KO(ΔTM) backbone" is meant the sequence of PR8 comprising the M2KO(ΔTM) (SEQ ID NO:1) mutation. The A/Vietnam/1203/2004 HA (avirulent) and NA sequences used are shown below.

```
>Avirulent VN1203 HA ORF + PR8 non-coding
AGCAAAAGCAGGGGAAAATAAAAACAACCAAAATGGAGAAAATAGTGC

TTCTTTTTGCAATAGTCAGTCTTGTTAAAAGTGATCAGATTTGCATTG

GTTACCATGCAAACAACTCGACAGAGCAGGTTGACACAATAATGGAAA

AGAACGTTACTGTTACACATGCCCAAGACATACTGGAAAAGAAACACA

ACGGGAAGCTCTGCGATCTAGATGGAGTGAAGCCTCTAATTTTGAGAG

ATTGTAGCGTAGCTGGATGGCTCCTCGGAAACCCAATGTGTGACGAAT

TCATCAATGTGCCGGAATGGTCTTACATAGTGGAGAAGGCCAATCCAG

TCAATGACCTCTGTTACCCAGGGGATTTCAATGACTATGAAGAATTGA

AACACCTATTGAGCAGAATAAACCATTTTGAGAAAATTCAGATCATCC

CCAAAAGTTCTTGGTCCAGTCATGAAGCCTCATTAGGGGTGAGCTCAG

CATGTCCATACCAGGGAAAGTCCTCCTTTTTCAGAAATGTGGTATGGC
```

```
-continued
TTATCAAAAAGAACAGTACATACCCAACAATAAAGAGGAGCTACAATA

ATACCAACCAAGAAGATCTTTTGGTACTGTGGGGGATTCACCATCCTA

ATGATGCGGCAGAGCAGACAAAGCTCTATCAAAACCCAACCACCTATA

TTTCCGTTGGGACATCAACACTAAACCAGAGATTGGTACCAAGAATAG

CTACTAGATCCAAAGTAAACGGGCAAAGTGGAAGGATGGAGTTCTTCT

GGACAATTTTAAAGCCGAATGATGCAATCAACTTCGAGAGTAATGGAA

ATTTCATTGCTCCAGAATATGCATACAAAATTGTCAAGAAAGGGGACT

CAACAATTATGAAAAGTGAATTGGAATATGGTAACTGCAACACCAAGT

GTCAAACTCCAATGGGGGCGATAAACTCTAGCATGCCATTCCACAATA

TACACCCTCTCACCATTGGGGAATGCCCCAAATATGTGAAATCAAACA

GATTAGTCCTTGCGACTGGGCTCAGAAATAGCCCTCAAAGAGAGACTA

GAGGATTATTTGGAGCTATAGCAGGTTTTATAGAGGGAGGATGGCAGG

GAATGGTAGATGGTTGGTATGGGTACCACCATAGCAATGAGCAGGGGA

GTGGGTACGCTGCAGACAAAGAATCCACTCAAAAGGCAATAGATGGAG

TCACCAATAAGGTCAACTCGATCATTGACAAAATGAACACTCAGTTTG

AGGCCGTTGGAAGGGAATTTAACAACTTAGAAAGGAGAATAGAGAATT

TAAACAAGAAGATGGAAGACGGGTTCCTAGATGTCTGGACTTATAATG

CTGAACTTCTGGTTCTCATGGAAAATGAGAGAACTCTAGACTTTCATG

ACTCAAATGTCAAGAACCTTTACGACAAGGTCCGACTACAGCTTAGGG

ATAATGCAAAGGAGCTGGGTAACGGTTGTTTCGAGTTCTATCATAAAT

GTGATAATGAATGTATGGAAAGTGTAAGAAATGGAACGTATGACTACC

CGCAGTATTCAGAAGAAGCGAGACTAAAAAGAGAGGAAATAAGTGGAG

TAAAATTGGAATCAATAGGAATTTACCAAATACTGTCAATTTATTCTA

CAGTGGCGAGTTCCCTAGCACTGGCAATCATGGTAGCTGGTCTATCCT

TATGGATGTGCTCCAATGGGTCGTTACAATGCAGAATTTGCATTTAAG

ATTAGAATTTCAGAGATATGAGGAAAAACACCCTTGTTTCTACT

>VN1203 NA ORF + PR8 non-coding
AGCAAAAGCAGGGGTTTAAAATGAATCCAAATCAGAAGATAATAACCA

TCGGATCAATCTGTATGGTAACTGGAATAGTTAGCTTAATGTTACAAA

TTGGGAACATGATCTCAATATGGGTCAGTCATTCAATTCACACAGGGA

ATCAACACCAATCTGAACCAATCAGCAATACTAATTTTCTTACTGAGA

AAGCTGTGGCTTCAGTAAAATTAGCGGGCAATTCATCTCTTTGCCCCA

TTAACGGATGGGCTGTATACAGTAAGGACAACAGTATAAGGATCGGTT

CCAAGGGGGATGTGTTTGTTATAAGAGAGCCGTTCATCTCATGCTCCC

ACTTGGAATGCAGAACTTTCTTTTTGACTCAGGGAGCCTTGCTGAATG

ACAAGCACTCCAATGGGACTGTCAAAGACAGAAGCCCTCACAGAACAT

TAATGAGTTGTCCTGTGGGTGAGGCTCCCTCCCCATATAACTCAAGGT

TTGAGTCTGTTGCTTGGTCAGCAAGTGCTTGCCATGATGGCACCAGTT

GGTTGACGATTGGAATTTCTGGCCCAGACAATGGGGCTGTGGCTGTAT

TGAAATACAATGGCATAATAACAGACACTATCAAGAGTTGGAGGAACA

ACATACTGAGAACTCAAGAGTCTGAATGTGCATGTGTAAATGGCTCTT
```

-continued

```
GCTTTACTGTAATGACTGACGGACCAAGTAATGGTCAGGCATCACATA

AGATCTTCAAAATGGAAAAAGGGAAAGTGGTTAAATCAGTCGAATTGG

ATGCTCCTAATTATCACTATGAGGAATGCTCCTGTTATCCTAATGCCG

GAGAAATCACATGTGTGTGCAGGGATAATTGGCATGGCTCAAATCGGC

CATGGGTATCTTTCAATCAAAATTTGGAGTATCAAATAGGATATATAT

GCAGTGGAGTTTTCGGAGACAATCCACGCCCCAATGATGGAACAGGTA

GTTGTGGTCCGGTGTCCTCTAACGGGGCATATGGGGTAAAAGGGTTTT

CATTTAAATACGGCAATGGTGTCTGGATCGGGAGAACCAAAAGCACTA

ATTCCAGGAGCGGCTTTGAAATGATTTGGGATCCAAATGGGTGGACTG

AAACGGACAGTAGCTTTTCAGTGAAACAAGATATCGTAGCAATAACTG

ATTGGTCAGGATATAGCGGGAGTTTTGTCCAGCATCCAGAACTGACAG

GACTAGATTGCATAAGACCTTGTTTCTGGGTTGAGTTGATCAGAGGGC

GGCCCAAAGAGAGCACAATTTGGACTAGTGGGAGCAGCATATCTTTTT

GTGGTGTAAATAGTGACACTGTGGGTTGGTCTTGGCCAGACGGTGCCG

AGTTGCCATTCACCATTGACAAGTAGTCTGTTCAAAAAACTCCTTGTT

TCTACT
```

Generation of H5N1 M2KO(ΔTM): The avirulent HA and NA of A/Vietnam/1203/2004 (H5N1) were chemically synthesized by GeneArt® Gene Synthesis based on the CDC sequences for each gene (CDC ID: 2004706280, Accession Numbers: EF541467 and EF541403). The sequences of the constructs were confirmed and sub-cloned into appropriate vectors to allow for the generation of seed virus using standard protocols.

M2KO(ΔTM) VN1203avHA,NA (H5N1 M2KO(ΔTM)) virus was amplified in M2CK cells (MDCK cells stably expressing the M2 protein), the supernatant clarified of cell debris and concentrated 100-fold by Centricon Plus-70 (Millipore). This virus was used as the immunogen in the mice study.

Mouse Study Design: Mice (7-8 weeks old, female BALB/c) were intranasally inoculated with H5N1 M2KO (ΔTM) ($10^6$ TCID$_{50}$/mouse), M2KO(ΔTM) CA07HA, NA ($10^6$ TCID$_{50}$/mouse) or VN1203 protein (1.5 μg) administered intramuscularly. Body weight and clinical symptoms were observed for 14 days post-inoculation. Sera was collected on days 7, 14, 21 post-inoculation. Mice were boosted on day 28 with a new prime only group initiated at the same time.

Boost immunization and 'prime only' groups: On day 28 the mice previously inoculated with H5N1 M2KO(ΔTM) were boosted with a second immunization of $10^6$ pfu/mouse. At the same time the 'prime only' groups were given their first dose. Weight loss was followed for all groups following the day 28 inoculation. The mice that received a boost dose of M2KO(ΔTM) vaccine lost at most 5% of their body weight. The 'prime only' group lost up to 10% of their body weight.

TABLE 25

Vaccine groups in mice study

| Group[1] | Immunogen | Doses | Route of Administration | Challenge Virus |
|---|---|---|---|---|
| 1 | H5N1 M2KO(ΔTM) | 2 | Intranasal | Challenged 5 months post-immunization with 20 MLD$_{50}$ A/VN/1203/2004 |
| 2 | H5N1 M2KO(ΔTM) | 1 | Intranasal | |
| 3 | H1N1pdm M2KO(ΔTM) | 2 | Intranasal | |
| 4 | H5 HA VN1203 protein | 2 | Intramuscular | |
| 5 | Naïve (OPTI-MEM ™) | 2 | Intranasal | |
| 6 | H5N1 M2KO(ΔTM) | 1 | Intranasal | Challenged 4 weeks post-immunization with 20 MLD$_{50}$ A/VN/1203/2004 |
| 7 | Naïve (OPTI-MEM ™) | 1 | Intranasal | |

[1] 5 mice/group for survival assessment after challenge

Figure 36:
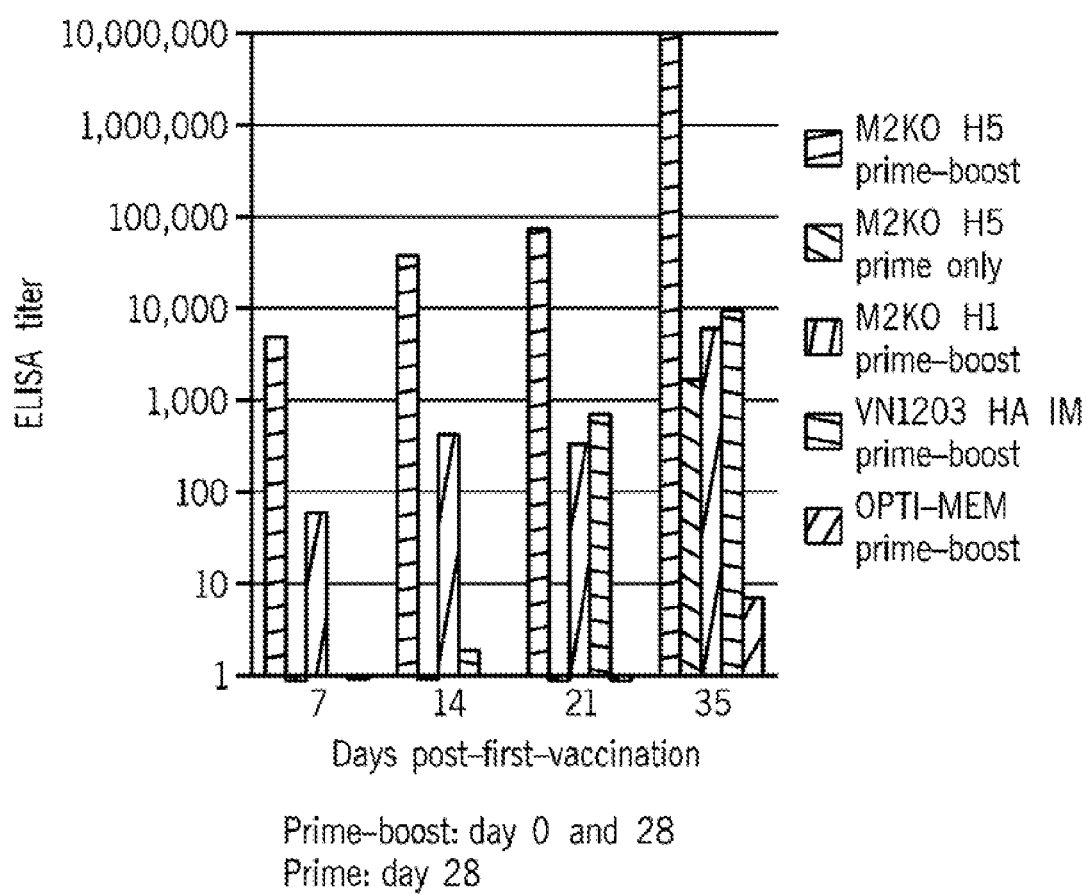
FIG. 36 is a chart showing that H5N1 M2KO($\Delta$TM) vaccine elicits IgG antibody titers against HA.
Figure 37:
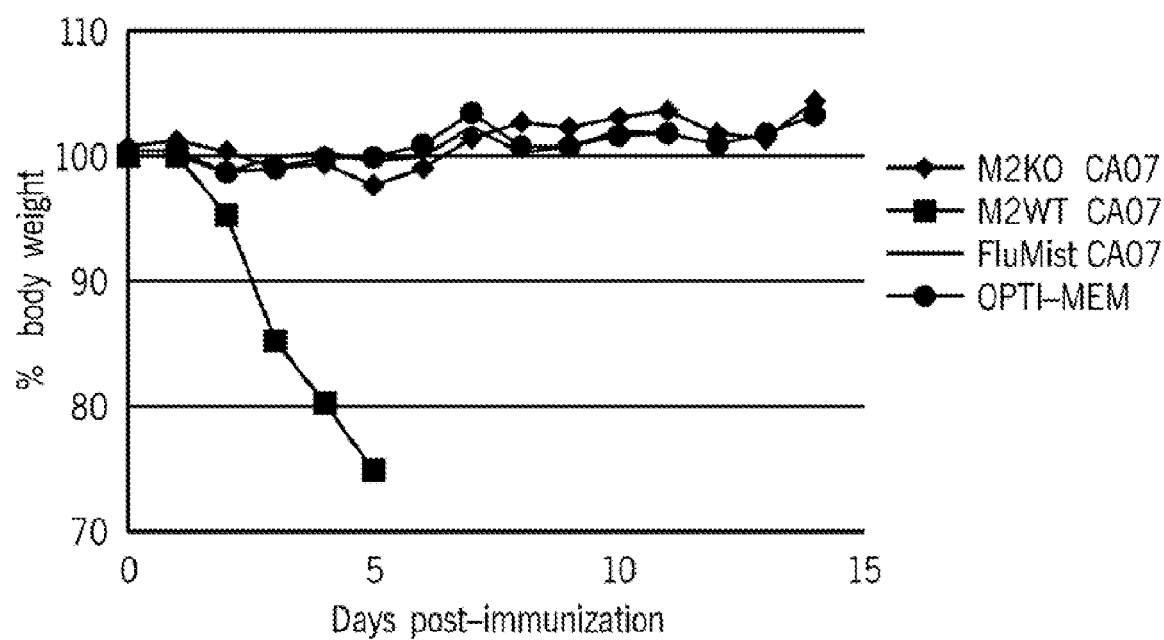
FIG. 37 is a chart showing body weight following administration of M2KO($\Delta$TM) CA07, WT CA07, and FluMist® CA07 vaccines.
Figure 39:
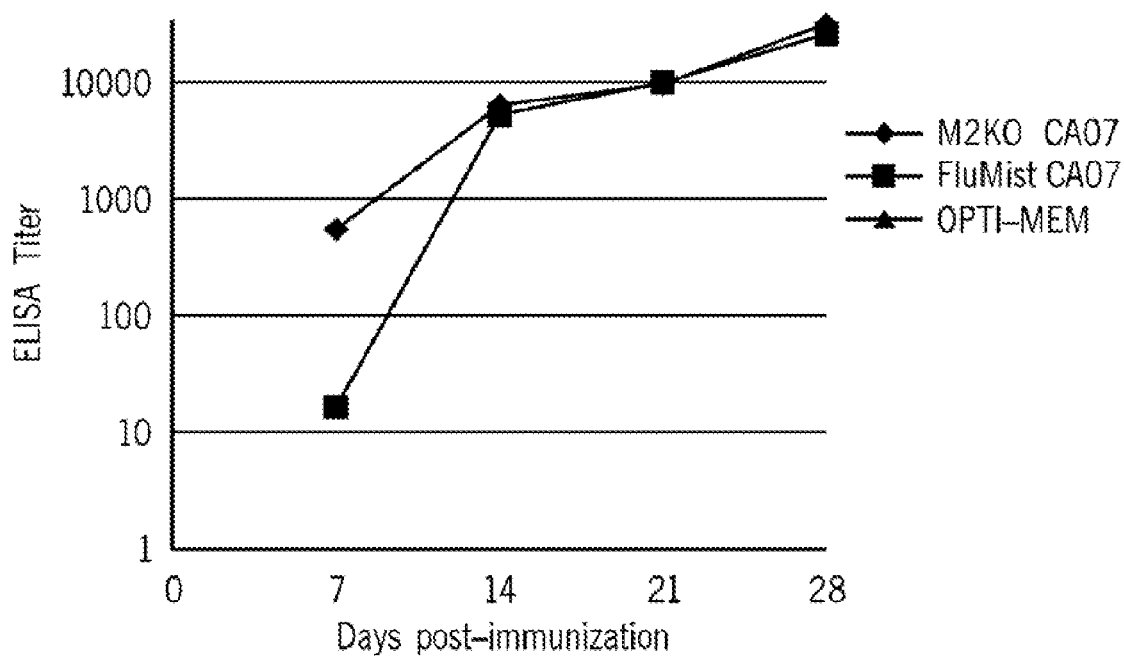
FIG. 39 is a chart showing that M2KO($\Delta$TM) vaccine displays rapid antibody kinetics.

H5N1 M2KO(ΔTM) elicits IgG antibody titers against HA: Sera was obtained from mice on day 7, 14, 21 post-inoculation and analyzed by ELISA for antibodies against the hemagglutinin. M2KO(ΔTM) generated at least 100 fold higher titers than H5 HA protein (FIG. 36). Mice were boosted on day 28 and sera was obtained a week later (day 35). The M2KO(ΔTM) titers were boosted 130 fold, whereas the HA protein only boosted 13 fold. The first week bleed at day 35 for the M2KO(ΔTM) prime only groups demonstrated high IgG titers as the first week of the prime-boost groups.

Figure 54:
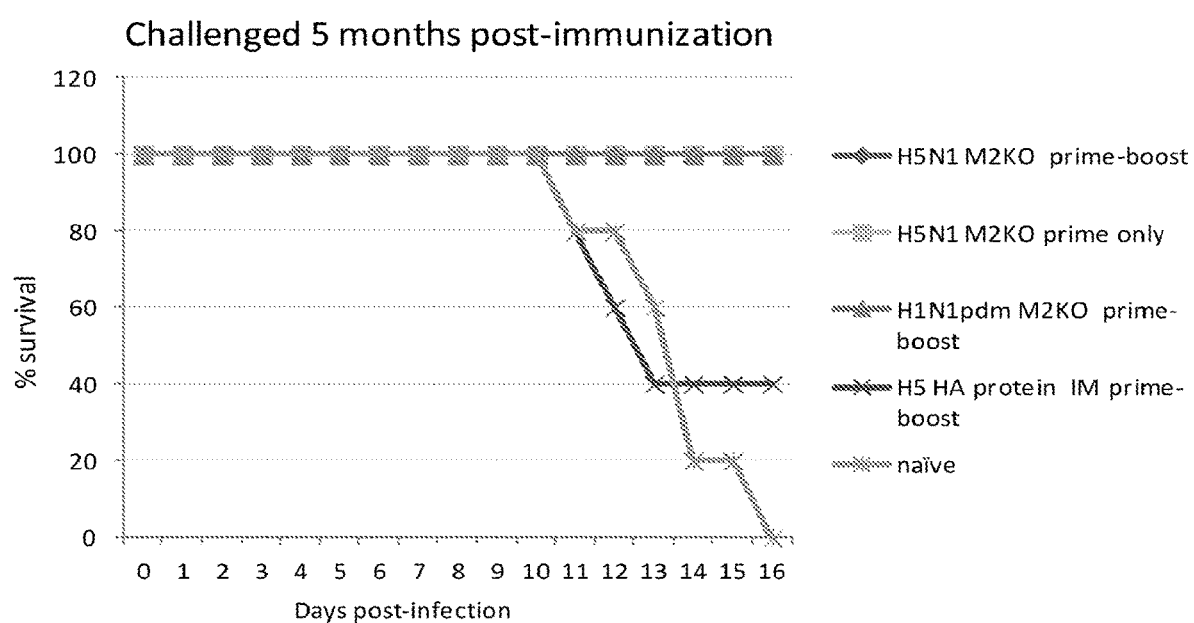
FIG. 54 is a chart showing the percent survival of H5N1 M2KO(ΔTM) vaccinated subjects challenged 5 months post-immunization with Vietnam/1203/2004 virus.
Figure 55:
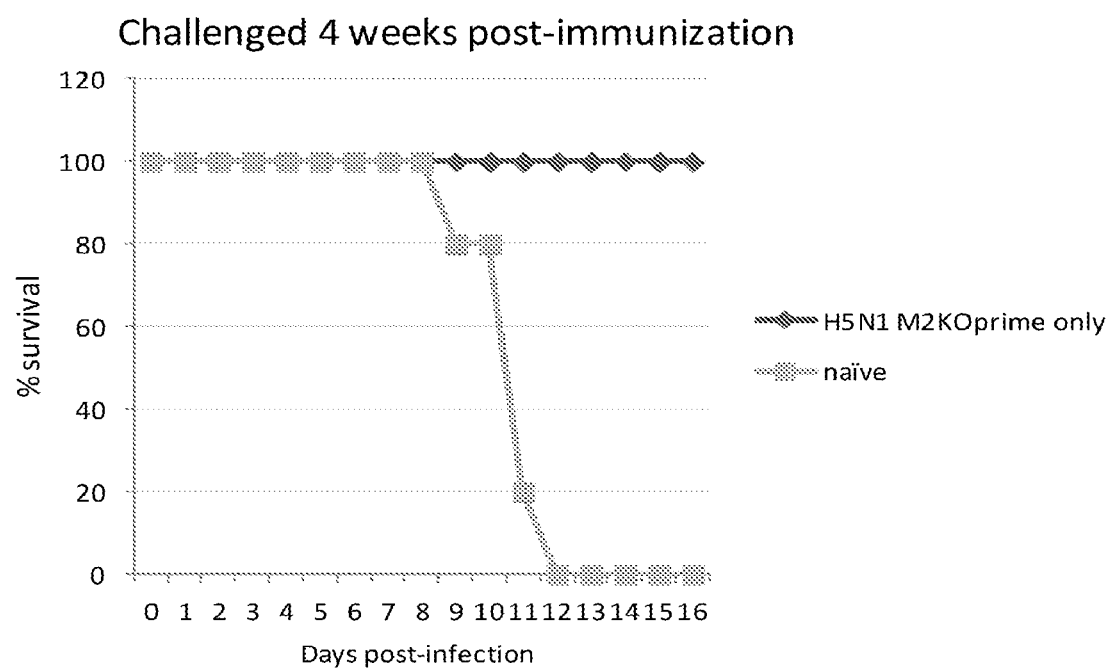
FIG. 55 is a chart showing the percent survival of H5N1 M2KO(ΔTM) vaccinated subjects challenged 4 weeks post-immunization with Vietnam/1203/2004 virus.

Mice were challenged with a lethal dose of Vietnam/1203/2004 virus (20 MLD$_{50}$). All H5N1 M2KO(ΔTM) vaccinated (prime only and prime-boost) mice survived (FIGS. 54 and 55). The high survival rate of mice challenged 5 months post-immunization suggests that the H5N1 M2KO(ΔTM) vaccine primes memory responses. Mice challenged 4 weeks post-immunization had received only one dose of vaccine, indicating that the M2KO(ΔTM) vaccine stimulates a strong immune response. H1N1pdm M2KO(ΔTM) immunized mice also survived H5N1 challenge after 5 months indicating that M2KO(ΔTM) primes cross-reactive immune responses that provide protection against heterologous challenge.

Example 18: H1N1Pdm: FluMist® CA07 vs M2KO(ΔTM) CA07

The HA and NA cDNA clones of A/California/07/2009 (CA07) (H1N1pdm) were generated by standard molecular biology protocols. The sequences of the constructs were confirmed and sub-cloned into appropriate vectors to allow for the generation of seed M2KO(ΔTM) virus and M2WTCA07/PR8 virus using standard protocols. FluMist® CA07 (H1N1pdm) was plaque purified in MDCK cells from FluMist® 2011-2012 vaccine Lot #B11K1802. The A/California/07/2009 (CA07) HA and NA sequences used are shown below.

```
A/California/07/2009 (H1N1) HA in M2KOTMdel
AGCAAAAGCAGGGGAAAACAAAAGCAACAAAAATGAAGGCAATACTAG

TAGTTCTGCTATATACATTTGCAACCGCAAATGCAGACACATTATGTA

TAGGTTATCATGCGAACAATTCAACAGACACTGTAGACACAGTACTAG

AAAAGAATGTAACAGTAACACACTCTGTTAACCTTCTAGAAGACAAGC
```

-continued

ATAACGGGAAACTATGCAAACTAAGAGGGGTAGCCCCATTGCATTTGG

GTAAATGTAACATTGCTGGCTGGATCCTGGGAAATCCAGAGTGTGAAT

CACTCTCCACAGCAAGCTCATGGTCCTACATTGTGGAAACACCTAGTT

CAGACAATGGAACGTGTTACCCAGGAGATTTCATCGATTATGAGGAGC

TAAGAGAGCAATTGAGCTCAGTGTCATCATTTGAAAGGTTTGAGATAT

TCCCCAAGACAAGTTCATGGCCCAATCATGACTCGAACAAAGGTGTAA

CGGCAGCATGTCCTCATGCTGGAGCAAAAAGCTTCTACAAAAATTTAA

TATGGCTAGTTAAAAAAGGAAATTCATACCCAAAGCTCAGCAAATCCT

ACATTAATGATAAAGGGAAAGAAGTCCTCGTGCTATGGGGCATTCACC

ATCCATCTACTAGTGCTGACCAACAAAGTCTCTATCAGAATGCAGATG

CATATGTTTTTGTGGGGTCATCAAGATACAGCAAGAMGTTCAAGCCGG

AAATAGCAATAAGACCCAAAGTGAGGGATCRAGAAGGGAGAATGAACT

ATTACTGGACACTAGTAGAGCCGGGAGACAAAATAACATTCGAAGCAA

CTGGAAATCTAGTGGTACCGAGATATGCATTCGCAATGGAAAGAAATG

CTGGATCTGGTATTATCATTTCAGATACACCAGTCCACGATTGCAATA

CAACTTGTCAAACACCCAAGGGTGCTATAAACACCAGCCTCCCATTTC

AGAATATACATCCGATCACAATTGGAAAATGTCCAAAATATGTAAAAA

GCACAAAATTGAGACTGGCCACAGGATTGAGGAATATCCCGTCTATTC

AATCTAGAGGCCTATTTGGGGCCATTGCCGGTTTCATTGAAGGGGGGT

GGACAGGGATGGTAGATGGATGGTACGGTTATCACCATCAAAATGAGC

AGGGGTCAGGATATGCAGCCGACCTGAAGAGCACACAGAATGCCATTG

ACGAGATTACTAACAAAGTAAATTCTGTTATTGAAAAGATGAATACAC

AGTTCACAGCAGTAGGTAAAGAGTTCAACCACCTGGAAAAAAGAATAG

AGAATTTAAATAAAAAAGTTGATGATGGTTTCCTGGACATTTGGACTT

ACAATGCCGAACTGTTGGTTCTATTGGAAAATGAAAGAACTTTGGACT

ACCACGATTCAAATGTGAAGAACTTATATGAAAAGGTAAGAAGCCAGC

TAAAAAACAATGCCAAGGAAATTGGAAACGGCTGCTTTGAATTTTACC

ACAAATGCGATAACACGTGCATGGAAAGTGTCAAAAATGGGACTTATG

ACTACCCAAAATACTCAGAGGAAGCAAAATTAAACAGAGAAGAAATAG

ATGGGGTAAAGCTGGAATCAACAAGGATTTACCAGATTTTGGCGATCT

ATTCAACTGTCGCCAGTTCATTGGTACTGGTAGTCTCCCTGGGGGCAA

TCAGTTTCTGGATGTGCTCTAATGGGTCTCTACAGTGTAGAATATGTA

TTTAACATTAGGATTTCAGAAGCATGAGAAAAAAACACCCTTGTTTCT

ACT

>A/California/07/2009 (H1N1) NA in M2KOTMdel
AGCAAAAGCAGGAGTTTAAAATGAATCCAAACCAAAAGATAATAACCA

TTGGTTCGGTCTGTATGACAATTGGAATGGCTAACTTAATATTACAAA

TTGGAAACATAATCTCAATATGGATTAGCCACTCAATTCAACTTGGGA

ATCAAAATCAGATTGAAACATGCAATCAAAGCGTCATTACTTATGAAA

ACAACACTTGGGTAAATCAGACATATGTTAACATCAGCAACACCAACT

TTGCTGCTGGACAGTCAGTGGTTTCCGTGAAATTAGCGGGCAATTCCT

-continued

CTCTCTGCCCTGTTAGTGGATGGGCTATATACAGTAAAGACAACAGTG

TAAGAATCGGTTCCAAGGGGGATGTGTTTGTCATAAGGGAACCATTCA

TATCATGCTCCCCCTTGGAATGCAGAACCTTCTTCTTGACTCAAGGGG

CCTTGCTAAATGACAAACATTCCAATGGAACCATTAAAGACAGGAGCC

CATATCGAACCCTAATGAGCTGTCCTATTGGTGAAGTTCCCTCTCCAT

ACAACTCAAGATTTGAGTCAGTCGCTTGGTCAGCAAGTGCTTGTCATG

ATGGCATCAATTGGCTAACAATTGGAATTTCTGGCCCAGACAATGGGG

CAGTGGCTGTGTTAAAGTACAACGGCATAATAACAGACACTATCAAGA

GTTGGAGAAACAATATATTGAGAACACAAGAGTCTGAATGTGCATGTG

TAAATGGTTCTTGCTTTACTGTAATGACCGATGGACCAAGTAATGGAC

AGGCCTCATACAAGATCTTCAGAATAGAAAAGGGAAAGATAGTCAAAT

CAGTCGAAATGAATGCCCCTAATTATCACTATGAGGAATGCTCCTGTT

ATCCTGATTCTAGTGAAATCACATGTGTGTGCAGGGATAACTGGCATG

GCTCGAATCGACCGTGGGTGTCTTTCAACCAGAATCTGGAATATCAGA

TAGGATACATATGCAGTGGGATTTTCGGAGACAATCCACGCCCTAATG

ATAAGACAGGCAGTTGTGGTCCAGTATCGTCTAATGGAGCAAATGGAG

TAAAAGGGTTTTCATTCAAATACGGCAATGGTGTTTGGATAGGGAGAA

CTAAAAGCATTAGTTCAAGAAACGGTTTTGAGATGATTTGGGATCCGA

ACGGATGGACTGGGACAGACAATAACTTCTCAATAAAGCAAGATATCG

TAGGAATAAATGAGTGGTCAGGATATAGCGGGAGTTTTGTTCAGCATC

CAGAACTAACAGGGCTGGATTGTATAAGACCTTGCTTCTGGGTTGAAC

TAATCAGAGGGCGACCCAAAGAGAACACAATCTGGACTAGCGGGAGCA

GCATATCCTTTTGTGGTGTAAACAGTGACACTGTGGGTTGGTCTTGGC

CAGACGGTGCTGAGTTGCCATTTACCATTGACAAGTAATTTGTTCAAA

AAACTCCTTGTTTCTACT

Mice (7-8 weeks old, female BALB/c) were intranasally inoculated with M2KO(ΔTM) CA07 ($10^6$ $TCID_{50}$/mouse), M2WT CA07 ($10^6$ $TCID_{50}$/mouse), FluMist® CA07 ($10^6$ $TCID_{50}$/mouse) or OPTI-MEM™ as naïve control. Body weight and clinical symptoms were observed for 14 days post-inoculation. FIG. 37 shows that M2KO(ΔTM) and FluMist® vaccinated mice did not lose weight whereas the virus that contains the WT M2 loses weight and succumbs to infection. These results demonstrate that deletion of the M2 gene attenuates the virus and that M2KO(ΔTM) is attenuated.

FIG. 38 M2KO(ΔTM), FluMist,® and M2 wild-type viral titers lungs and nasal terminates. Lungs and nasal turbinates were harvested on day 3 post-vaccination for titration of virus on cells. No virus was detected in either the lungs or the nasal turbinates in the M2KO(ΔTM) immunized mice. In contrast, FluMist® did have virus replication in both the lung and nasal turbinates although at lower levels than the wild-type virus.

FIG. 39M2KO(ΔTM) and FluMist® titers in sera collected 7, 14, and 21 days post-inoculation and anti-HA IgG titers were determined by ELISA. M2KO(ΔTM) induced higher responses that were detected earlier than FluMist® responses. By day 21 peak antibody levels were reached by both viruses.

Figure 40:
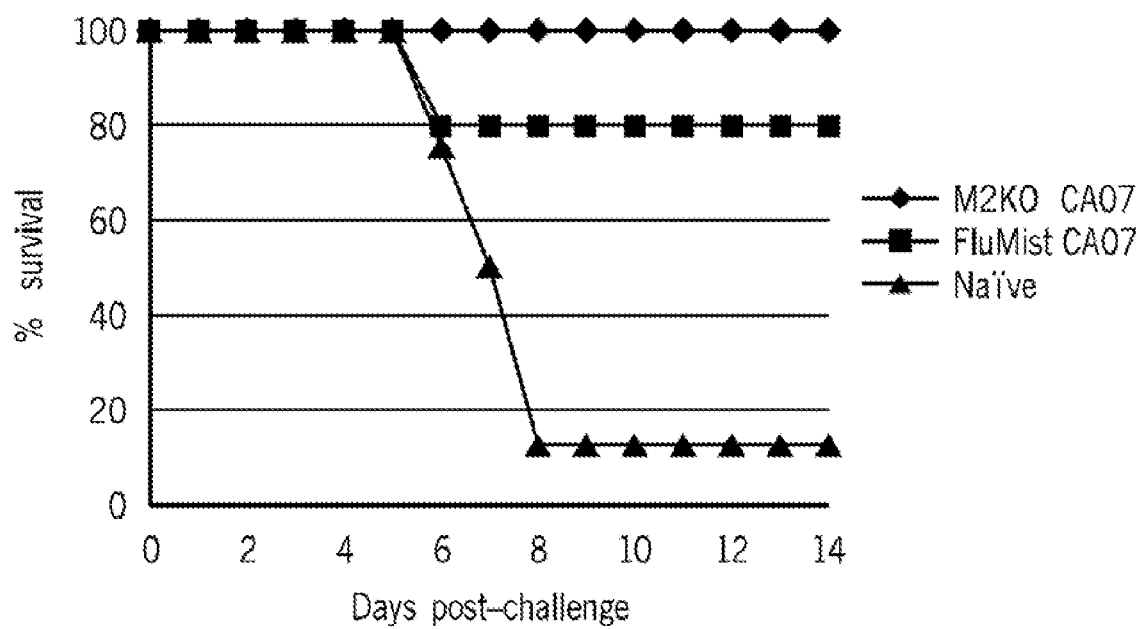
FIG. 40 is a chart showing that M2KO($\Delta$TM) vaccine protects against heterologous challenge with H3N2 virus, A/Aichi/2/1968.
Figure 41A:
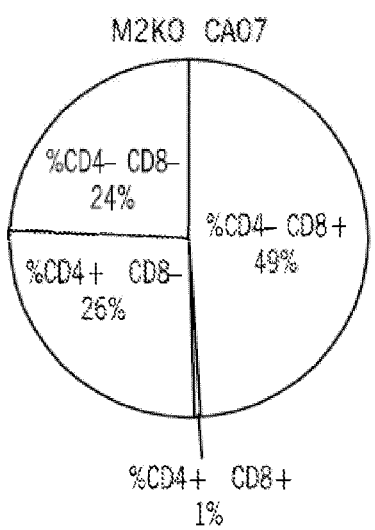
FIGS. 41A, 41B, and 41C are charts showing that M2KO (ΔTM) vaccine primes for cellular responses that are recalled upon challenge.
Figure 41B:
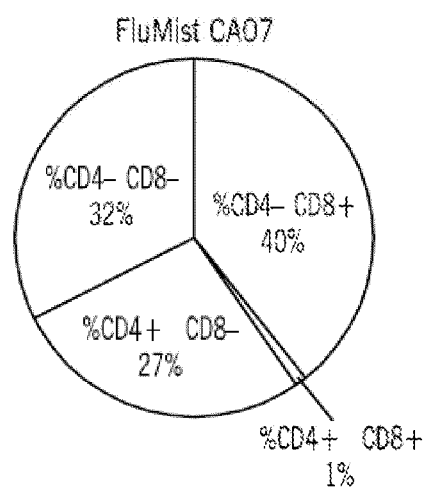
Figure 41C:
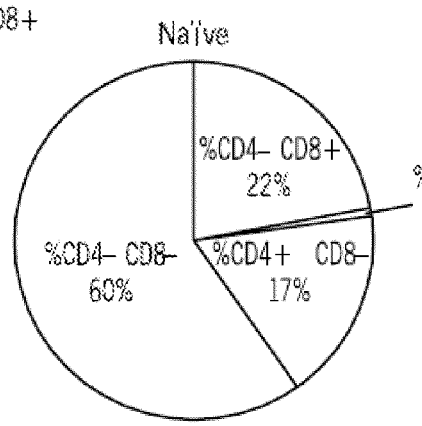
Figure 42:
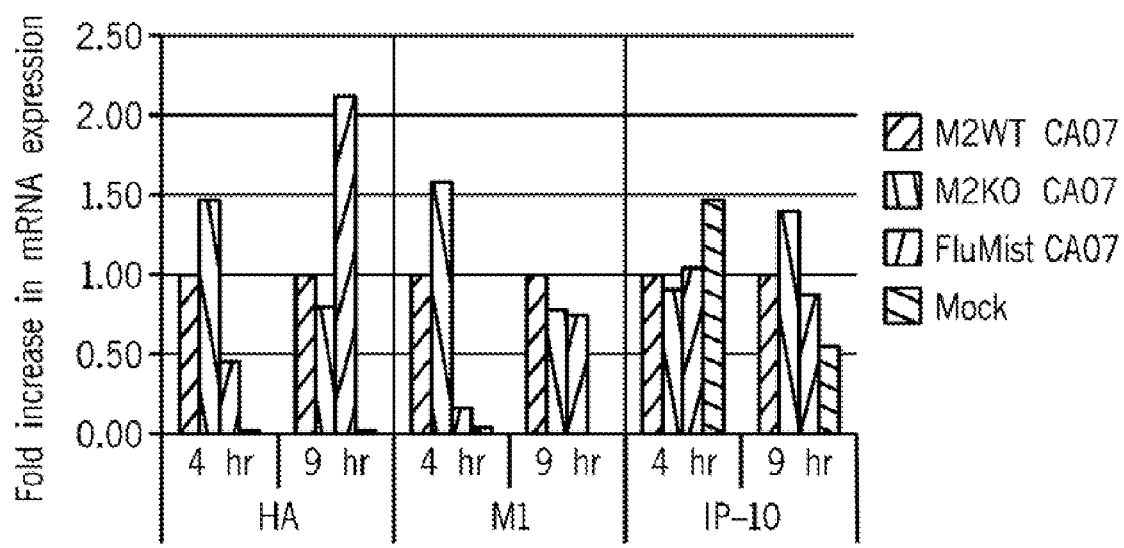
FIG. 42 is a chart showing that M2KO(ΔTM) virus generates mRNA levels similar to virus wild-type for M2.
Figure 43:
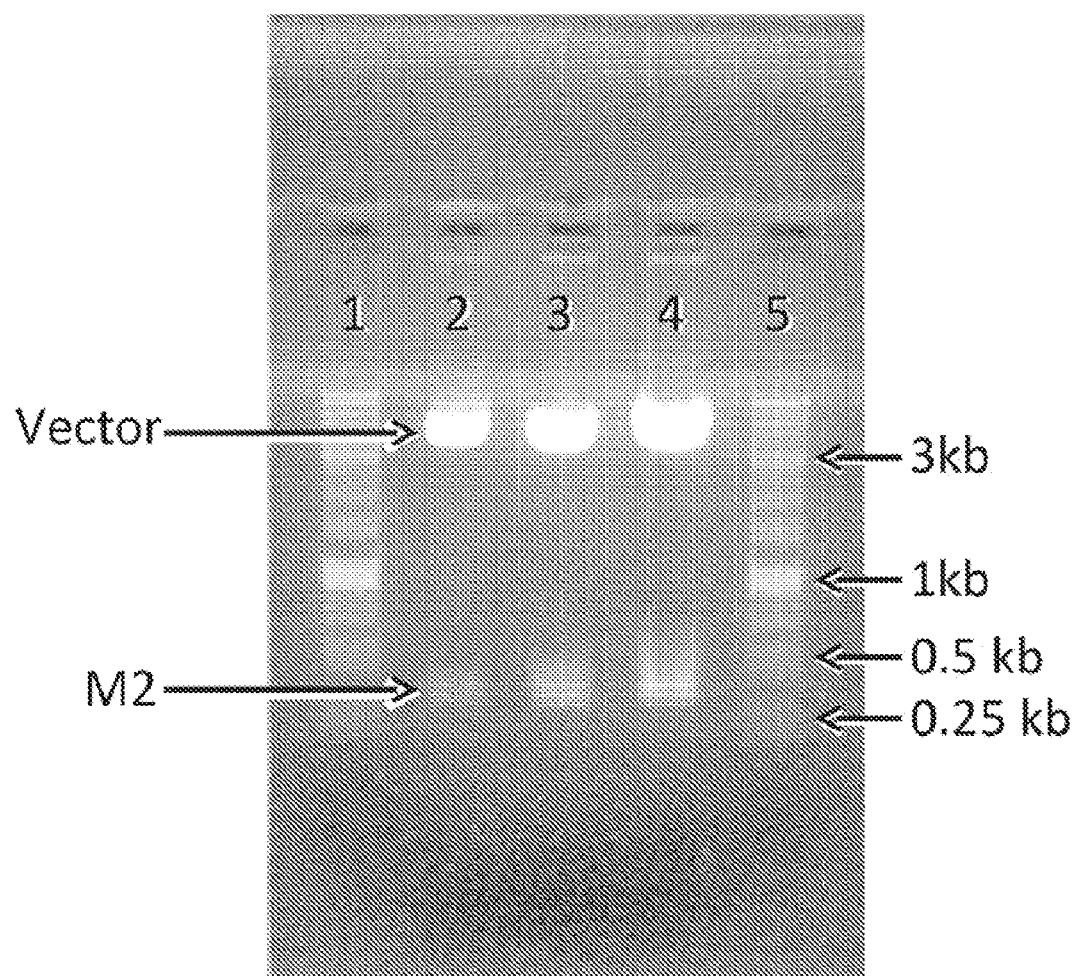
FIG. 43 is an agarose gel showing restriction digests of the pCMV-PR8-M2 expression plasmid. Lanes 1 & 5; 1 Kb DNA Ladder (Promega, Madison, Wis., USA), Lane 2-4; Eco R1 digested pCMLV-PR8-M2: 0.375 μg (Lane 2), 0.75 μg (Lane 3), and 1.5 μg (Lane 4).

FIG. 40 shows the percent survival of mice challenged 12 weeks post-immunization with 40 MLD$_{50}$ of heterologous virus, mouse-adapted influenza A/Aichi/2/1968 (H3N2). Body weight change and clinical symptoms were observed for 14 days after challenge. All the M2KO(ΔTM) (H1N1pdm HA,NA) immunized mice were protected against the Aichi (H3N2) challenge whereas only 80% of the FluMist® (H1N1pdm HA,NA) were protected. The surviving FluMist® mice lost close to 20% of their body weight whereas M2KO(ΔTM) mice lost ~10% of their body weight.

Table 26 shows the virus titers in the lungs and nasal turbinates that were collected on day 3 post-challenge. M2KO(ΔTM) and FluMist® controlled challenge virus replication in the lungs and nasal turbinates to similar levels whereas naïve mice displayed virus titers that were a log higher in both the lung and the nasal turbinates.

Intracellular staining of cells in bronchoalveolar lavage (BAL). BAL was collected 3 days post-challenge and stained with surface markers for immunostaining by flow cytometry to detect CD8+CD4+, CD8+CD4−, CD8−CD4+, CD8−CD4− cell populations. Both CD4+ and CD8+ cell populations were greater in the vaccinated mice than the naïve mice indicating that M2KO(ΔTM) primed for a cellular response similar to FluMist®. M2KO(ΔTM) vaccinated mice had greater CD8+CD4− cell population than FluMist® (49% vs 40%) (FIGS. 41A, 41B, and 41C).

TABLE 26

Virus titers in respiratory tract of mice.

| | Lung (log pfu/g) | Nasal Turbinate (log pfu/g) |
|---|---|---|
| M2KO CA07 | 5.95 ± 0.59 | 5.61 ± 0.47 |
| FluMist CA07 | 5.94 ± 0.46 | 3.88 ± 0.64 |
| Naive | 6.86 ± 0.06 | 6.52 ± 1.05 |

Example 19 M2KO(ΔTM) mRNA Expression Relative to FluMist® and Wild-Type Virus In some embodiments, the M2KO(ΔTM) virus is produced in cells that stably provide M2 protein in trans resulting in a virus that has functional M2 protein in the viral membrane but does not encode M2 in its genome. Therefore, we hypothesize that the M2KO(ΔTM) virus behaves similar to wild-type virus in the initial infection and first round of replication in normal cells. We suggest that mRNA levels of viral antigens are similar to wild-type levels early in infection and stimulate a potent immune response sooner than attenuated replicating viral vaccines.

Human lung carcinoma (A549) cells were infected at a multiplicity of infection of 0.5 with M2KO(ΔTM), FluMist® and wild-type viruses. Unabsorbed virus was removed by washing five times with PBS. After addition of virus growth media, the infected cells were placed in the 35° C. $CO_2$ incubator. No trypsin was added to the growth medium to ensure single-cycle replication for all viruses. Cell monolayers were harvested and RNA extracted at 4, 9 and 22 hours post infection.

Total RNA (100 ng) from control and infected A549 cells were used for quantitative RT-PCR analysis. cDNA was synthesized with oligo-dT primers and Superscript II reverse transcriptase(Invitrogen) and quantified by real-time quantitative PCR analysis using gene-specific primers for an early influenza gene, M1, and a late influenza gene, HA and cytokine IP-10 gene. Reactions were performed using SYBR Green reagent (Invitrogen, Carlsbad) according to the manufacturer's instructions. Reaction efficiency was calculated by using serial 10-fold dilutions of the housekeeping gene γ-actin and sample genes. Reactions were carried out on an ABI 7300 realtime PCR system (Applied Biosystems, Foster City, Calif., USA) and the thermal profile used was Stage 1: 50° C. for 30 min; Stage 2: 95° C. for 15 min; Stage 3: 94° C. for 15 sec, 55° C. for 30 sec; and 72° C. for 30 sec, repeated for 30 cycles. All quantitations (threshold cycle [CT] values) were normalized to that of the housekeeping gene to generate ΔCT, and the difference among the ΔCT value of the sample and that of the reference (wild-type sample) was calculated as −ΔΔCT. The relative level of mRNA expression was expressed as 2-ΔΔCT.

M2KO(ΔTM) virus HA mRNA expression was similar to wild-type M2 virus for H3 (Table 27), PR8 (Table 28) and H1N1pdm (FIG. 42) at 4 hour post-infection. Cold-adapted FluMist® was less than wild-type and M2KO(ΔTM) in the early timepoints due to slower replication kinetics. When M1, an early timepoint gene, mRNA expression was tested, similar results were observed (Table 27, FIG. 42). These results suggest that M2KO(ΔTM) generates similar levels of mRNA in the early infection cycle to produce de novo viral antigens that create a 'danger signal' similar to wild-type virus and induce a potent immune response.

TABLE 27

Relative mRNA expression of H3 HA genes.

| | 2^-ΔΔCt (compare to IVR-147) | | |
|---|---|---|---|
| | neat | 1:10 dilution | 1:100 dilution |
| 4 hr pi | | | |
| IVR-147 | 1.0 | 1.0 | 1.0 |
| M2KO | 15.4 | 16.1 | 10.8 |
| FluMist | 2.3 | 2.1 | 1.4 |
| Mock | 0.0 | 0.0 | N/A |
| 22 hr pi | | | |
| IVR-147 | 1.0 | 1.0 | 1.0 |
| M2KO | 1.0 | 1.4 | 1.9 |
| FluMist | 1.8 | 3.1 | 1.5 |
| Mock | 0.0 | 0.0 | N/A |

TABLE 28

Relative mRNA expression of the PR8 HA and M1 genes.

| | | HA | | M1 | |
|---|---|---|---|---|---|
| | Sample | neat | 1:10 | neat | 1:10 |
| 4 hr p.i. | PR8 WT | 1.00 | 1.00 | 1.00 | 1.00 |
| | PR8 M2KOTMdel | 3.07 | 1.29 | 3.15 | 2.64 |
| | Mock | 0.02 | 0.30 | 0.15 | 0.32 |
| 9 hr p.i. | PR8 WT | 1.00 | 1.00 | 1.00 | 1.00 |
| | PR8 M2KOTMdel | 2.05 | 3.27 | 4.04 | 5.11 |
| | Mock | 0.00 | 0.00 | 0.00 | 0.00 |

Example 20: Generation of M2 Vero Production Cells

The M2 gene of PR8 virus was cloned into expression vector pCMV-SC (Stratagene, La Jolla, Calif.) by standard molecular techniques to generate pCMV-PR8-M2. The plasmid was digested with EcoR1 to confirm the presence of the 300 bp M2 gene and the 4.5 Kb vector as shown in FIG. 43.

The sequence of the plasmid containing the M2 gene insert was confirmed as shown in FIG. 44.

Generation of M2 Vero cells: The pCMV-PR8-M2 plasmid described earlier and containing a neomycin resistant gene, was transfected into Vero cells (ATCC CCL-81) by using the Trans IT-LT1 transfection reagent (Mirus) according to the manufacturer's instructions. Briefly, on the day before transfection, Vero cells were plated at $5 \times 10^5$ cells/ 100-mm dish. On day 1, 10 µg of plasmid DNA was mixed with 20 µg of Trans IT-LT1 in 0.3 ml of OptiMEM (Invitrogen) and was incubated with these cells at 37° C. in 5% $CO_2$ overnight. On day 2, the transfection mixture was replaced with a complete medium that is modified Eagle's medium (MEM) supplemented with 5% newborn calf serum. The medium also contained 1 mg/ml of geneticin (Invitrogen), a broad spectrum antibiotic that is used to select mammalian cells expressing the neomycin protein. Resistant cells (Vero cells stably expressing M2 gene) began to grow in the selection medium, the medium was replaced with fresh selection medium and geneticin-resistant clones were isolated by limited dilution in TC-96 plates. The surface expression of the M2 protein was demonstrated by immunostaining using a M2 specific monoclonal antibody, 14C2 (Santa Cruz Biotechnology).

Infection of parental and modified M2 Vero cells with M2KO(ΔTM) virus: The ability of M2 Vero cells to serve as production cells for M2KO(ΔTM) virus was tested by infection with M2KO(ΔTM)-PR8 virus. Briefly, monolayers of M2 Vero and parent Vero cells were infected with ten-fold serial dilutions ($10^{-1}$ to $10^{-6}$) of M2KO(ΔTM)-PR8 virus using standard influenza infection procedures. The infected cells were incubated at 35° C. and observed for cytopathic effect (CPE) daily. Only M2 Vero cells displayed CPE indicating virus growth. Supernatant was harvested on day 4 from the $10^{-3}$ well and virus titer was determined by $TCID_{50}$ assay on MDCK cells stably expressing M2 gene (M2CK). M2KO(ΔTM)-PR8 virus titer grown in M2 Vero cells was $10^{6.75}$ $TCID_{50}$/ml indicating that M2 Vero cells can serve as production cells for the manufacture of M2KO (ΔTM) vaccine.

Example 21: Intradermal Delivery of Influenza Vaccines

This example demonstrates the immunogenicity of the seasonal influenza vaccine, FluLaval (2011-2012 formulation), when administered intramuscularly (IM), intradermally (ID), and using a subcutaneous microneedle device such as that described in published U.S. Patent Application 2011/0172609. Hairless guinea pigs were inoculated on day 0 and select groups were boosted on day 30. Sera was collected on days 0, 30 and 60 and analyzed by enzyme-linked immunosorbent assay (ELISA) for hemagglutinin-specific IgG responses.

Figure 51:
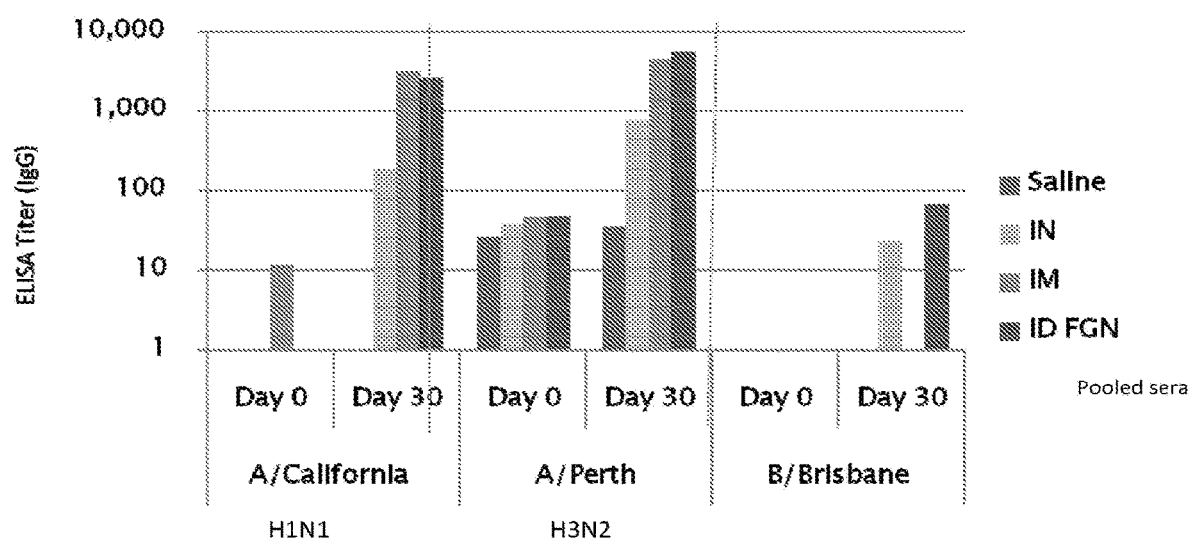
FIG. 51 is a chart showing IgG titers in subjects vaccinated with A/California, A/Perth, and B/Brisbane viruses intranasally (IN), intramuscularly (IM) and intradermally (ID FGN).
Figure 52:
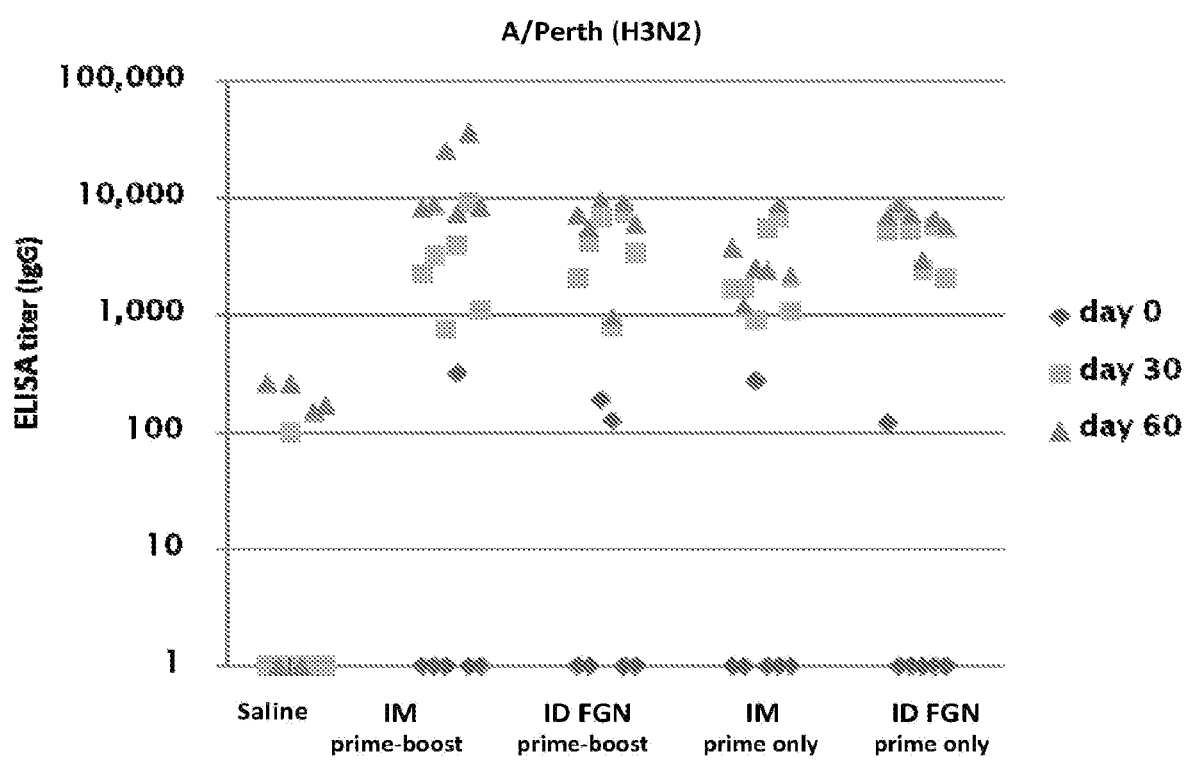
FIG. 52 is a chart showing IgG titers in subjects administered a priming does or a priming and booster dose of A/Perth (H3N2) vaccine intramuscularly (IM) or intradermally (ID FGN).

Results are shown in FIGS. 51-53. The data shows qualitative absorbance of antibody levels to the three strains formulated in the seasonal influenza vaccine FluLaval: A/California/7/2009 NYMC X-181, A/Victoria/210/2009 NYMC X-187 (an A/Perth/16/2009-like virus), and B/Brisbane/60/2008. At day 30, IM and ID delivery produced identical IgG responses to all viral HA. The ID prime only groups displayed higher titers at day 60, suggesting that ID delivery induces long lasting immunity to all viral HA.

What is claimed is:

1. A recombinant influenza A virus comprising a mutant influenza M gene, wherein the mutant M gene comprises two stop codons and a deletion, wherein the two stop codons are at a position corresponding to nucleotides 786-791 of SEQ ID NO: 28 with respect to the M gene coding sequence, and wherein the deletion is at a position corresponding to nucleotides 792-842 of SEQ ID NO: 28 with respect to the M gene coding sequence.

2. A recombinant influenza A virus comprising a mutant influenza M gene, wherein the mutant M gene comprises two stop codons and a G to C substitution, wherein the two stop codons are at a position corresponding to nucleotides 786-791 of SEQ ID NO: 28 with respect to the M gene coding sequence, and wherein the G to C substitution is at a position corresponding to nucleotide 52 of SEQ ID NO: 28 with respect to the M gene coding sequence.

3. A recombinant influenza A virus comprising a mutant influenza M gene, wherein the mutant M gene comprises two stop codons, a deletion, and a G to C substitution, wherein the two stop codons are at a position corresponding to nucleotides 786-791 of SEQ ID NO: 28 with respect to the M gene coding sequence, and wherein the deletion is at a position corresponding to nucleotides 792-842 of SEQ ID NO: 28, and wherein the G to C substitution is at a position corresponding to nucleotide 52 of SEQ ID NO: 28 with respect to the M gene coding sequence.

4. The recombinant influenza virus of claim 1, wherein mutation of the M gene results in failure of the virus to express the M2 protein, or causes the virus to express a truncated M2 protein having the amino acid sequence of SEQ ID NO:4.

5. The recombinant influenza virus of claim 1, wherein the mutant M gene does not revert to wild-type or to a non-wild-type sequence encoding a functional M2 protein for at least 10 passages in an in vitro host cell system, wherein the host cell is modified to produce a wild-type version of the mutant gene, thereby providing the gene product to the virus in trans.

6. The recombinant virus of claim 1, wherein the virus is non-pathogenic in a mammal infected with the virus.

7. The recombinant virus of claim 5, wherein the in vitro cell system comprises Chinese Hamster Ovary cells or Vero cells.

8. A composition comprising the recombinant influenza A virus of claim 1.

9. A composition comprising the recombinant influenza A virus of claim 2.

10. A composition comprising the recombinant influenza A virus of claim 3.

11. The composition of claim 8, wherein mutation of the M gene results in failure of the virus to express the M2 protein, or causes the virus to express a truncated M2 protein having the amino acid sequence of SEQ ID NO:4.

12. The composition of claim 8, wherein the composition is non-pathogenic to a mammal administered the composition.

13. The composition of claim 8, further comprising an adjuvant.

14. A method for propagating a recombinant influenza virus, comprising: contacting a host cell with the recombinant influenza virus of claim 1 and incubating the host cell for a sufficient time and under conditions suitable for viral replication, wherein the host cell is modified to produce a wild-type version of the influenza M gene, thereby providing the gene product to the virus in trans.

15. The method of claim 14, further comprising isolating progeny virus particles.

16. The method of claim 15, further comprising formulating the virus particles into a vaccine.

17. The method of claim 14, wherein the virus fails to express the M2 protein, or expresses a truncated M2 protein having the amino acid sequence of SEQ ID NO:4.

18. The method of claim 14, wherein the virus is non-pathogenic to a mammal administered the virus.

19. The method of claim 14, wherein the mutant M gene does not revert to wild-type or to a non-wild-type sequence encoding a functional M2 protein for at least 10 passages of the host cell.

20. The method of claim 14, wherein the host cell is a CHO cell or a Vero cell.

* * * * *